US009918666B2

(12) United States Patent
Yousefi et al.

(10) Patent No.: US 9,918,666 B2
(45) Date of Patent: Mar. 20, 2018

(54) SYSTEMS AND METHODS FOR PHYSIOLOGICAL SIGNAL ENHANCEMENT AND BIOMETRIC EXTRACTION USING NON-INVASIVE OPTICAL SENSORS

(71) Applicant: The Board of Regents, The University of Texas System, Austin, TX (US)

(72) Inventors: Rasoul Yousefi, Dallas, TX (US); Mehrdad Nourani, Plano, TX (US)

(73) Assignee: The Board of Regents, The University of Texas System, Austin, TX (US)

( * ) Notice: Subject to any disclaimer, the term of this patent is extended or adjusted under 35 U.S.C. 154(b) by 452 days.

(21) Appl. No.: 14/595,866

(22) Filed: Jan. 13, 2015

(65) Prior Publication Data

US 2015/0196257 A1    Jul. 16, 2015

Related U.S. Application Data

(60) Provisional application No. 61/926,773, filed on Jan. 13, 2014.

(51) Int. Cl.
*A61B 5/1455* (2006.01)
*A61B 5/024* (2006.01)
(Continued)

(52) U.S. Cl.
CPC .......... *A61B 5/14551* (2013.01); *A61B 5/024* (2013.01); *A61B 5/0816* (2013.01); *A61B 5/7246* (2013.01)

(58) Field of Classification Search
None
See application file for complete search history.

(56) References Cited

U.S. PATENT DOCUMENTS 6,246,897 B1   6/2001 Foo et al.
7,383,070 B2   6/2008 Diab et al.
(Continued)

FOREIGN PATENT DOCUMENTS

WO    20030063697 A1    8/2003

OTHER PUBLICATIONS

Jong Yong A. Foo, Stephen J. Wilson, "A computational system to optimise noise rejection in photoplethysmography signals during motion or poor perfusion states," Med Biol Eng Comput, vol. 44, pp. 140-145, Jan. 26, 2006.
(Continued)

*Primary Examiner* — Eric Winakur
*Assistant Examiner* — Marjan Fardanesh
(74) *Attorney, Agent, or Firm* — Schultz & Associates, P.C.

(57) ABSTRACT

A system and method for signal processing to remove unwanted noise components including: (i) wavelength-independent motion artifacts such as tissue, bone and skin effects, and (ii) wavelength-dependent motion artifact/noise components such as venous blood pulsation and movement due to various sources including muscle pump, respiratory pump and physical perturbation. Disclosed are methods, analytics, and their uses for reliable perfusion monitoring, arterial oxygen saturation monitoring, heart rate monitoring during daily activities and in hospital settings and for extraction of physiological parameters such as respiration information, hemodynamic parameters, venous capacity, and fluid responsiveness. The system and methods disclosed are extendable to include monitoring platforms for perfusion, hypoxia, arrhythmia detection, airway obstruction detection and sleep disorders including apnea.

21 Claims, 36 Drawing Sheets

(51) Int. Cl.
A61B 5/00 (2006.01)
A61B 5/08 (2006.01)

(56) References Cited

U.S. PATENT DOCUMENTS

| | | | |
|---|---|---|---|
| 8,444,570 | B2 | 5/2013 | McGonigle et al. |
| 8,571,623 | B2 | 10/2013 | Baker, Jr. et al. |
| 2013/0079606 | A1 | 3/2013 | McGonigle et al. |
| 2013/0137936 | A1 | 5/2013 | Baker, Jr. et al. |
| 2013/0172767 | A1 | 7/2013 | Dripps et al. |

OTHER PUBLICATIONS

Rasoul Yousefi, Mehdrad Nourani, Issa Panahi, "Adaptive Cancellation of Motion Artifact in Wearable Biosensors," Conf Proc IEEE Eng Med Biol Sac, pp. 2004-2008, Aug. 2012.
Rasoul Yousefi, Mehdrad Nourani, Sarah Ostadabbas, Issa Panahi, "A Motion-Tolerant Adaptive Algorithm for Wearable Photoplethysmographic Biosensors," Biomedical and Health Informatics, IEEE Journal of, vol. 18, issue 2, pp. 670-681, May 20, 2013.
J. Lee, J.P. Florian, and K.H. Chon, "Respiratory Rate Extraction from Pulse Oximeter and Electrocardiographic Recordings," Physiol. Meas., vol. 32, No. 11, pp. 1763-1773, Nov. 2011.
J. Lee and K.H. Chon, "Time-Varying Autoregressive Model Based Multiple Modes Particle Filtering Algorithm for Respiratory Rate Extraction from Pulse Oximeter," IEEE Trans. Biomed. Eng., vol. 58, No. 3, pp. 790-794, Mar. 2011.
P.A. Leonard, J.G. Douglas, N.R. Grubb, D. Clifton, P.S. Addison, and J.N. Watson, "A Fully Automated Algorithm for the Determination of Respiratory Rate from the Photoplethysmogram," J. Clin. Monit. Comput., vol. 20, No. 1, pp. 33-36, Feb. 2006.
Y.D. Lin, W.T. Liu, C.C. Tsai, and W.H. Chen, "Coherence Analysis Between Respiration and PPG Signal by Bivariate AR Model,"World Acad. Sci. Eng. Technol., vol. 3, No. 5, pp. 1168-1173, 2009.
K.V. Madhav, M.R. Ram, E.H. Krishna, K.N. Reddy, and K.A. Reddy, "Estimation of Respiration Rate from ECG, BP and PPG Signals Using Empirical Mode Decomposition," in Proc. 28th IEEE I2MTC, Hangzhou, China, pp. 1611-1664, May 10-12, 2011.
K.V. Madhav, M.R. Ram, E.H. Krishna, K.A. Reddy, and K.N. Reddy, "Estimation of Respiratory Rate from Principal Components of Photoplethysmographic Signals," in Proc. of 2010 IEEE EMBS conf. on Biomed. Eng. & Sciences, IECBES-2010, Kuala Lumpur, Malaysia, pp. 311-314, Nov./Dec. 2010.
K.V. Madhav, M.R. Ram, E.H. Krishna, and K.A. Reddy, "Monitoring Respiratory Activity Using PPG Signals by Order Reduced-Modified Covariance Ar Technique," in Proc. 4th IEEE CBBE, Chengudu, China, pp. 1-4, Jun. 18-20, 2010.
K.V. Madhav, M.R. Ram, E.H. Krishna, N. R. Komalla, K.A. Reddy, "Robust Extraction of Respiratory Activity From PPG Signals Using Modified MSPCA," Instrumentation and Measurement, IEEE Transactions on , vol. 62, No. 5, pp. 1094-1106, May 2013.
A. Mahajan, E. Lee, A. Callom-Moldovan, "Intraoperative Use of Forehead Reflectance Oximetry in Pediatric Patients," Anesth Analg, 98(S7):A20, 2004 (abstract).
P.D. Mannheimer, M.P. O'Neil, E. Konecny, "The Influence of Larger Subcutaneous Blood Vessels on Pulse Oximetry," J Clin Monit Comp, vol. 18, No. 3, pp. 179-188, 2004.
Masimo Corp., "Signal extraction technology," (2012). [Online]. Available: http://www.masimo.com/pdf/whitepaper/LAB1035R.PDF.
MIT-BIH Arrhythmia Database. (2013). [Online]. Available: www.physionet.org/physiobank/database/mitdb.
G.B. Moody, R.G. Mark, A.L. Goldberger, "PhysioNet: a Web-Based Resource for the Study of Physiologic Signals," IEEE Engineering in Medicine and Biology Magazine, vol. 20, No. 3, pp. 70-75, May-Jun. 2001.

L. Nilsson, A. Johansson, and S. Kalman, "Monitoring of Respiratory Rate in Postoperative Care Using a New Photoplethysmographic Technique," J. Clin. Monit., vol. 16, No. 4, pp. 309-315, 2000.
L. Nilsson, A. Johansson, S. Kalman, "Respiration Can be Monitored by Photoplethysmography with High Sensitivity and Specificity Regardless of Anaesthesia and Ventilatory Mode," Acta Anaesthesiol Scand, vol. 49. pp. 1157-1162, 2005.
M.R. Ram, K.V. Madhav, E.H. Krishna, N.R. Komalla, K.A. Reddy, "A Novel Approach for Motion Artifact Reduction in PPG Signals Based on AS-LMS Adaptive Filter," IEEE Transactions on Instrumentation and Measurement, pp. 1-13, 2011.
K.A. Reddy, B. George, N.M. Mohan, V.J. Kumar, "A Novel Calibration-Free Method of Measurement of Oxygen Saturation in Arterial Blood," IEEE Transactions on Instrumentation and Measurement, vol. 58, No. 5, pp. 1699-1705, May 2009.
D.T. Redford, S.J. Barker, R.R. Lichtenthal, "Evaluation of 2 Forehead Reflectance Oximeters in Intraoperative Surgical Patients," Anesth, 101:A593, 2004 (abstract).
P.S. Addison, J.N. Watson, "Secondary Wavelet Feature Decoupling (SWFD) and its Use in Detecting Patient Respiration from the Photoplethysmogram," Engineering in Medicine and Biology Society, 2003. Proceedings of the 25th Annual International Conference of the IEEE, vol. 3, pp. 2602-2605, Sep. 17-21, 2003.
G.S. Agashe, J. Coakley, P.D. Mannheimer, "Forehead Pulse Oximetry: Headband Use Helps Alleviate False Low Readings Likely Related to Venous Pulsation Artifact," Journal of Anesthesiology, vol. 105, No. 6, pp. 1111-1116, Dec. 2006.
H.H. Asada, H. Jiang, and P. Gibbs, "Active Noise Cancellation using MEMS Accelerometers for Motion-Tolerant Wearable Bio-Sensors," in Proc. Conf. IEEE Eng. Med. Biol. Soc., vol. 1, pp. 2157-2160, 2004.
H.H. Asada, P. Shaltis, A. Reisner, S. Rhee, R.C. Hutchinson, "Mobile Monitoring with Wearable Photoplethysmographic Biosensors," IEEE Engineering in Medicine and Biology Magazine, vol. 22, No. 3, pp. 28-40, May-Jun. 2003.
T. Aoyagi, M. Fuse, N. Kobayashi, K. Machida, K. Miyasaka, "Multiwavelength Pulse Oximetry: Theory for the Future," Anesth Analg., vol. 105, No. 6, 2007.
T. Aoyagi, K. Miyasaka, Pulse Oximetry: Its Invention, Contribution to Medicine, and Future Tasks, Anesth. Analg., vol. 94, pp. 51-53, 2002.
T. Aoyagi, "Pulse Oximetry: Its Invention, Theory, and Future," Journal of Anesthesia, vol. 17, No. 4, pp. 259-266, Jul. 2003.
A. Awad, M.A. Ghobashy, R.G. Stout, D.G. Silverman, K.H. Shelley, "How Does the Plethysmogram Derived from the Pulse Oximeter Relate to Arterial Blood Pressure in Coronary Artery Bypass Graft Patients?," Anesth Analg, vol. 93, pp. 1466-1471.
A.K. Barros, A. Cichocki, "Extraction of Specific Signals with Temporal Structure," Neural Computation, vol. 13, No. 9, pp. 1995-2003, 2001.
A.K. Barros, N. Ohnishi, "Heart Instantaneous Frequency (HIF): an Alternative Approach to Extract Heart Rate Variability," IEEE Trans. On Bio. Eng., vol. 48, No. 8, pp. 850-855, Aug. 2001.
A. Belouchrani, A. Abed-Meraim, J.F. Cardoso, E. Moulines, "A Blind Source Separation Technique Using Second-Order Statistics," IEEE Transactions on Signal Processing, vol. 45, No. 2, pp. 434-444, Feb. 1997.
V.F. Blanc, M. Haig, M. Troli, B. Sauve, "Computerized Photoplethysmography of the Finger," Can J Anaesth, vol. 40, pp. 271-278, 1993.
B. Bohnhorst, C.F. Poets, "Major Reduction in Alarm Frequency with a New Pulse Oximeter," Intensive Care Med, vol. 24, pp. 277-278, 1998.
P. Bonato, D. De Rossi, A. Dittmar, S. Jayaraman, I. Korhonen, A. Lymberis, E. Mc Adams, Y. Zhang, "IEEE EMBS Technical Committee on Wearable Biomedical Sensors and Systems: Position Paper," BSN, pp. 212-214, 2006.
R. D. Branson, P.D. Mannheimer, "Forehead Oximetry in Critically ill Patients: The Case for a New Monitoring Site," Respir Care Clin N Am, vol. 10, pp. 359-367, 2004.
R.T. Brouillette, J. Lavergne, A. Leimanis, G.M. Nixon, S. Ladan, C.D. McGregor, "Differences in Pulse Oximetry Technology can

(56) References Cited

OTHER PUBLICATIONS

Affect Detection of Sleep-Disordered Breathing in Children," Anesth Analg vol. 94, pp. 47-53, 2002.
A. Casati, G. Squicciarini, M. Baciarello, M. Putzu, A. Salvadori, G. Fanelli, "Forehead Reflectance Oximetry: A Clinical Comparison with Conventional Digit Sensors during Laparotomic and Laparoscopic Abdominal Surgery," Journal of Clinical Monitoring and Computing, vol. 21, No. 5, pp. 271-276, 2007.
N.I. Cho, S.U. Lee, "Tracking Analysis of an Adaptive Lattice Notch Filter," IEEE Trans. on Circuits and Systems—II: Analog and Digital Signal Processing, vol. 42, No. 3, pp. 186-195, Mar. 1995.
K.H. Chon, S. Dash, and K. Ju, "Estimation of Respiratory Rate from Photoplethysmogram Data Using Time-Frequency Spectral Estimation," IEEE Trans. Biomed. Eng., vol. 56, No. 8, 2054-2063, Aug. 2009.
G. Cloete, P.R. Fourie, C. Scheffer, "Development and Testing of an Artificial Arterial and Venous Pulse Oximeter," 35th Annual International Conference of the IEEE Engineering in Medicine and Biology Society, pp. 1042-4045, Jul. 2013.
J.E. Cooke, J.E. Scharf, "Forehead Pulse Oximetry in the Trendelenburg Position," Anesthesiology,vol. 101, pp. A-583, 2004.
S. Dash, K.H. Shelley, D.G. Silverman, and K.H. Chon, "Estimation of Respiratory Rate from ECG, Photoplethysmogram, and Piezoelectric Pulse Transducer Signals: A Comparative Study of Time-Frequency Methods," IEEE Trans. Biomed. Eng., vol. 57, No. 5, pp. 1099-1107, May 2010.
J.C. Dorlas, J.A. Nijboer, "Photo-Electric Plethysmography as a Monitoring Device in Anaesthesia. Application and interpretation," Br J Anaesth, vol. 57, pp. 524-530, 1985.
C.G. Durbin, S.K. Rostow, "More Reliable Oximetry Reduces the Frequency of Arterial Blood Gas Analyses and Hastens Oxygen Weaning after Cardiac Surgery: a Prospective, Randomized Trial of the Clinical Impact of a New Technology," Crit Care Med, vol. 30, pp. 1735-1740, 2002.
A.S. Echiadis, V.P. Crabtree, J. Bence, L. Hadjinikolaou, C. Alexiou, T.J. Spyt, S. Hu, "Non-Invasive Measurement of Peripheral Venous Oxygen Saturation Using a New Venous Oximetry Method: Evaluation During Bypass in Heart Surgery," Physiological Measurement, vol. 28, No. 8, pp. 897-911, 2007.
S. Elliott, P. Darlington, "Adaptive Cancellation of Periodic, Synchronously Sampled Interference," IEEE Trans. on Acoustics, Speech and Signal Processing, vol. 33, No. 3, pp. 715-717, Jun. 1985.
M. Fernandez, K. Burns, B. Calhoun, S. George, B. Martin, C. Weaver, "Evaluation of a New Pulse Oximeter Sensor," Am J Crit Care., vol. 16, No. 2, pp. 146-152, 2004.
Food and Drug Administration, "Pulse Oximeters-Premarket Notification Submissions [510(k)s] Guidance for Industry and Food and Drug Administration Staff," Mar. 2013.
J.M. Goldman, M.T. Petterson, R.J. Kopotic, S.J. Barker, "Masimo Signal Extraction Pulse Oximetry," J Clin. Monit, vol. 16, pp. 475-483, 2000.
J.M. Graybeal, M.T. Petterson, "Adaptive Filtering and Alternative Calculations Revolutionizes Pulse Oximetry Sensitivity and Specificity During Motion and Low Perfusion," EMBC vol. 7, pp. 5363-5366, 2004.
H. Han, M.J. Kim, J. Kim, "Development of Real-Time Motion Artifact Reduction Algorithm for a Wearable Photoplethysmography," in Proc. Conf. IEEE Eng. Med. Biol. Soc., pp. 1538-1541, 2007.
J.A. Hirsch , B. Bishop, "Respiratory Sinus Arrhythmia in Humans: How Breathing Pattern Modulates Heart Rate," Am J Physiol., vol. 241, No. 4, pp. 620-629, 1981.

International Organization for Standardization, "Particular Requirements for Basic Safety and Essential Performance of Pulse Oximeter Equipment," 2011.
B. Jönsson, C. Lauren, T. Skau, L.G. Lindberg, "A New Probe for Ankle Systolic Pressure Measurement Using Photoplethysmography (ppg)," Ann Biomed Engl, vol. 33, pp. 232-239, 2005.
S.H. Kim, D.W. Ryoo, and C. Bae, "Adaptive Noise Cancellation Using Accelerometers for the PPG Signal from Forehead," in Proc. Conf. IEEE Eng. Med. Biol. Soc., pp. 2564-2567, 2007.
J. Lee and K.H. Chon, "An Autoregressive Model-Based Particle Filtering Algorithms for Extraction of Respiratory Rates as High as 90 Breaths Per Minute from Pulse Oximeter," IEEE Trans. Biomed. Eng., vol. 57, No. 9, pp. 2158-2167, Sep. 2010.
H.M. Sami, B.S. Kleinman, V.A. Lonchyna, "Central Venous Pulsations Associated with a Falsely Low Oxygen Saturation Measured by Pulse Oximetry," Journal of Clinical Monitoring, vol. 7, No. 4. pp. 309-312, 1991.
P. Shaltis, H.H. Asada, "Monitoring of Venous Oxygen Saturation Using a Novel Vibratory Oximetry Sensor," Proceedings of the Second Joint 24th Annual Conference Engineering in Medicine and 24 Biology and the Annual Fall Meeting of the Biomedical Engineering Society, vol. 2, pp. 1722-1723, Oct. 2002.
K.H. Shelley, "Photoplethysmography: Beyond the Calculation of Arterial Oxygen Saturation and Heart Rate," Anesth Analg, vol. 105, No. 6, Dec. 2007.
K.H. Shelley, M. Dickstein, S.M. Shulman, "The Detection of Peripheral Venous Pulsation Using the Pulse Oximeter as a Plethysmograph," Journal of Clinical Monitoring, vol. 9, No. 4, pp. 283-287, 1993.
K.H. Shelley, D. Tamai, D. Jablonka, M. Gesquiere, R.G. Stout, D. G. Silverman, "The Effect of Venous Pulsation on the Forehead Pulse Oximeter Wave Form as a Possible Source of Error in SpO2 Calculation," Journal of Anesth Analg, vol. 100, pp. 743-747, 2005.
J.E. Sinex, "Pulse Oximetry: Principles and Limitations," Amer. J. Emergency Med., vol. 17, No. 1, pp. 59-68, Jan. 1999.
H.A. Smithline, N. Rudnitzky, S. Macomber, F.S.J. Blank, "Pulse Oximetry Using a Disposable Finger Sensor Placed on the Forehead in Hypoxic Patients," The Journal of Emergency Medicine, vol. 39, No. 1, pp. 121-125, 2010.
Texas Instrument Inc., http://www.ti.com/tool/tmdxevm5515.
M. Wax, J. Sheinvald, "A Least-Squares Approach to Joint Diagonalization," IEEE Signal Processing Letters, vol. 4, No. 2, pp. 52-53, Feb. 1997.
J. G. Webster, Design of Pulse Oximeters, New York: Taylor & Francis, 1997, Chapter 4, Light Absorbance n Pulse Dxymetry, Oliver Wieben, pp. 40-41.
R.A. Whitman, M.E. Garrison, T.J. Oestreich, M.S. Musumbi, "Evaluation of a New Reflectance Forehead Sensor in Detecting Oxygen Desaturation in Patients Undergoing Polysomnography," Anesthesiology, 99:A553, 2003 (abstract).
J.D. Wise, J.R. Caprio, T.W. Parks, "Maximum Likelihood Pitch Estimation," IEEE Trans. Acoust., Speech, Signal Processing, vol. 24, pp. 418-423, Oct. 1976.
L.B. Wood and H. Asada, "Low Variance Adaptive Filter for Cancelling Motion Artifact in Wearable Photoplethysmogram Sensor Signals," in Proc. Conf. IEEE Eng. Med. Biol. Soc., pp. 652-655, 2007.
M.M. Wood, L.E. Romine, Y.K. Lee, K.M. Richman, M.K. O'Boyle, D.A. Paz, P.K. Chu, D.H. Pretorius, "Spectral Doppler Signature Waveforms in Ultrasonography: A Review of Normal and Abnormal Waveforms," Ultrasound Q., vol. 26, No. 2, pp. 83-99, 2010.
J.Y.A. Foo and S.J. Wilson, "Estimation of Breathing Interval from the Photoplethysmographic Signals in Children," Physiol. Meas., vol. 26, No. 6, pp. 1049-1058, Dec. 2005.

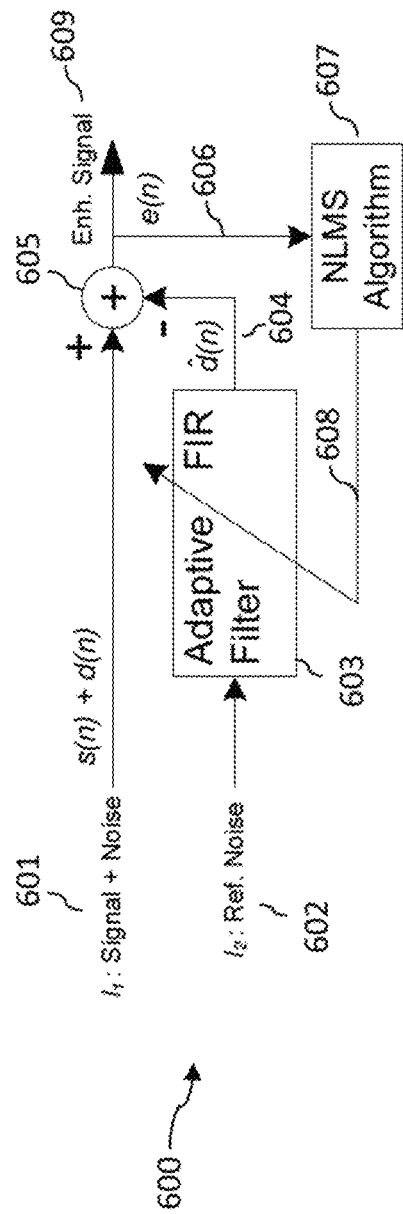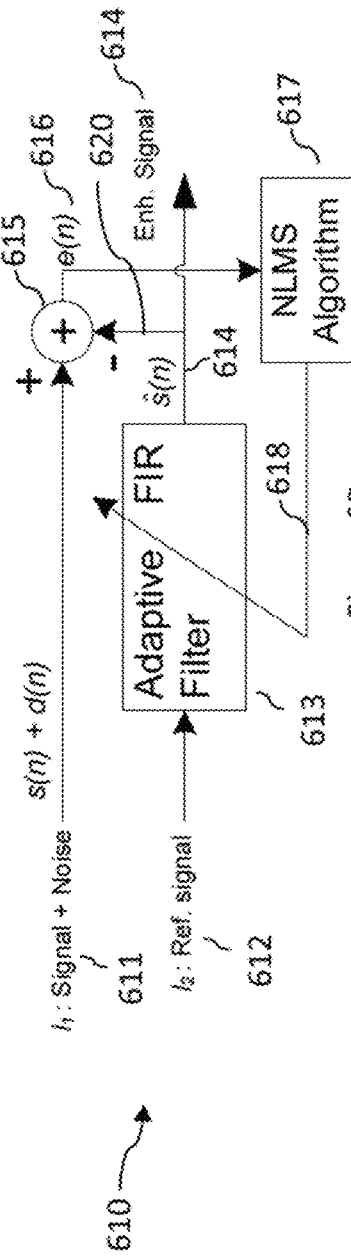

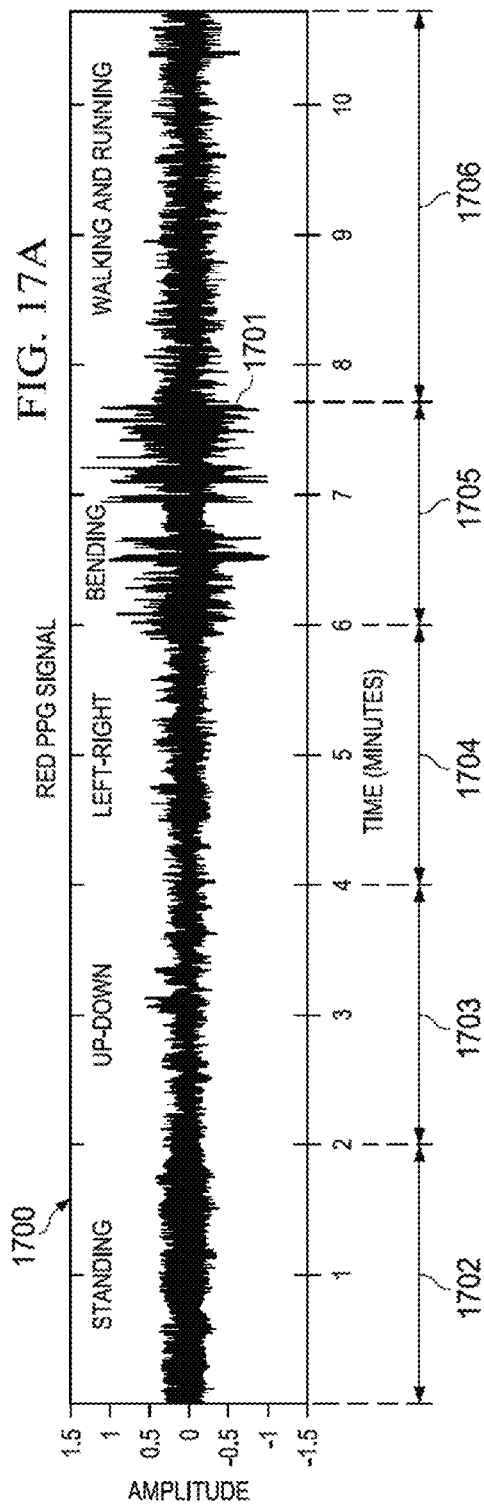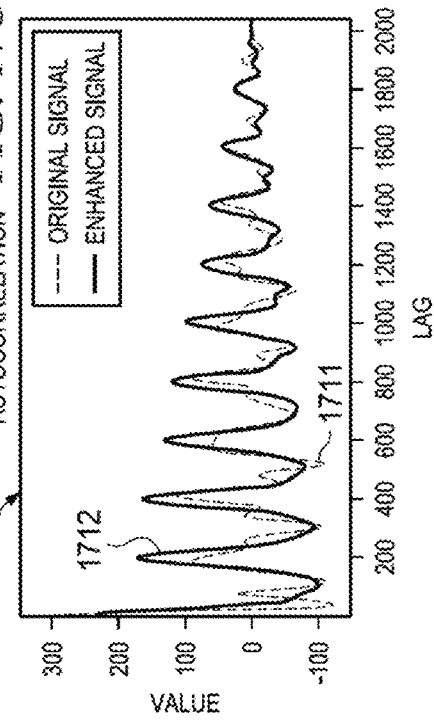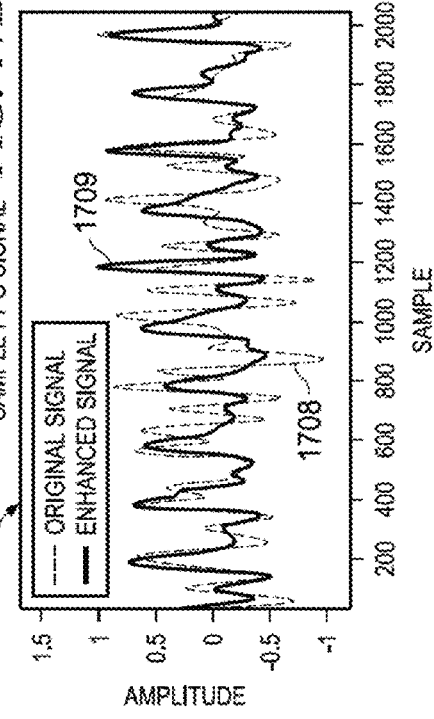

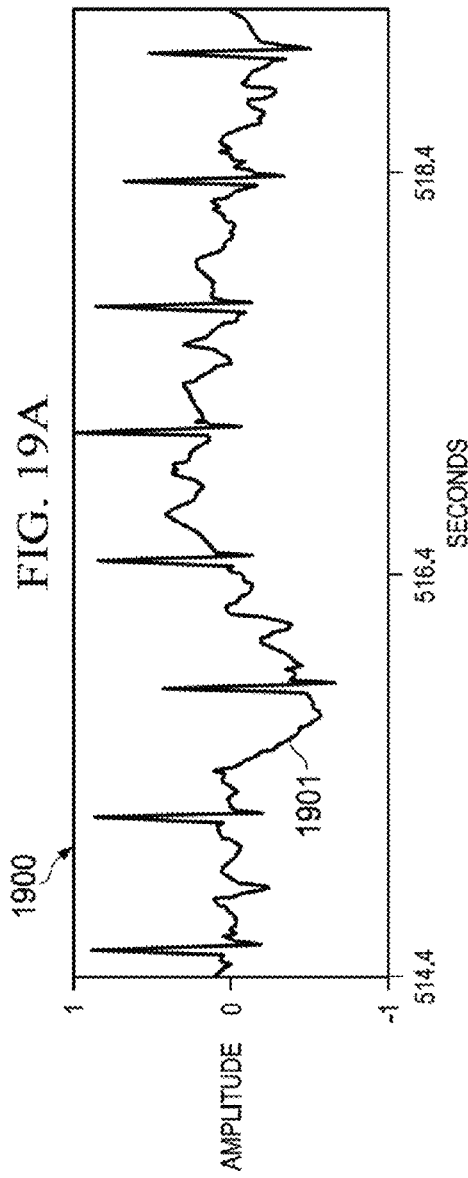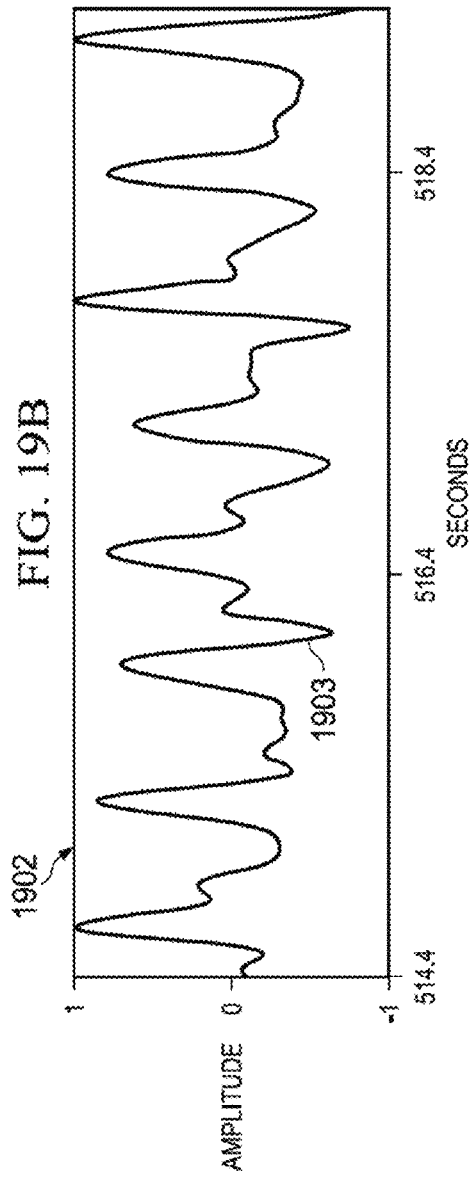

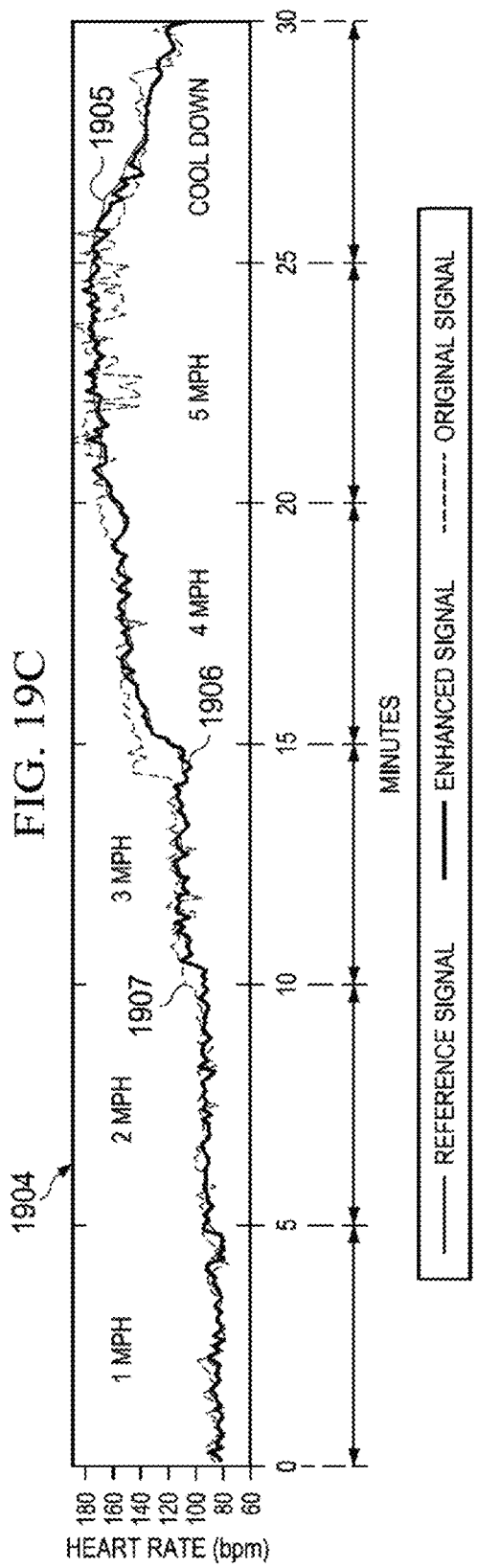

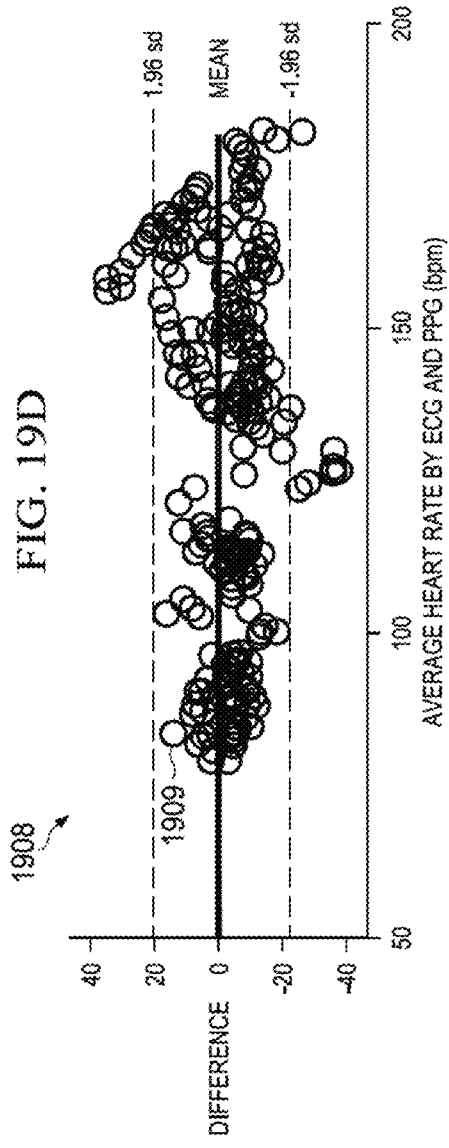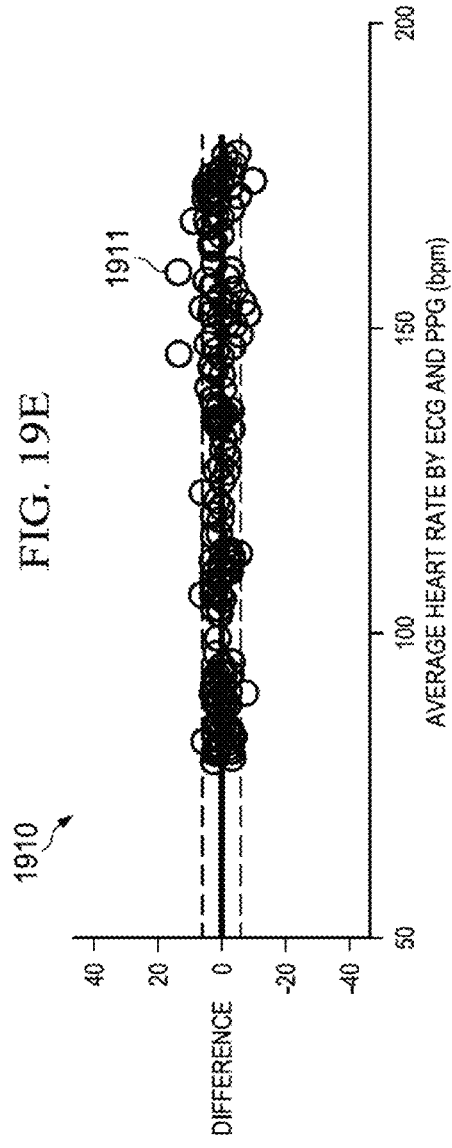

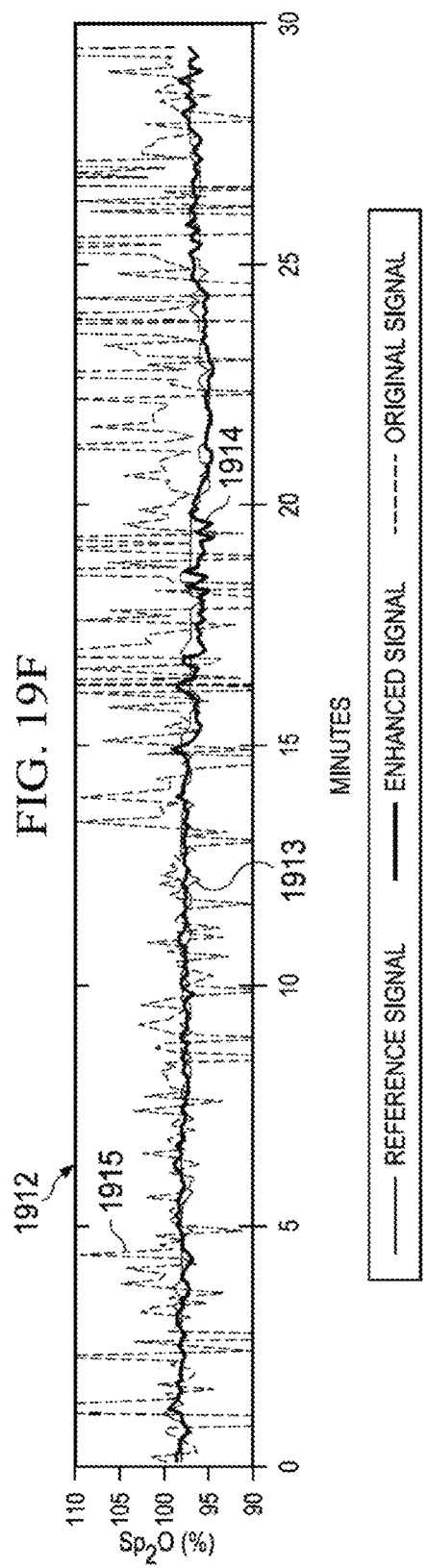

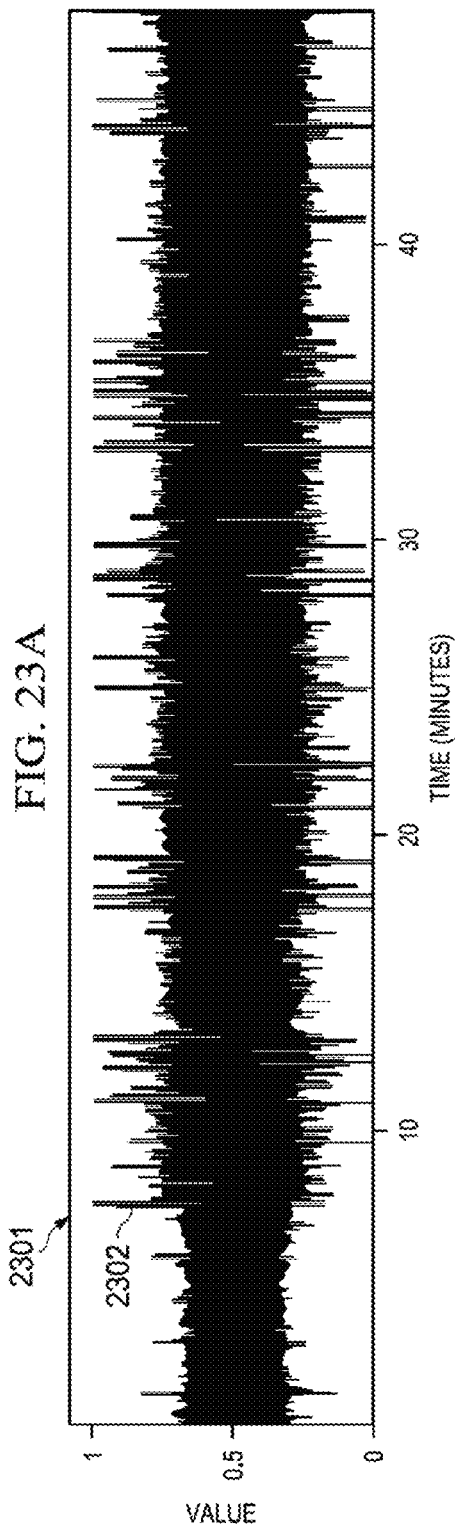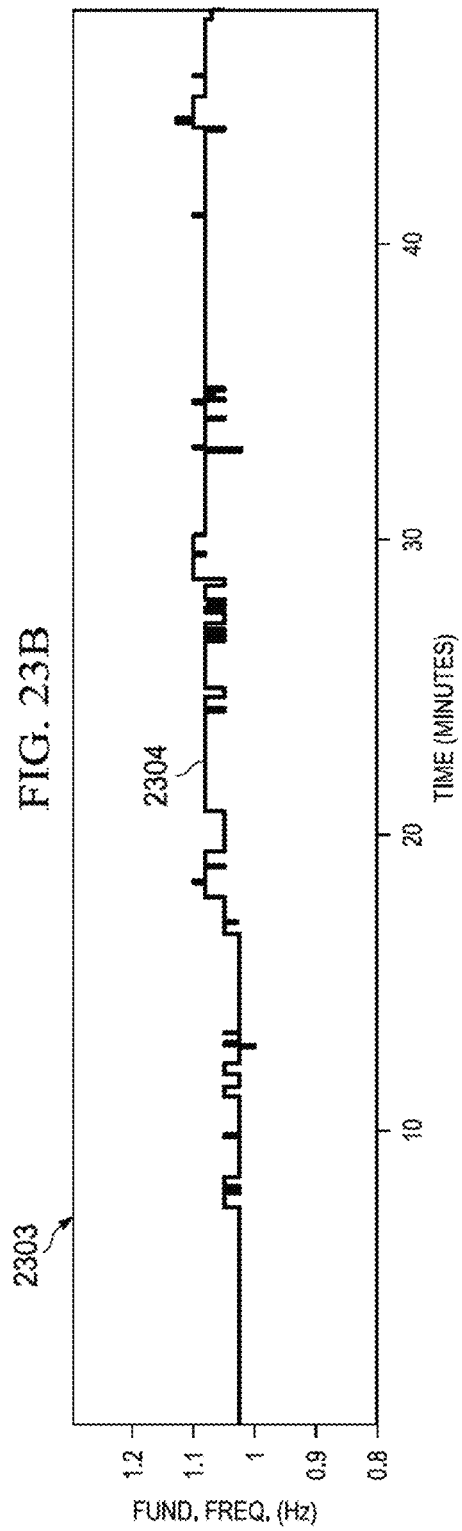

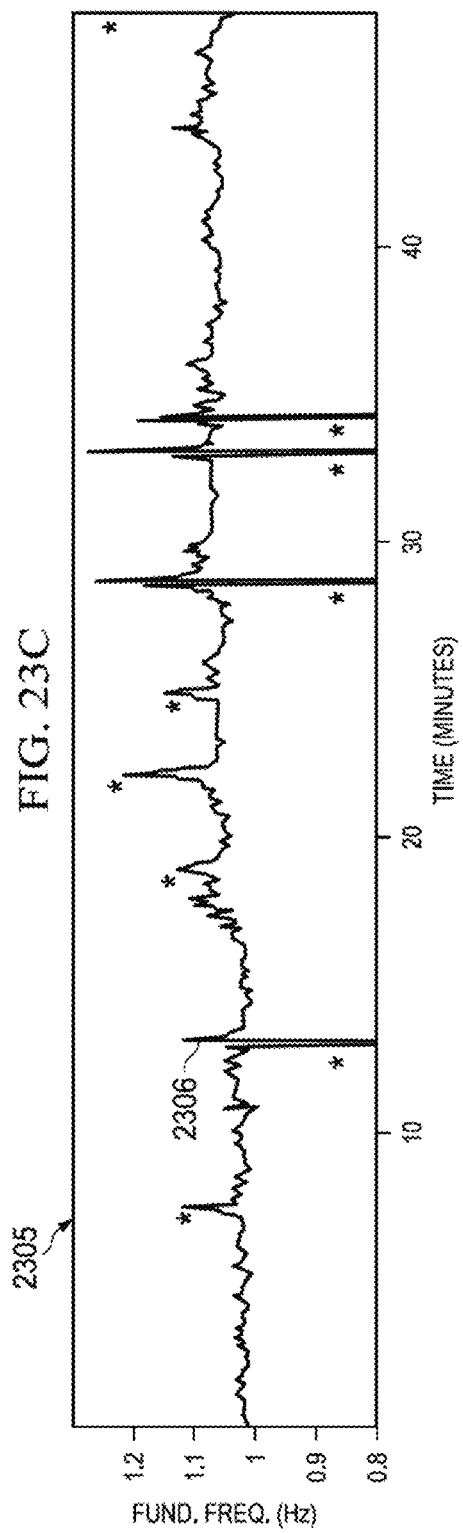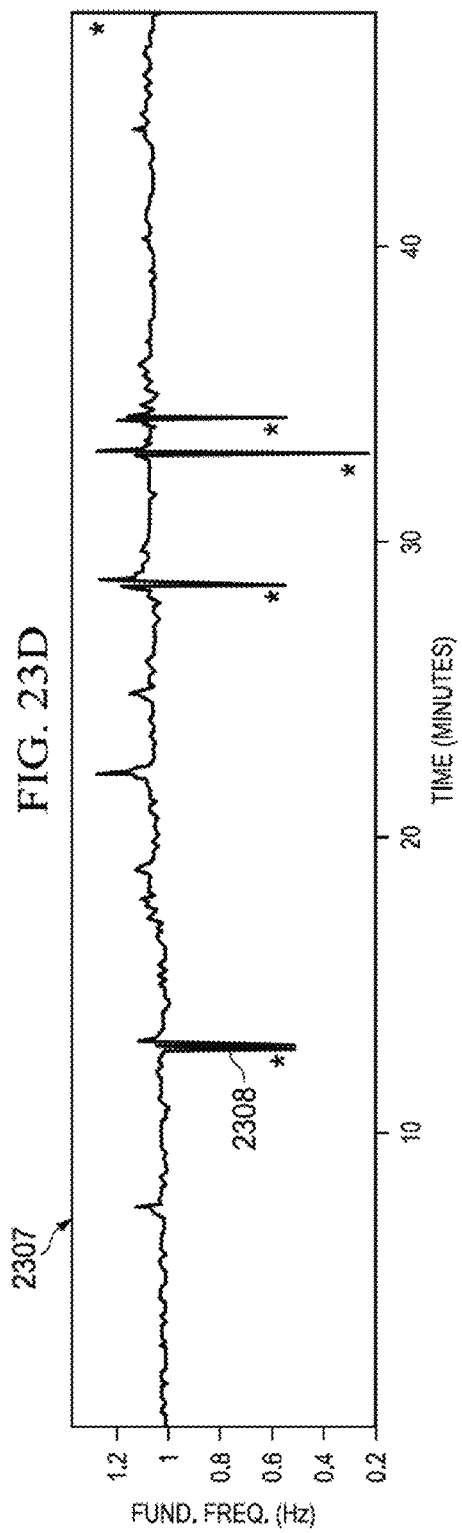

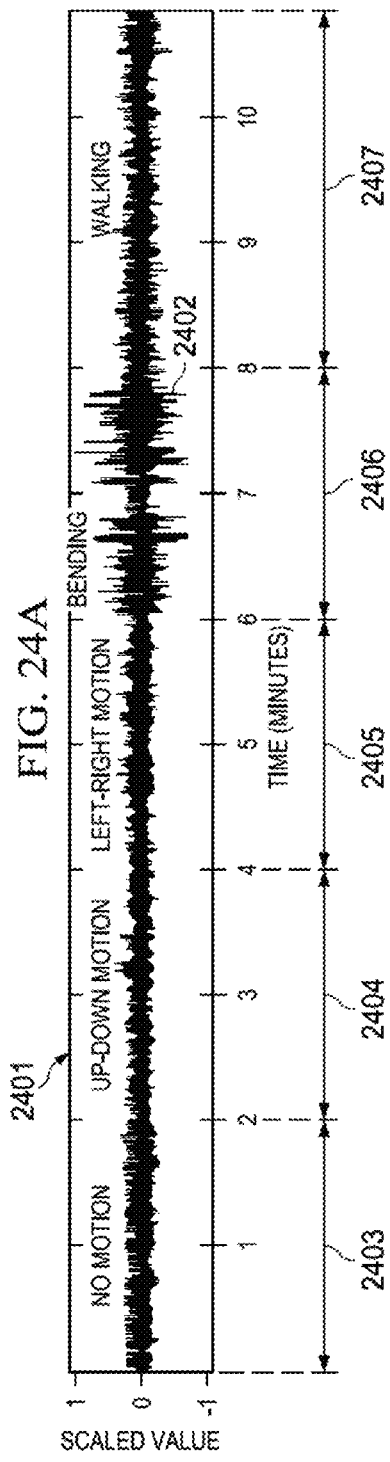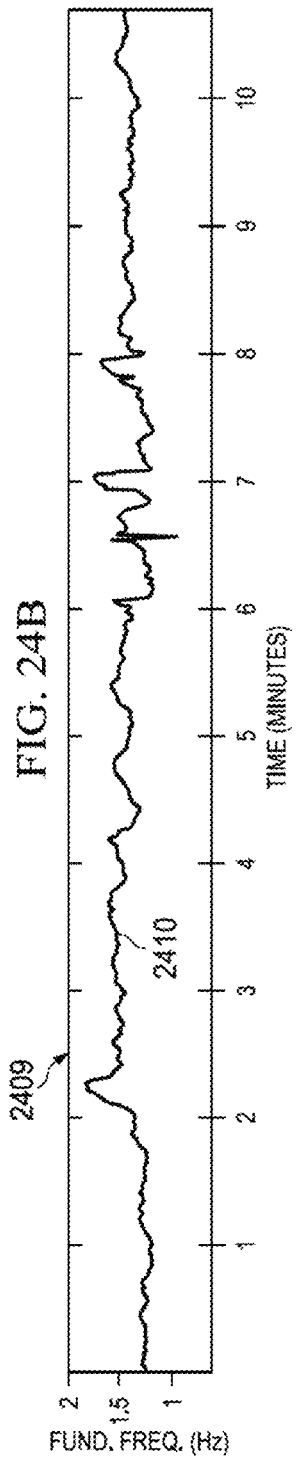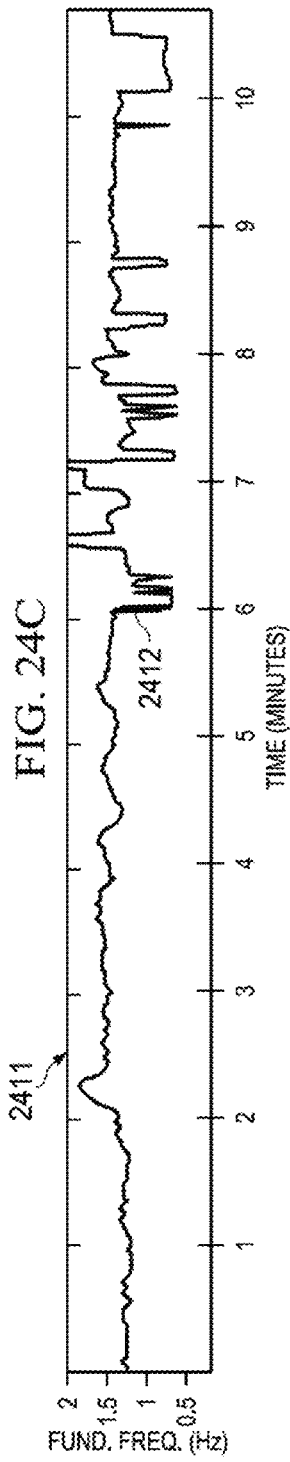

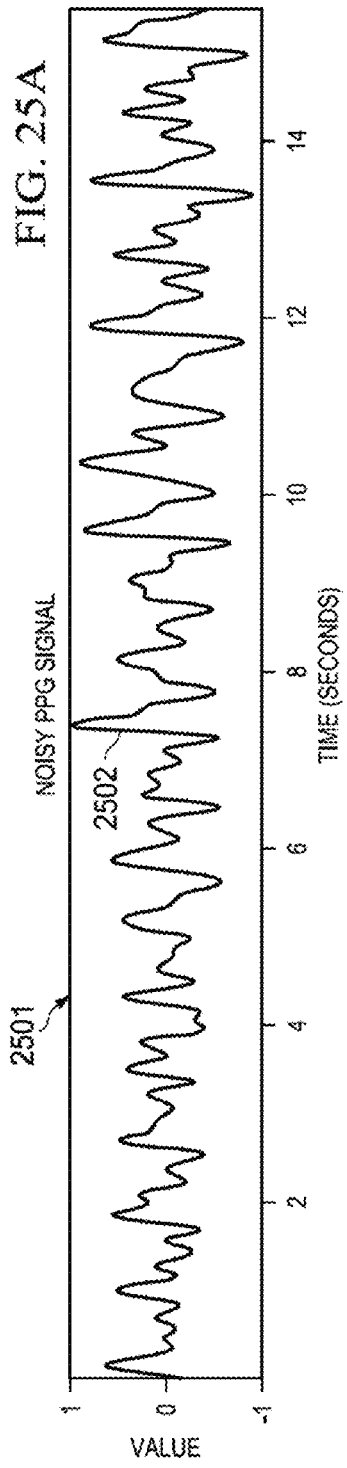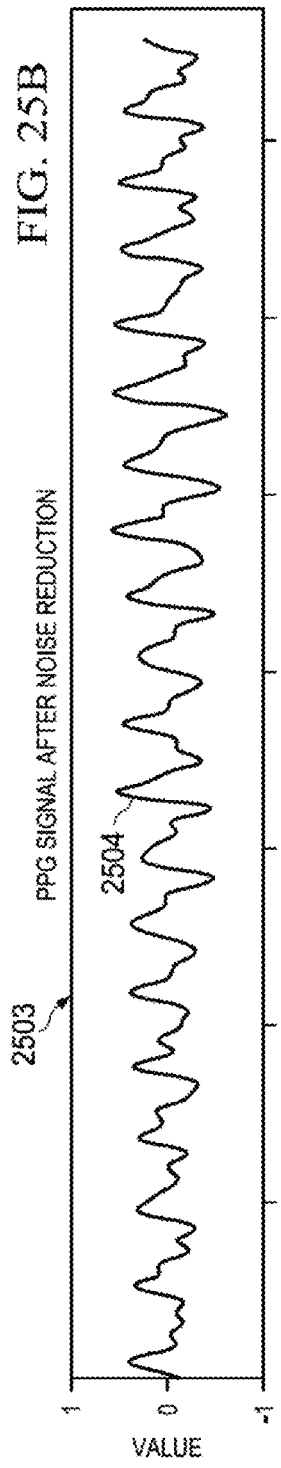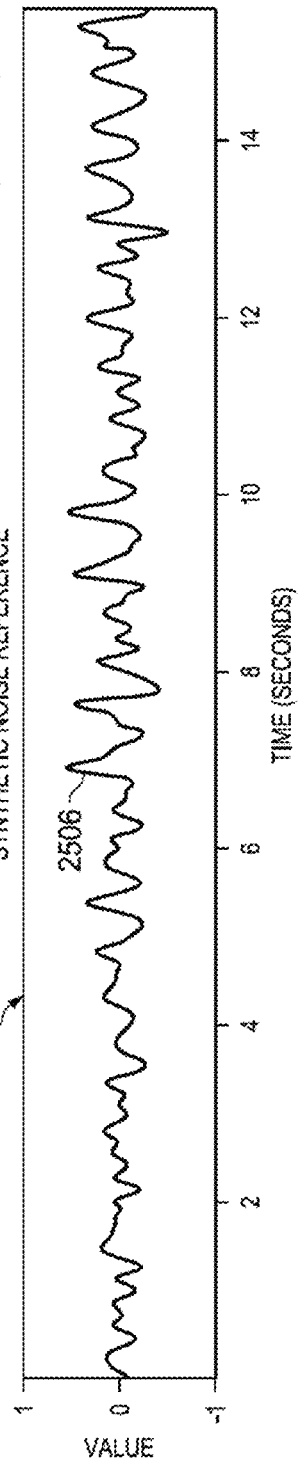

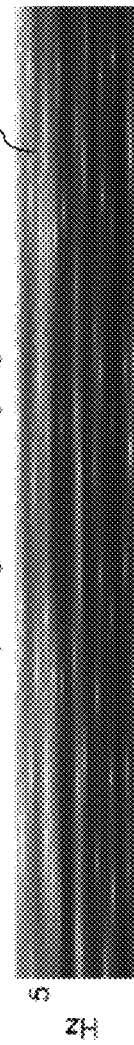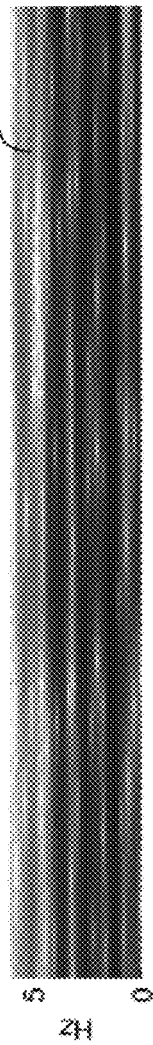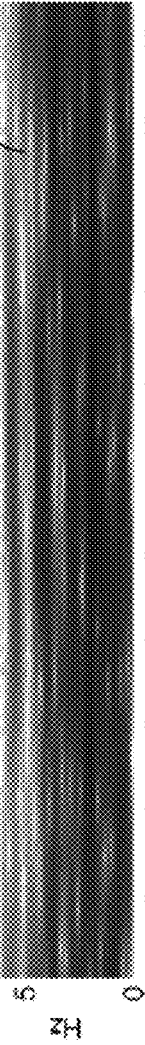

SYSTEMS AND METHODS FOR PHYSIOLOGICAL SIGNAL ENHANCEMENT AND BIOMETRIC EXTRACTION USING NON-INVASIVE OPTICAL SENSORS

CROSS REFERENCE TO RELATED APPLICATION

This application claims priority to U.S. Provisional Application No. 61/926,773 filed Jan. 13, 2014. The above identified patent application is incorporated herein by reference in its entirety to provide continuity of disclosure.

FIELD OF THE INVENTION

The present invention relates to systems and methods for enhancing physiological signals taken by optical biosensors at different human body sites. In particular, the present invention relates to enhancing photoplethysmographic signals for pulse oximetry, extraction of heart rate, and extraction of other physiological parameters such as respiratory information, fluid responsiveness, perfusion level and other hemodynamic parameters.

BACKGROUND

Photoplethysmography is a non-invasive measurement of the blood flow at the surface of the skin of a human by using two-wavelength lights, such as red (R) and infrared (IR) lights, to generate photoplethysmographic ("PPG") signals. Two common uses of the PPG signals are calculations of the arterial oxygen saturation and heart rate. Several applications that require various analyses of the PPG signals include amplitude, rhythm, peripheral pulse, respiratory variability and tissue perfusion. For example, increased and decreased signal amplitude can indicate signs of vasodilation and vasoconstriction, respectively. The amplitude is directly proportional to the vascular distensibility. PPG signals are also useful for the detection and diagnosis of cardiac arrhythmias. Further, a PPG signal is known to be sensitive to pulsatile blood flow and captures the peripheral pulses. The pressure at which the pulse is captured highly corresponds to the systolic blood pressure. The respiratory rate can be determined by a set of PPG signals. Noninvasive continuous tissue perfusion and peripheral blood flow detection is another potential advantage of the PPG signal. All the above-mentioned applications require a clean and enhanced signal for feature extraction, analysis, and monitoring. Therefore, the quality of the PPG signal is critical for wearable PPG devices and systems.

For example, in wearable and implantable devices/applications, biometric signals need to be monitored during daily activities where motion is always present. Motion artifact is the most problematic source of noise which deteriorates signal integrity and can, in the worst case, corrupt the PPG signal to such an extent that the signal is rendered clinically unusable. Examples of motions of the patient in a real world clinical setting include movement during transport, rubbing, waving, seizures, and kicking in neonates and infants. As a result, inaccurate readings and interpretations of the PPG signal due to motion artifact increases the workload of a caregiver of the patient which leads to an increased cost of care and inefficiency of patient's treatment. Therefore, there is a need in the art for an effective solution for wearable and mobile PPG biosensors to enhance the signal quality in the presence of motion artifact.

The prior art has attempted to solve these problems with limited success. For example, one commonly used method to reduce the effect of motion artifact is adaptive noise cancellation using accelerometers as a noise reference signal. A two-dimensional active noise cancellation uses the directional accelerometer data for a finger PPG sensor. Another method adds a reflectance PPG sensor as the reference signal to reduce the effect of motion artifact. However, the reflectance PPG sensor is itself susceptible to motion artifact. The main drawback of all these methods is the cost of extra hardware for the generation of the noise reference signal. Further, using accelerometer data is computationally intensive and reflects motion as opposed to motion-induced noise. More precisely, no direct or high correlation between acceleration data from an accelerometer and motion artifact in PPG signal has been found. This method assumes that the original PPG signal has only power at certain frequencies with the remaining power assumed to be noise and then uses Fast Fourier Transform (FFT), Singular Value Decomposition and Independent Component Analysis to generate three synthetic reference noise signals. The method switches between the three reference noise signals by quantifying the randomness of each signal using skewness and kurtosis. These assumptions on motion artifact do not correlate with different real-world sources of noise. Moreover, the highest randomness does not necessarily mean the highest correlation with the true motion artifact in the PPG signal.

In another example, Masimo Corporation has introduced Discrete Saturation Transform (DST) to find pulse oximeter oxygen saturation in the presence of motion in portable devices. Typically, the DST method includes of a reference signal generator, an adaptive filter and a peak finder to find the most likely $SpO_2$ value based on the incoming signals. In this approach, the reference signal generator produces reference signals for all possible $SpO_2$ values. For each reference signal, the adaptive filter produces an output signal. Energy of each output signal is computed and plotted versus corresponding $SpO_2$ values. The right-most peak of the power plot (the largest saturation value) is nominally considered as oxygen saturation of arterial blood flow. However, this approach does not remove the motion artifact (e.g. due to tissue effect). Consequently, the effect of motion artifact is transformed to the output power plot in DST. More specifically, in presence of motion artifact, new peaks will be present on the output plot and the peak finder fails to find the peak corresponding to accurate $SpO_2$. Alternatively, the peak corresponding to $SpO_2$ is concealed due to high motion noise power causing the peak search to fail for that time window.

Therefore, there is a need in the art for an effective solution for wearable and mobile PPG biosensors to enhance the signal quality in the presence of motion artifact.

SUMMARY

In a preferred embodiment, a system and method for enhancing PPG signals are disclosed. Different sources of motion-induced error in the PPG signals, which include red and infrared signals are identified, quantified and estimated. Enhanced red and infrared signals are produced by removing these sources of motion induced error. A novel multi-stage adaptive method that efficiently removes the effect of tissue and venous blood noise during motion is disclosed. This method extracts a fundamental period of the PPG signal, the heart rate, and the oxygen saturation level. The method produces a clean enhanced red and infrared PPG signal corresponding to the arterial blood flow.

In one embodiment, an adaptive and direct capturing of the motion artifact present in circulatory system, including physical motions, respiration and skeletal muscle pumps, and generating enhanced and artifact-free two-wavelength (e.g. R/IR) PPG signals is provided.

In another embodiment, separation and quantification of arterial and venous pulsations of multi wavelength PPG signals (e.g. R and IR) is provided.

In another embodiment, identification of biphasic cardiac cycle and sub-heart-beat time intervals where extraction of oxygen saturation and heart rate are minimally impacted by artifact and maximally impacted by the main biometric variation is provided.

In another embodiment, a method to produce a synthetic noise reference is disclosed. The technique also uses a method for estimating fundamental frequency and noise reference.

In another embodiment, a first method to enhance red and infrared PPG signals is provided and a method is disclosed to extract the heart rate value.

In another embodiment, a method to enhance red and infrared PPG signals is provided in combination with a cardiac gating method to extract the oxygen saturation value.

BRIEF DESCRIPTION OF THE DRAWINGS

The disclosed embodiments will be described with reference to the accompanying drawings.

FIG. 6A is a block diagram of an adaptive noise canceller with reference noise of a preferred embodiment.

FIG. 6B is a block diagram of an adaptive noise canceller with a reference signal of a preferred embodiment.

FIG. 17A is a graph of a raw red PPG signal during various motions of an experiment of a preferred embodiment.

FIG. 17B is a graph of a sample PPG signal during an experiment of a preferred embodiment.

FIG. 17C is a graph of an autocorrelation of a preferred embodiment.

FIG. 19A is a graph of an ECG waveform from a reference ECG sensor of a preferred embodiment.

FIG. 19B a sample PPG signal of a preferred embodiment.

FIG. 19C is a graph of heart rates calculated from an original signal and an enhanced signal.

FIG. 19D is a graph of a Bland-Altman plot of an original heart rate of a preferred embodiment FIG. 19E is a graph of a Bland-Altman plot of an enhanced heart rate of a preferred embodiment.

FIG. 19F is a graph of $SpO_2$ calculated from an original signal and an enhanced signal.

FIG. 23A is a graph of a simulated noisy PPG signal.

FIG. 23B is a graph of a fundamental frequency of a preferred embodiment.

FIG. 23C is a graph of a portion of an autocorrelation function.

FIG. 23D is a graph of an autocorrelation function.

FIG. 24A is a graph of an original PPG signal of a preferred embodiment.

FIG. 24B is a graph of a heart rate calculated by a fundamental frequency of a preferred embodiment.

FIG. 24C is a graph of an autocorrelation function.

FIG. 25A is a graph of a motion corrupted PPG signal.

FIG. 25B is a graph of an improved PPG signal from an adaptive filter of a preferred embodiment.

FIG. 25C is a graph of a synthetic noise reference in time domain of a preferred embodiment.

FIG. 26A is a spectrogram of a motion corrupted PPG signal.

FIG. 26B is a spectrogram of an improved PPG signal of a preferred embodiment.

FIG. 26C is a spectrogram of a synthetic noise reference of a preferred embodiment.

DETAILED DESCRIPTION

Figure 1:
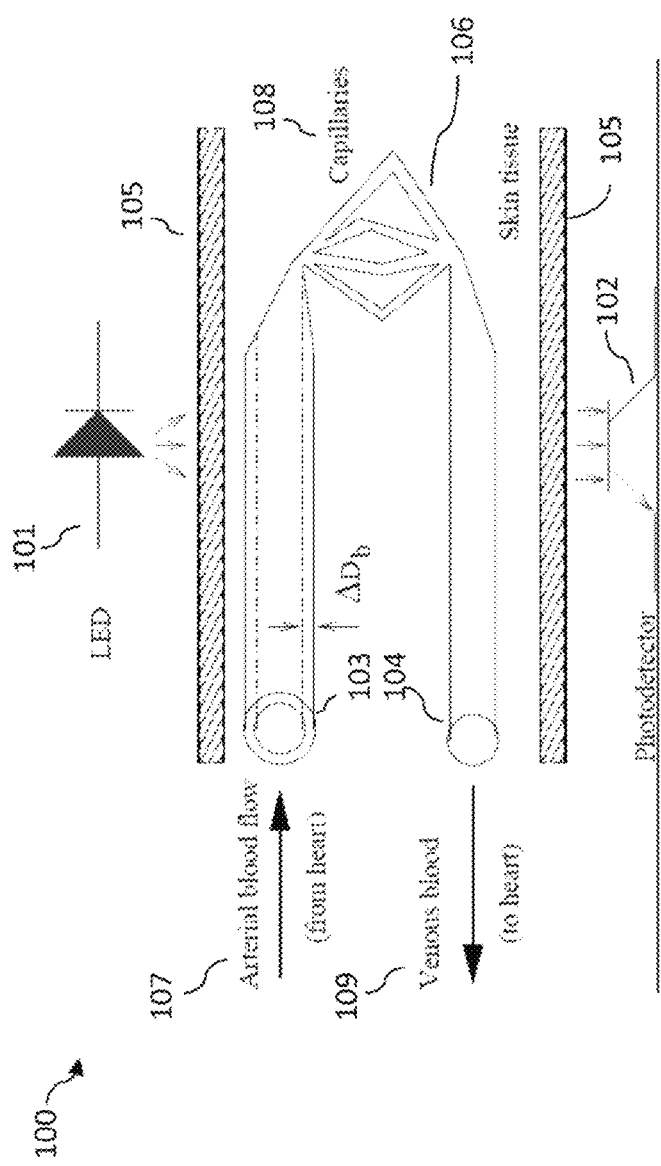
FIG. 1 is a general schematic of a PPG sensor and blood circulation at a measurement site.

It will be appreciated by those skilled in the art that aspects of the present disclosure may be illustrated and described in any of a number of patentable classes or contexts including any new and useful process or machine or any new and useful improvement. Aspects of the present disclosure may be implemented entirely in hardware, entirely in software (including firmware, resident software, micro-code, etc.) or combining software and hardware implementation that may all generally be referred to herein as a "circuit," "module," "unit", "block", "method", "model", "component," or "system." Further, aspects of the present disclosure may take the form of a computer program product embodied in one or more computer readable media having computer readable program code embodied thereon.

Any combination of one or more computer readable media may be utilized. The computer readable media may be a computer readable signal medium or a computer readable storage medium. For example, a computer readable storage medium may be, but not limited to, an electronic, magnetic, optical, electromagnetic, or semiconductor system, apparatus, or device, or any suitable combination of the foregoing. More specific examples of the computer readable storage medium would include, but are not limited to: a hard disk, a random access memory ("RAM"), a read-only memory ("ROM"), an erasable programmable read-only memory ("EPROM" or Flash memory), an appropriate optical fiber with a repeater, a portable compact disc read-only memory ("CD-ROM"), an optical storage device, a magnetic storage device, or any suitable combination of the foregoing. Thus, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. The propagated data signal may take any of a variety of forms, including, but not limited to, electromagnetic, optical, or any suitable combination of them. A computer readable signal medium may be any computer readable medium that is not a computer readable storage medium and that can communicate, propagate, or transport a program for use by or in connection with an instruction execution system, apparatus, or device.

Computer program code for carrying out operations for aspects of the present disclosure may be written in any combination of one or more programming languages, including an object oriented programming language such as Java, C++, C#, .NET, Objective C, Ruby, Python SQL, MATLAB, or other modern and commercially available programming languages.

One of the main applications of PPG biosensors is measuring blood oxygen saturation. The commercial device built based upon this technology is a pulse oximeter that uses two or more wave-length lights, such as red and infrared lights. Pulse oximetry may be used to quantify various blood flow characteristics including arterial oxygen saturation, the volume of blood pulsation carried to the tissues, and the heart rate.

Referring to FIG. 1, a pulse oximeter typically uses a set of light emitting diodes (LEDs) 101 with wavelengths in red and infrared regions which emit light at measurement site 100 on a human body. Photodetector 102 captures the transmitted or reflected light. The analog front-end hardware uses a time multiplexed approach with three phases: (i) an activated red LED phase, (ii) an activated infrared LED phase, and (iii) a dark phase. A transimpedance amplifier amplifies the current generated in the photodetector due to optical density during active phases and provides a voltage signal. The voltage signal is filtered, amplified, and sampled with an analog-to-digital converter for further processing.

The basic circulation of blood is conducted by the heart, which pumps blood periodically and rhythmically into a branching system of arteries. At measurement site 100 (e.g. finger, ear, forehead, nasal), tissues 105 and 106 slightly expand during each heart beat as arterial blood 107 enters capillaries 108 via arteries 103 during systole. The pulsations generated periodically by the heart will dampen by the time they reach capillaries 109, which are in contact with cells of tissues 105 and 106. Venous blood 109 then returns via veins 104 in an almost steady stream to the heart with another pulsation stimulated in veins 104 by muscular activity and the respiratory pump. Measurement site 100 contracts as venous blood 109 leaves during diastole. As a result, the path length of the light from the set of LEDs 101 will periodically change. Absorption is proportional to the optical path length according to the Lambert law of optical density and the volume change will be reflected in the output of photodetector 102. An electronic interface captures these changes via photodetector 102 on the measurement site 100 and provides the PPG signal having a set of component signals.

Figure 2:
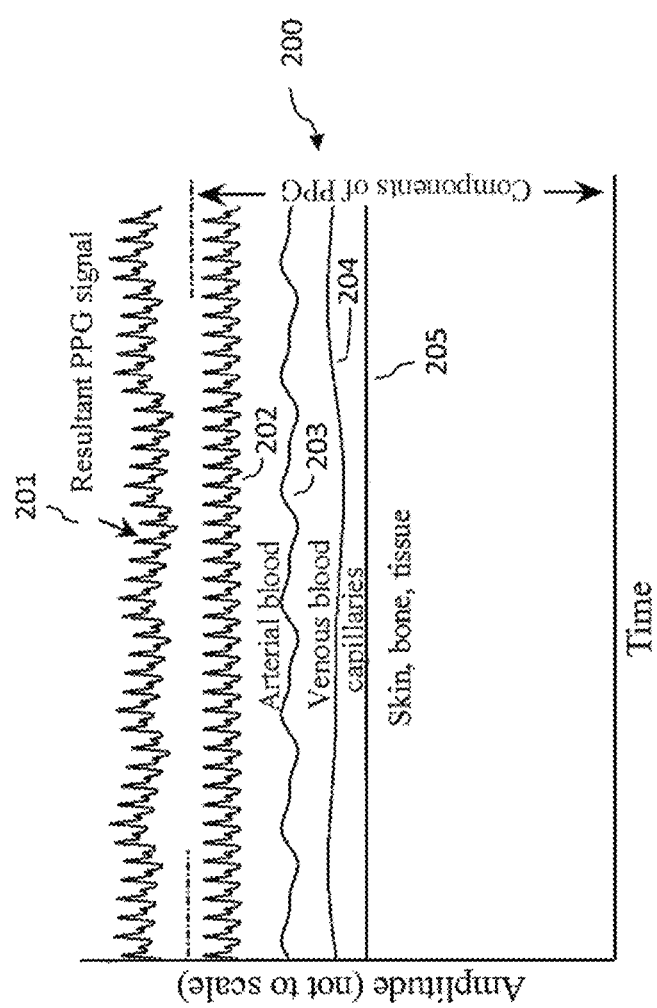
FIG. 2 is a graph of a PPG signal and components of the PPG signal.

Referring to FIG. 2, PPG signal 201 includes arterial blood component 202, venous blood component 203, capillary blood component 204, and skin, bone and tissue component 205.

Figure 3:
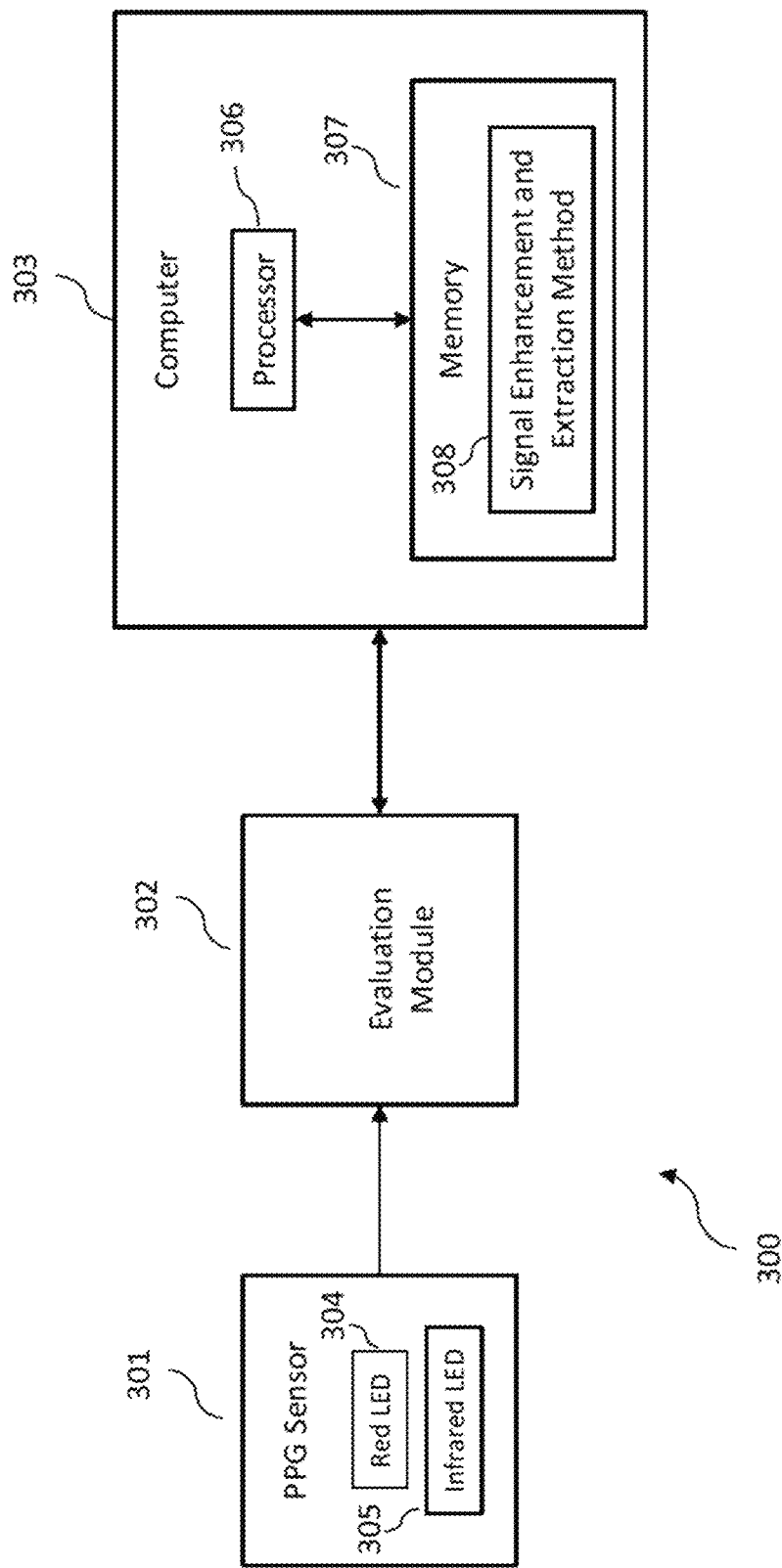
FIG. 3 is a schematic of a system for enhancing PPG signals in a preferred embodiment.

Referring to FIG. 3, system 300 includes PPG sensor 301 connected to evaluation module 302 and computing device 303 connected to evaluation model 302. PPG sensor 301 includes red LED 304 and infrared LED 305 and a photodetector. Computing device 303 includes processor 306 and memory 307 connected to processor 306. Signal enhancement and extraction method 308 is saved in memory 307 and is executed by processor 306. Evaluation module 302 includes a set of filters and computational units such as multipliers, as will be further described below. Evaluation module 302 receives a red signal from red LED 304 and an infrared signal from infrared LED 305. Evaluation module 302 processes the red signal and the infrared signal according to signal enhancement and extraction method 308, as will be further described below.

In one embodiment, computing device 303 is a personal computer. In another embodiment, computing device 303 is a tablet computer. In another embodiment, computing device 303 is a smartphone. Any computing device known in the art may be employed.

In one embodiment, computing device 303 is a wearable device, including a wrist-worn device or an electronic patch. In this embodiment, processor 306 and memory 307 are embedded. Any wearable computing device known in the art may be employed.

In a preferred embodiment, sensor 301 is a wearable sensor that uses red and infrared LEDs working at 660 nm and 895 nm, respectively. Any pulse oximetry sensor known in the art may be employed. Other sensors on various locations of the body and reflection or transmission mode sensors may be employed.

In a preferred embodiment, evaluation module 302 is an analog front end circuit with an onboard processor. Any evaluation module known in the art may be employed or a custom printed circuit board with custom analog front end may be employed for different applications. The evaluation module includes an analog conditioning circuit which limits the bandwidth of the PPG signal to 70 Hz. In one embodiment, a hamming window and a low-pass filter, with cutoff frequency at 8 Hz, are implemented on the evaluation module in order to attenuate any unwanted signals.

The source of the PPG signal, red or infrared, is the optical density transmitted or reflected. The basis of optical absorption is defined by Lambert-Beer's law that explains the optical density (A) for both scatterer and nonscatterer as:

$$A \triangleq \log\left(\frac{L_{in}}{L_{out}}\right) = E \cdot C \cdot D \quad \text{Eq. 1}$$

where $L_{in}$ and $L_{out}$ are incident and transmitted light intensities, respectively, and C and D are the concentration and thickness of the optical absorber, respectively. E is an extinction coefficient which is intrinsic to the absorber and wavelength. The assumption in this formulation is that the object is uniform and nonscattering and so it only provides a rough estimation about scatterers.

Two basic theories of optical scattering, which gives a more precise prediction of scattering behaviors, are Rayleigh-Mie's theory and Schuster's theory. Aoyagi who reported the principle of pulse oximetry in 1974 has adopted the Schuster's theory and introduced the optical theory behind photoplethysmography. The following relationship describes the optical density changes $\Delta A$ as a function of blood vessel thickness changes $\Delta D_b$ for a given blood vessel:

$$\Delta A = [\sqrt{E_h(E_h + F)} Hb + Z_b] \Delta D_b \quad \text{Eq. 2}$$

where $E_h \triangleq S\, E_O + (1-S) E_r$, in which $E_o$ and $E_r$ are the extinction coefficient of oxyhemoglobin and deoxyhemoglobin, respectively. S is oxygen saturation, Hb is hemoglobin concentrations of the blood and F is the scattering coefficient. $Z_b$ is a constant which becomes zero when the optical receiver is wide enough and independent of the working wavelength. Tissue effect is one of the main sources of error in obtained optical density leading to undesired fluctuation in acquired PPG signals. Considering the effect of tissues, Eq. 2 is modified by adding a new term $(Z_t\, \Delta D_t)$ and becomes:

$$\Delta A = \sqrt{E_h(E_h + F)} Hb \Delta D_b + Z_b \Delta D_b + Z_t \Delta D_t \quad \text{Eq. 3}$$

where $Z_t$ is approximated to be a constant independent of the wavelength and $\Delta D_t$ is thickness change of the tissue. Therefore, there is an optical density change (e.g. $Z_b\, \Delta D_b + Z_t\, \Delta D_t$) which is wavelength-independent. Eq. 3 considers only one blood vessel. Considering the effect of arterial blood vessels and venous blood vessels, there are arterial blood changes and venous blood changes. Therefore, $\Delta A$ is expressed as:

$$\Delta A = \sqrt{E_h(E_h + F)} Hb_a \Delta D_a + \sqrt{E_v(E_v + F)} Hb_v \Delta D_v + \Delta A_s \quad \text{Eq. 4}$$

Subscripts a and v refer to arterial blood and venous blood, respectively. $\Delta D_v$ and $\Delta D_a$ are venous and arterial blood thickness changes, respectively. $\Delta A_s$ is independent of wavelength and it captures the accumulated wavelength-independent effect of blood and tissue thickness changes. $Hb_a$ and $Hb_v$ are arterial and venous hemoglobin concentrations, respectively.

As will be described below, an optical density is formulated to define a reference signal and a reference noise signal for removal of a tissue effect and a venous effect, respectively. The arterial signal is modeled and a cost function is defined to find the optimum noise reference for removal of venous effect over time.

When the body remains still, $\Delta D_t$ is close to zero and the effect of tissue manifests itself as a DC component in the recorded PPG signal. This DC component can be removed in analog front-end or by digital filtering. However, in the presence of motion, this component is no longer constant. Fluctuations caused by body movements, for example during walking, running and treadmill exercise, can be seen in the recorded PPG signal. Such new rhythmic pattern and variation in the PPG signal can lead to an inaccurate and unreliable fundamental period for the PPG signal. To overcome these issues, two wavelengths are employed to cancel out the effects of $Z_t$ and $Z_b$ that are independent of the wavelength. In a preferred embodiment, optical densities that correspond to a two-wavelength PPG biosensor, as defined in Eq. 4, are subtracted (subscript i and j are used for wavelengths and t to represent tissue effect), and define the result by:

$$\Delta A_{ij\_t} = [\sqrt{E_{a_i}(E_{a_i} + F)} - \sqrt{E_{a_j}(E_{a_j} + F)}] Hb_a \Delta D_a + [\sqrt{E_{v_i}(E_{v_i} + F)} - \sqrt{E_{v_j}(E_{v_j} + F)}] Hb_v \Delta D_v \quad \text{Eq. 5}$$

The term $\Delta A_s$ in Eq. 4 is independent of wavelength and the time difference between recording of both wavelengths is negligible compared to typical time for human motions. This term is now effectively removed in Eq. 5. Consequently, the signal portion due to blood pulsation will remain in $\Delta A_{ij\_t}$ and the effect of tissue during body movement will be canceled out.

In a preferred embodiment, a reference signal defined by $\Delta A_{ij\_t}$ is generated and used in an adaptive filter to enhance signal quality for extracting a PPG fundamental period. The PPG fundamental period will, therefore, be reliably extracted after signal enhancement using the generated reference signal. In another embodiment, the wavelength-independent, i.e., the tissue effect, is applied to more than two wavelengths to remove the tissue noise effect.

Another main source of error and interference is the change of venous blood during motion artifact. The effect of venous blood appears in the calculation of oxygen saturation more noticeably while the effect of tissue hinders extraction of heart rate. Motion artifact due to tissue effect is removed using $\Delta A_{ij\_t}$ as a reference signal. The removal of motion artifact is equivalent to setting $\Delta A_s$ of Eq. 4 equal to zero. Now that $\Delta A_s$ is equal to zero, Eq. 4 for the removal effect of venous blood movement is as follows for a two-wavelength PPG biosensor:

$$\begin{cases} \Delta A_i = \sqrt{E_{a_i}(E_{a_i} + F)}\, Hb_a \Delta D_a + \sqrt{E_{v_i}(E_{v_i} + F)}\, Hb_v \Delta D_v \\ \Delta A_j = \sqrt{E_{a_j}(E_{a_j} + F)}\, Hb_a \Delta D_a + \sqrt{E_{v_j}(E_{v_j} + F)}\, Hb_v \Delta D_v \end{cases} \quad \text{Eq. 6}$$

Each of the two sources of information, $\Delta A_i$ and $\Delta A_j$, is a mixture of arterial blood, represented by subscript a, and venous blood, represented by subscript v, at a particular wavelength (i,j). Each first term of optical density in Eq. 6 represents the arterial blood signal and each second term represents the venous blood signal. Weighted subtraction of these two sources is employed to calculate, a reference noise signal, i.e., $\Delta A_{ij\_v} = \Delta A_i - \beta \Delta A_j$. Eq. 6 becomes:

$$\begin{cases} \Delta A_{ij\_v} = \left[(r_a - \beta)\sqrt{E_{a_i}(E_{a_i} + F)}\right] Hb_a \Delta D_a + \\ \qquad \left[(r_v - \beta)\sqrt{E_{v_i}(E_{v_i} + F)}\right] Hb_v \Delta D_v \\ r_a = \sqrt{E_{a_i}(E_{a_i} + F)} / \sqrt{E_{a_j}(E_{a_j} + F)} \\ r_v = \sqrt{E_{v_i}(E_{v_i} + F)} / \sqrt{E_{v_j}(E_{v_j} + F)} \end{cases} \quad \text{Eq. 7}$$

where $r_a$ is the ratio of arterial optical densities which is linearly related to arterial oxygen saturation and $r_v$ is the ratio of venous optical densities. After removal of the tissue effect, the weighted subtraction of optical densities in Eq. 7 is used to separate two signal sources related to artery and venous. Eq. 7 indicates that with proper tuning of the weight $\beta$, the reference noise signal defined by $\Delta A_{ij\_v}$ may contain a venous component signal, i.e. $\beta = r_a$, an arterial component signal i.e. $\beta = r_v$, or a combination of these two sources. In other words, $\beta$ is swept and a reference noise signal is generated for the various values of $\beta$. As can be seen in Eq. 7, there is a range of $\beta$ where the reference noise signal has the venous component signal and a wider range of $\beta$ where the reference noise signal has the arterial component signal.

Separation of the venous component signal in Eq. 7 enables use of the venous component signal as the reference noise signal in an adaptive filter to remove the venous noise from Eq. 6, i.e., generate a venous noise reference signal. In order to find $\beta$ that removes arterial component signal, i.e., the first term of Eq. 7, and keep the venous component signal, a set of criteria is needed to quantify the performance of any given $\beta$. The arterial component signal is a periodic signal with a temporal structure. The more pronounced periodic property of the arterial term in Eq. 7 will be exploited by the subsequent adaptive and prediction error filtering to separate these two signals to estimate of arterial component signal. As will be described below, the optimum $\beta(\beta_{opt})$ is used in estimating the venous noise reference signal and to implement an adaptive filter for removal of venous blood movement noise.

Figure 4A:
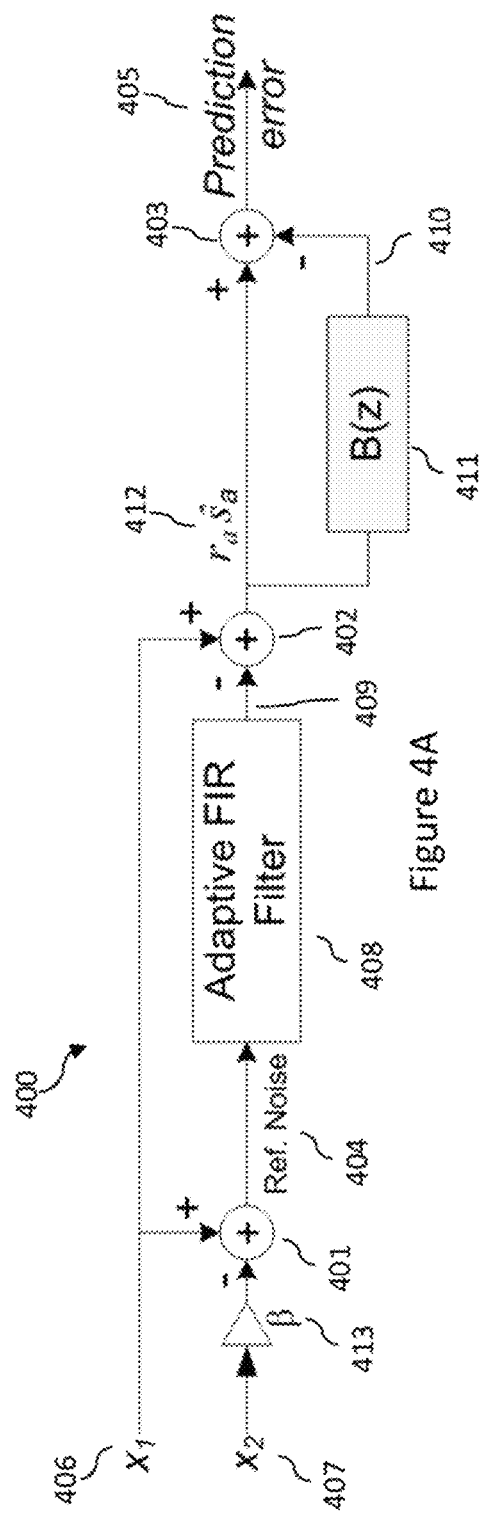
FIG. 4A is a flowchart of a model for optimizing a weight of a preferred embodiment.

Referring to FIG. 4A, model 400 for optimizing $\beta$ will be described. Model 400 includes weighted subtractor 401, adaptive enhancer 402, and predictor filter 403. Adaptive enhancer 402 removes the second term of $\Delta A_i$ in Eq. 6 and keeps the arterial component signal using the output of weighted subtractor 401 as the reference noise signal 404. Prediction filter 403 is used to predict the arterial component signal using previous values of the arterial component signal and generate prediction error 405. Each of input signal 406 $x_1$ and input signal 407 $x_2$ corresponding to the optical densities $\Delta A_i$ and $\Delta A_j$ in Eq. 6, is a linear combination of arterial and venous signals. Using arterial and venous optical density ratios, $r_a$ and $r_v$, defined in Eq. 7, input signal 406 $x_1$ and input signal 407 $x_2$ are expressed as:

$$\begin{cases} x_1 = r_a s_a + r_v s_v \\ x_2 = s_a + s_v \end{cases} \quad \text{Eq. 8}$$

Figure 4B:
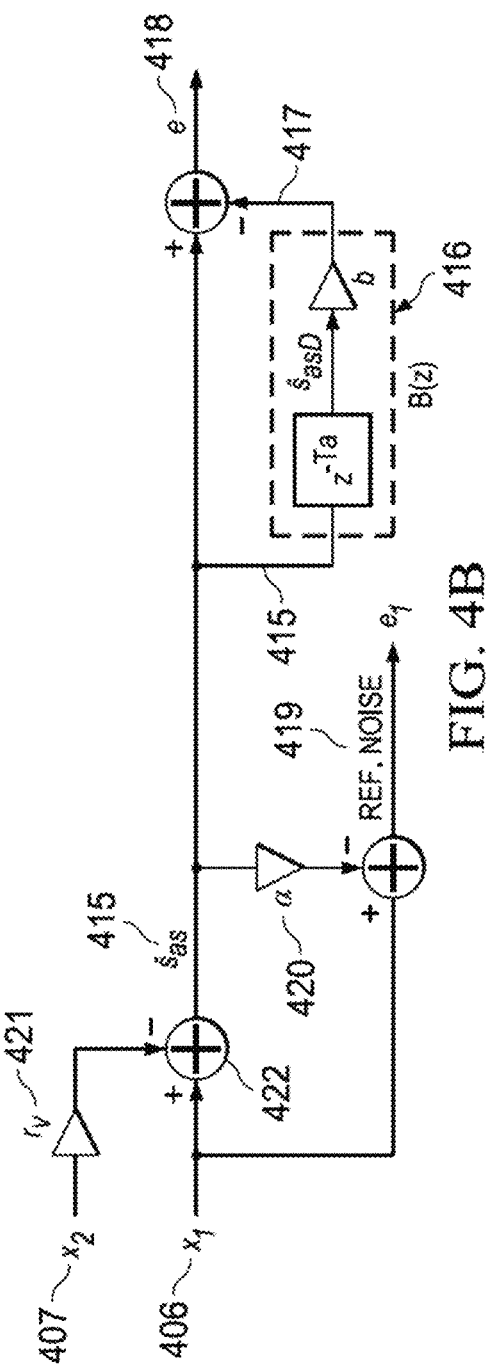
FIG. 4B is a flowchart of a model for finding an optimized weight of a preferred embodiment.

Weighted subtractor 401 generates a weighted subtraction of input signals 406 and 407 $x_1$ and $x_2$ and generates a reference noise signal 404 corresponding to $\Delta A_{ij\_v}$ in Eq. 7. Adaptive filter 408 uses reference noise signal 404 to filter out the noise, i.e., the second term of Eq. 6, which is the venous component signal, thereby leaving arterial component signal 409 intact. Arterial component signal 409 is a temporally correlated signal. Adaptive enhancer 402 combines arterial component signal 409 with input signal 406 $x_1$ to generate enhanced arterial component signal 412. As shown, the temporal structure of an enhanced arterial signal 412 is modeled with adaptive enhancer 411 with the z-transform of B(z) at the output 410 of adaptive enhancer 411. Adaptive enhancer 411 models enhanced arterial signal 412, $r_a \hat{s}_a(n)$. B(z) in adaptive enhancer 411 estimates enhanced arterial component signal 412 $r_a \hat{s}_a$ for any given $\beta$. For the optimum value of $\beta(\beta_{opt})$ at 413, $$r_a \hat{s}_a \approx \sqrt{E_{a_i}(E_{a_i}+F)} Hb \Delta D_a \quad \text{Eq. 9}$$

where $\sqrt{E_{a_i}(E_{a_i}+F)} Hb \Delta D_a$ is the first term of $\Delta A_i$, which is a predictable (periodic) signal, and represents the arterial component signal. Therefore, for $\beta_{opt}$, the variance of the prediction error 405 will be minimized. In order to find $\beta_{opt}$, model 414 of FIG. 4B is employed Referring to FIG. 4B, in model 414 a linear combination of input signals 406 and 407 $x_1$ and $x_2$, i.e. $x_1 - \beta x_2$ with $\beta_{opt}$, provides an estimate of the reference venous noise signal at 419, where $$\beta_{opt} = \frac{\alpha r_v}{1-\alpha}.$$

Model 414 extracts a scaled estimate 415, $\hat{s}_{as}$, of the arterial component signal in input signal 406 $x_1$ at 422 and minimizes the variance of the error signal 417 e(n) at the output of linear predictor 416. Error signal 418, e, is the difference between a current sample of scaled estimate 415, $\hat{s}_{as}(n)$, and the output B(z) of the linear predictor 416, i.e., error signal 417 e(n).

In one embodiment, linear predictor 416 is a Finite Impulse Response (FIR) filter. In another embodiment, linear predictor 416 is an Infinite Impulse Response (IIR) filter.

The relation between error signal 417 and scaled estimate 415 is mathematically expressed as:

$$e(n) = (1-B(z))\hat{s}_{as}(n) \quad \text{Eq. 10}$$

Generally, the FIR embodiment of prediction filter 416 of order P can be expressed as:

$$B(z) = \sum_{l=0}^{P} b_l z^{-l} \quad \text{Eq. 11}$$

Optimization of $r_v$ at 421 and coefficient b of B(z) is determined by minimizing the mean square error defined as the cost function:

$$J(r_v, b) = E[e^2] \quad \text{Eq. 12}$$

where b is the vector of coefficient of prediction filter 416. In order to simplify the computation and use the extracted fundamental period of the signal, a linear predictor is chosen, $B(z) = b z^{-T_a}$, where $T_a$ is the fundamental period of the arterial component signal in discrete time and b is the only coefficient of the filter. The cost function, $E[e^2]$, is now written as:

$$J(r_v, b) = E[\hat{s}_{as}^2(n)] - 2bE[\hat{s}_{as}(n)\hat{s}_{as}(n-T_a)] + b^2 E[\hat{s}_{as}^2(n-T_a)] \quad \text{Eq. 13}$$

When the gradients of the cost function with respect to $r_v$ and b are zero, the prediction error, error signal 417 e(n), has its minimum value. So, by equating the gradient of the cost function with respect to $r_v$ and b to zero, we obtain a system of equations. Solving this system of equations for $r_v$ and b, results in:

$$r_v = \frac{-E[x_1^2]E[\hat{s}_{asD}x_2] + E[x_1x_2]E[\hat{s}_{asD}x_1]}{E[x_2^2]E[\hat{s}_{asD}x_1] - E[x_1x_2]E[\hat{s}_{asD}x_2]} \text{ and} \qquad \text{Eq. 14}$$

$$b = E[\hat{s}_{as}(n)\hat{s}_{as}(n - T_a)] / E[\hat{s}_{as}(n - T_a)] \qquad \text{Eq. 15}$$

For every given b, including b for which $$\frac{\partial J(r_v,b)}{\partial r_v} = 0,$$

the error curve is a quadratic function of $r_v$ that includes a single minimum on the error curve. After extraction of the scaled estimate 415 $\hat{s}_{as}$ of the arterial component signal in input signal 406 $x_1$, the reference noise signal 419 is extracted by removing the scaled estimate 415 $\hat{s}_{as}$ of the arterial component signal from input signal 406 $x_1$ by minimizing the variance of signal $e_1$, reference noise signal 419. By taking gradient of $E[e_1^2]$ with respect to $\alpha$ at 420, we obtain:

$$\alpha = \frac{E[x_1^2] - r_v E[x_1x_2]}{E[\hat{s}_{as}]} \qquad \text{Eq. 16}$$

Signal $e_1$ is the reference noise signal 419. As a result, the linear combination of signals $x_1$ and $x_2$ (i.e. $x_1-\beta x_2$) with optimum $\beta$, $$\beta_{opt} = \frac{\alpha r_v}{1 - \alpha},$$

provides an estimate of the reference venous noise signal at 419.

Figure 5A:
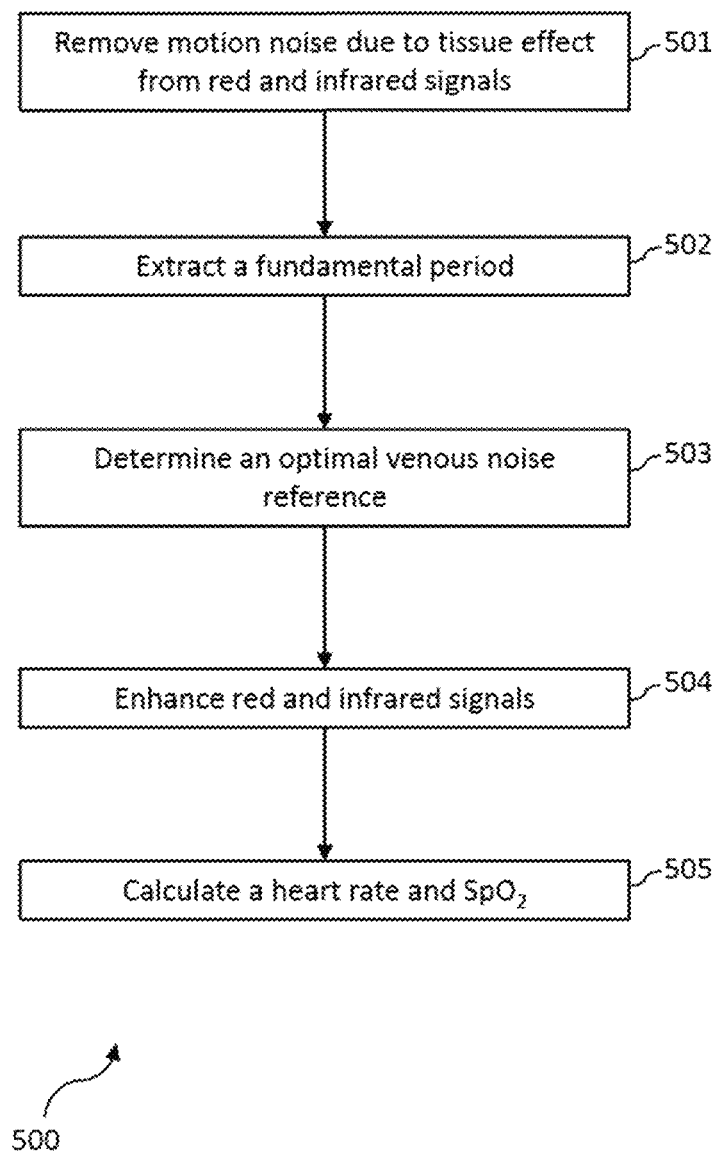
FIG. 5A is a flowchart of a method for enhancing a set of PPG signals of a preferred embodiment.

Referring to FIG. 5A, method 500 for signal enhancement and extraction of $SpO_2$ and heart rate will be described. At step 501, motion noise due to a tissue effect is removed from a red PPG signal and an infrared PPG signal generating an enhanced red PPG signal and an enhanced infrared PPG signal. At step 502, a fundamental period is extracted using the enhanced red PPG signal. At step 503, an optimal venous noise reference signal is determined using the enhanced red PPG signal and the enhanced infrared PPG signal. At step 504, the enhanced red PPG signal and the enhanced infrared PPG signal are further enhanced using a time-variant optimum venous noise reference signal to generate a clean red PPG signal and a clean infrared PPG signal. At step 505, a heart rate and a $SpO_2$ is calculated using the clean red PPG signal and the clean infrared PPG signal.

Figure 5B:
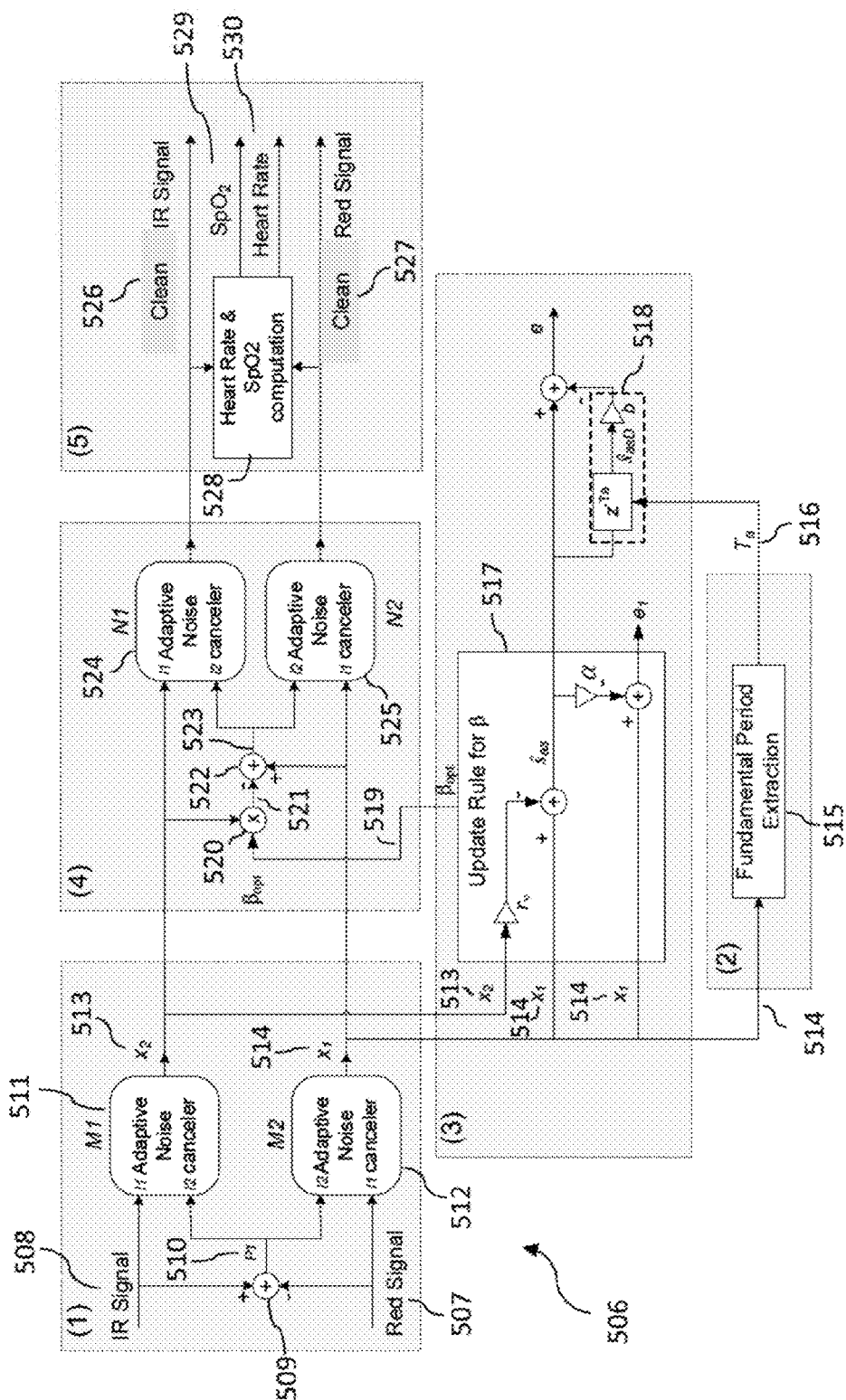
FIG. 5B is a block diagram of a system for enhancing a set of PPG signals of a preferred embodiment.

Referring to FIG. 5B, a block diagram of system 506 that implements method 500 will now be described. Red signal 507 and infrared signal 508 are subtracted at 509 to generate reference signal 510. Reference signal 510 corresponds to $\Delta A_{ij\_r}$ in Eq. 5. Reference signal 510 is used in adaptive filters 511 and 512 to remove motion noise due to tissue and to generate enhanced red signal 514 and enhanced infrared signal 513, respectively.

Enhanced red signal 514 is connected to extractor 515. Extractor 515 extracts fundamental period 516 from enhanced red signal 514. Extractor 515 is further connected to linear predictor 518. Linear predictor 518 receives fundamental period 516.

After removing motion noise due to tissue effect and extracting fundamental period 516 $T_a$, enhanced red signal 514 $x_1$ and enhanced infrared signal 513 $x_2$ are defined by $\Delta A_i$ and $\Delta A_j$ of Eq. 6, respectively.

Enhanced infrared signal 513 and enhanced red signal 514 are connected to optimizer 517. Optimizer 517 is connected to linear predictor 518. Optimizer 517 and linear predictor 518 generate an optimum weight $\beta$ 519 ($\beta_{opt}$), as previously described in FIGS. 4A and 4B. Extracted fundamental period 516 is used in linear predictor 518 to generate prediction error 531 e. The optimum weight $\beta$ 519 ($\beta_{opt}$) is updated using update rules defined by Eq. 14 and Eq. 16 for $r_v$ and $\alpha$, respectively. This process is done on a frame basis and for each frame a new $\beta_{opt}$ is extracted. $\beta_{opt}$ provides an optimum reference noise, consequently, a set of clean signals contain only arterial component needed to extract features such as $SpO_2$.

Weighted subtraction of enhanced infrared signal 513 and enhanced red signal 514 with current $\beta_{opt}$ is used to form reference noise 513 defined by Eq. 7 for adaptive filters 524 and 525. Optimum weight $\beta$ 519 ($\beta_{opt}$) is combined with enhanced infrared signal 513 at 520 to form combined signal 521. Combined signal 521 is combined with enhanced red signal 514 at 522 to generate reference noise 523. Adaptive filter 524 uses reference noise 523 to remove noise from enhanced infrared signal 513 to generate clean infrared signal 526. Adaptive filter 525 uses reference noise 523 to remove noise from enhanced red signal 514 to generate clean red signal 527. Dominant and high power motion noise conceals the waveform amplitude of arterial component when no enhancement algorithm is applied. The disclosed embodiment provides clean signals at the output preserving peak-to-peak values of the arterial signal for amplitude analysis.

Clean infrared signal 526 and clean red signal 527 are received by extractor 528. Extractor 528 uses clean infrared signal 526 and clean red signal 527 to calculate $SpO_2$ 529 and heart rate 530.

In one embodiment, the ratio of ratios method is employed for the measurement of $SpO_2$ in pulse oximetry. This method extracts the DC and AC parts of the clean red and infrared PPG signals and computes the ratio of ratios, R, as:

$$R = \frac{R_{ac}/R_{dc}}{IR_{ac}/IR_{dc}} \qquad \text{Eq. 17}$$

where $R_{ac}$ and $R_{dc}$ denote the magnitudes of the pulsatile and the DC parts, respectively, of the clean red signal. $IR_{ac}$ and $R_{dc}$ are the magnitudes of the pulsatile and DC portions of the clean infrared signal, respectively. In one embodiment, $SpO_2$ is then calculated by employing the following empirical equation:

$$SpO_2\% = (K_1 + K_2 R)\% \qquad \text{Eq. 18}$$

where $K_1$ and $K_2$ are constants empirically found and tuned for a particular sensor platform. For example, $K_1$ is 105 and $K_2$ is -23. Other values for $K_1$ and $K_2$ may be employed.

In another embodiment, a correlation-canceller based $SpO_2$ extraction method is employed, as will be further described below. In another embodiment, Eq. 18 and the correlation-canceller based method are alternatively employed depending on the type of the motion and the level of the venous blood movement. For example, Eq. 18 is employed on various types of physical motion such as those moving hands/legs, sit-stand body moves, bending, walking, running and their corresponding changes in the levels of venous blood movement. For example, the correlation-canceller based method is employed on various types of motions related to skeletal muscle pump and respiratory pump and their corresponding changes in the levels of venous blood movement. The correlation-canceller based method may be employed during lower rate of change of oxygen saturation or transient severe motion.

In a preferred embodiment, the fundamental period is the heart rate. In one embodiment, the heart rate is calculated using extractor 515. In another embodiment, any known heart rate extraction method may be employed based on the application and the need once the clean red and infrared signals are obtained.

In another embodiment, a correlation-based heart rate extractor is employed to calculate the heart rate, as will be further described below.

Referring to FIGS. 6A and 6B, each of the adaptive filters 511, 512, 524, and 525 will be further described. Each of adaptive filters 524 and 525 will be further described as adaptive filter 600. Each of adaptive filters 511 and 512 will be further described as adaptive filter 610. Each of adaptive filters 600 and 610 includes a filtering process that applies a linear filter on a reference input.

Referring to FIG. 6A, filter 603 is applied to reference noise 602 $I_2$. Reference noise 602 $I_2$ is linearly correlated with d(i), the noise component in signal 601 $I_1$. By subtracting output 604 $\hat{d}(n)$ of filter 603 from signal 601 s(n)+d(n) at 605, enhanced signal 609 and error estimation 606 are generated. Adaptive process 607 automatically updates coefficient 608 of filter 603 based on a set of criteria extracted from error estimation 606. The set of criteria is defined by adaptive process 607, as will be further described below.

Referring to FIG. 6B, filter 613 is applied to reference signal 612 $I_2$ to generate enhanced signal 614 s(n). Enhanced signal 614 s(n) is subtracted from signal 611 s(n)+d(n) to generate error estimation 616. Adaptive process 617 automatically updates coefficient 618 of filter 613 based on a set of criteria extracted from error estimation 616. The set of criteria is defined by the adaptive process 617, as will be further described below.

Referring to FIGS. 6A and 6B, for each of adaptive processes 607 and 617, the Least-Mean-Square (LMS) process and its variations are employed. In a preferred embodiment, each of adaptive processes 607 and 617 is the NLMS method due to its lower complexity compared with other techniques and immunity to the fluctuation in the signal energy. Other adaptive optimization techniques including recursive least square may be used.

In a preferred embodiment, each of filters 603 and 613 is a linear filter. In another embodiment, each of filters 603 and 613 is a nonlinear filter.

Given the desired output signal, input reference $I_2$ and the current value of the filter coefficient w(n), the update equation for each of adaptive processes 607 and 617 is expressed as:

$$w(n+1) = w(n) + \frac{2\eta}{\varepsilon + \sum_{i=0}^{N-1} I_2^2(n-i)} I_2(n)e(n) \qquad \text{Eq. 19}$$

where N is the length of the adaptive filter and $0<\eta<1$ and $\epsilon$ is a small number, for example 0.0003, to avoid division by zero due to numerical and fixed point computations. Error estimations 606 and 616 are s(n)+d(n)−$\hat{d}$(n) and d(n)+s(n)−$\hat{s}$(n), respectively. In adaptive filter 600, the reference input is only correlated with the noise source. Therefore, minimizing error power minimizes the noise power in mean square sense and enhanced signal 609 is obtained at the output. Similarly, in adaptive filter 610, the reference input is only correlated with the signal source s(n). Therefore, minimizing error power results in an enhanced noise at the primary output 620, and an enhanced signal output 614 $\hat{s}$(n). An input red or infrared signal corrupted by motion noise is the desired input signal in adaptive filter 610. The reference signal 611 represents the true signal.

Figure 7:
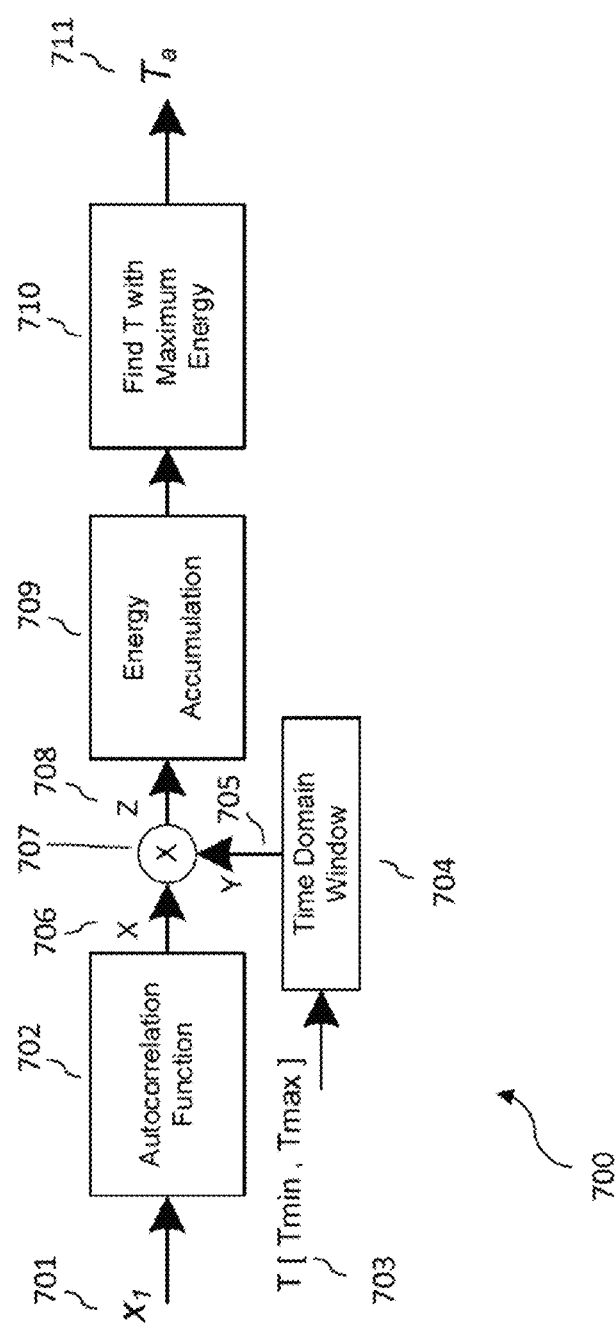
FIG. 7 is a block diagram of a real-time fundamental period estimator of a preferred embodiment.

Referring to FIG. 7, step 502 will be further described as method 700. Method 700 assumes that the period stays the same, i.e. the signal is stationary on each frame. At step 702, an autocorrelation 706 of an enhanced signal 701 is computed. In this step, the autocorrelation function C(t) preserves periodicity information of enhanced signal 701. When N samples of enhanced signal 701 are available, the autocorrelation is expressed as:

$$C(t) = \frac{1}{N}\sum_{n=0}^{N-1} x_1(x)x_1(n+t) \qquad \text{Eq. 20}$$

for N larger than several times the period $T_a$ of C(t) where $x_1$(n) is enhanced signal 701 which corresponds to enhanced red signal 514 of adaptive filter 512 in FIG. 5B, t is a lag value and n is discrete time. Both n and t are integers representing time indices. The auto correlation sequence has its maximum value at lag zero and integer multiples of its fundamental period, $T_a$. In one embodiment, the autocorrelation function is linearly combined with the previous autocorrelation functions. In a preferred embodiment, the window length of the autocorrelation function is 1500 samples. Any number of samples may be employed.

At step 704, a time domain window 705 is calculated. In this step, for each value of T in the limited range of the period, [Tmin, Tmax], the time domain window $$\alpha_1\delta(t-T)+\alpha_2\delta(t-2T)+\alpha_3\delta(t-3T) \qquad \text{Eq. 21}$$

is generated where $\delta$ is dirac delta function. $\alpha_1$, $\alpha_2$ and $\alpha_3$ are empirically obtained as 1, 0.9, 0.8, respectively, to enhance the accuracy of period estimator and prevent gross errors.

At step 707, time domain window 705 is multiplied with autocorrelation function 706 in time domain. This step results in a modified autocorrelation function 708 for each window, which is zero for all values of t except T, 2T and 3T. Different time domain windows may be used. History of heart rate may be used in computation of the heart rate.

At step 709, a summation is computed for all modified autocorrelations, at a set of values of T.

At step 710, the window passing maximum energy through the autocorrelation function is determined, which defines a fundamental period 711 $T_a$.

In one embodiment, decreasing amplitude of the time window is considered to reduce susceptibility to period doubling. The extracted fundamental period, $T_a$, is used in prediction error filter to find the optimum $\beta$.

Since method 700 determines the window passing maximum energy instead of searching for peaks in the autocorrelation function, this method is particularly well-suited for noisy environments of wearable sensors.

In one embodiment, the time window, $\alpha_1\delta(t-T)+\alpha_2\delta(t-2T)+\alpha_3\delta(t-3T)$, is used that represents a train of pulses with fundamental frequency $f_w$ which reduces the leakage from motion noise components. In this embodiment, the frequency domain is determined by finding $f_w$ such that maximum correlation exists between spectrum of the time window and the spectrum of PPG signal. Different window types may be designed and optimized for the PPG signal in the presence of motion artifact.

Figure 8:
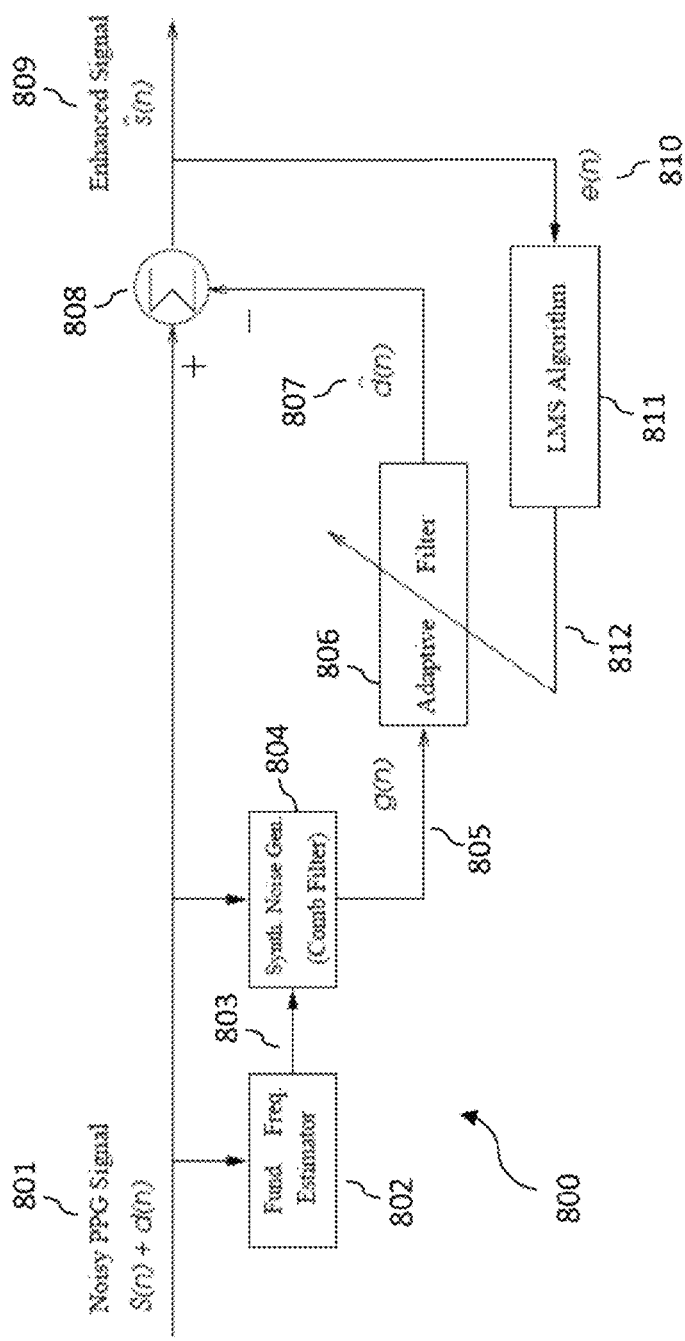
FIG. 8 is a block diagram of an adaptive noise canceller using synthetic noise reference of a preferred embodiment.

Referring to FIG. 8 in another embodiment, a real-time method 800 for adaptive noise cancellation using a generated synthetic noise reference based on the fundamental frequency is shown. A primary input signal 801, i.e. s(n)+d(n) contains a raw PPG signal corrupted by motion noise. Estimator 802 uses primary input signal 801 to generate an estimated fundamental frequency 803. In a preferred embodiment, method 700 is used to estimate the fundamental frequency 803.

A reference noise signal 805 g(n) is generated by comb filter 804. In a preferred embodiment, a comb filter with a transfer function $(1-z^{-T_a})/2$ is applied to the primary input signal 801 where $T_a$ is the fundamental frequency 803. Reference noise signal 805, g(n) is highly correlated with motion artifact.

Adaptive filter 806 generates an estimate of motion noise 807 $\hat{d}(n)$ from reference noise signal 805. The estimate of motion noise 807 is subtracted from primary input signal 801 at 808 to reduce the noise level and generate enhanced signal 809 and error signal 810. Adaptive process 811 adapts adaptive filter 806 to minimize power in error signal 810 e(n) by self-adjusting coefficient 812 using a Least Mean Squares method to minimize an error cost function, as previously described.

Figure 9:
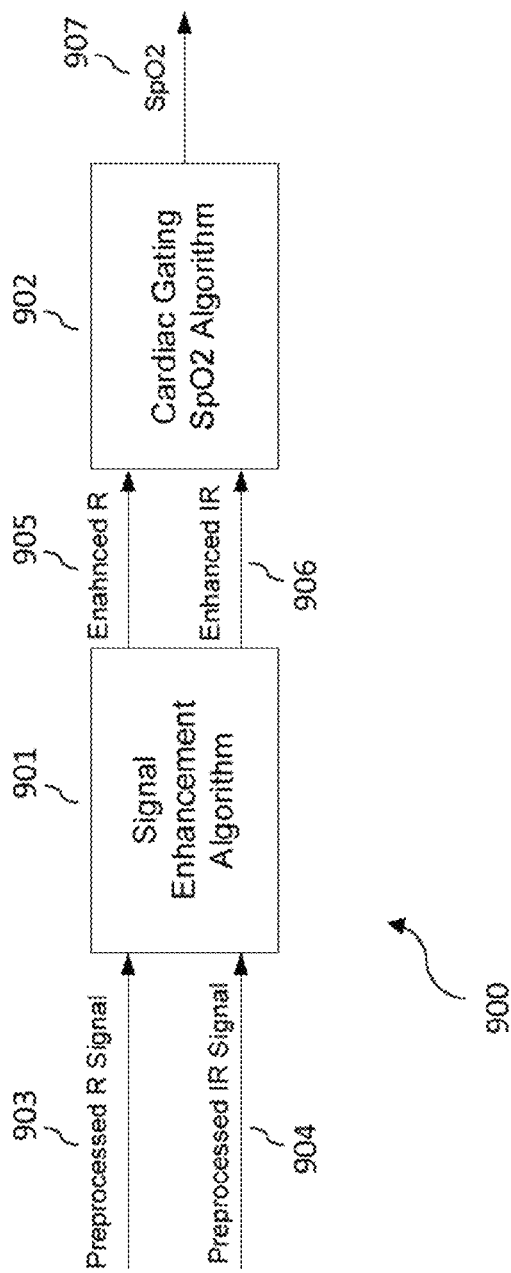
FIG. 9 is a block diagram of a motion-tolerant signal enhancing and cardiac gating system of a preferred embodiment.

Referring to FIG. 9 in another embodiment, motion-tolerant system 900 includes signal enhancement unit 901 and cardiac gating $SpO_2$ unit 902. After conditioning the received red and infrared signals by low pass filtering, preprocessed red signal 903 and preprocessed infrared signal 904 enter signal enhancement unit 901 and the quality of preprocessed red signal 903 and preprocessed infrared signal 904 are improved using adaptive filtering approaches to generate enhanced red signal 905 and enhanced infrared signal 906. Cardiac gating $SpO_2$ unit 902 calculates $SpO_2$ 907 using enhanced red signal 905 and enhanced infrared signal 906.

Figure 10:
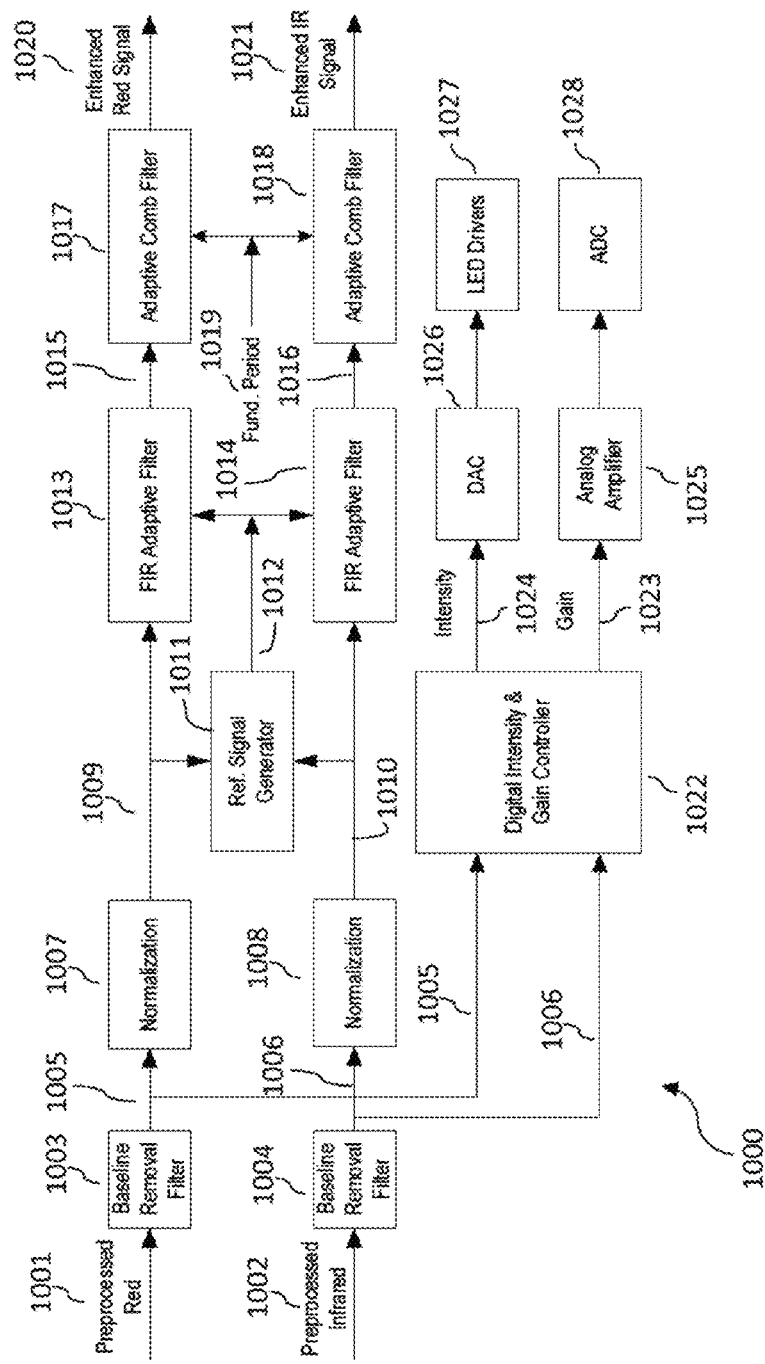
FIG. 10 is a block diagram of a signal enhancement unit of a preferred embodiment.

Referring to FIG. 10, signal enhancement unit 901 will be further described as signal enhancement unit 1000. Linear phase digital filters 1003 and 1004 remove baseline changes from red signal 1001 and infrared signal 1002, respectively, to generate red baseline signal 1005 and infrared baseline signal 1006. Red and infrared LEDs may emit light with different intensities and photodetectors may have different sensitivity at red and infrared wavelengths. Further, the physical condition of site of a measurement such as tissue, bone and skin properties and the length of the measurement site are different from patient to patient. Therefore, red baseline signal 1005 and infrared baseline signal 1006 must be normalized. In a preferred embodiment, each of red baseline signal 1005 and infrared baseline signal 1006, which shows the mean of the signal over time, is used to normalize red baseline signal 1005 and infrared baseline signal 1006 to generate normalized red signal 1009 and normalized infrared signal 1010.

The AC component of normalized red and infrared signals 1009 and 1010 becomes independent of intensity of LEDs and photodetector nonlinear effect. Therefore, they can effectively be compared with each other in parameter extraction units such $SpO_2$ measurement. After the baseline removal and normalization of red and infrared signals, an intermediate reference signal 1012 is generated by reference signal generator 1011 by subtracting normalized red signal 1009 and normalized infrared signal 1010.

Intermediate reference signal 1010 is used by each of FIR adaptive filter 1013 and FIR adaptive filter 1014. Generally, any correlation canceller can be used for FIR adaptive filter 1013 and FIR adaptive filter 1014. In a preferred embodiment, each of FIR adaptive filter 1013 and FIR adaptive filter 1014 is adaptive noise canceller 610. The output of each FIR adaptive filter is a filtered signal and an error signal. FIR adaptive filter 1013 outputs filtered red signal 1015 and FIR adaptive filter 1014 outputs filtered infrared signal 1016.

Each filtered signal has a harmonic structure, which is used to further enhance the signal quality in the presence of motion artifact. A harmonic enhancement process is used to enhance the harmonic structure of each filtered signal in the presence of motion. In the harmonic enhancement process, adaptive comb filters 1017 and 1018 adapt to filtered red signal 1015 and filtered infrared signal 1016, respectively, with a single parameter, fundamental period or fundamental frequency of the respective signal. In a preferred embodiment, fundamental period 1019 is generated and used to adapt each of adaptive comb filters 1017 and 1018, as will be described below. The output of adaptive comb filter 1017 is an enhanced red signal 1020. The output of adaptive comb filter 1018 is an enhanced infrared signal 1021.

Another issue in ambulatory and portable applications is reliable acquisition of the signals. Presence of the motion leads to fluctuation on baseline and amplitude of the signals and there is a need for a way of controlling the analog front end which prevents nonlinear clipping and provides appropriate signal amplitude at the input of enhancement unit 1000. In order to prevent clipping and use the available dynamic range of amplifier 1025 in the analog front end, a digital gain and intensity controller 1022 is included.

Each of red baseline signal 1005 and infrared baseline signal 1006 is measured over time and a moving average filter is applied on each signal by digital gain and intensity controller 1022. An amplitude of each signal after baseline removal is computed. The photo-detector gain 1023 and LED intensity 1024 is adjusted based on the baseline and AC value of infrared baseline signal 1006. LED intensity 1024 is converted with digital-to-analog converter 1026 for LED drivers 1027. LED drivers 1027 drive the LEDs for the red and infrared light based on LED intensity 1024. The received photo-detector signal is amplified based on the photo-detector 1023 and converted with analog-to-digital converter 1028.

In order to reduce the accumulated effect of motion artifact, $SpO_2$ is preferably calculated on a sub-heart beat time duration. As will be further described below, cardiac gating $SpO_2$ is employed on sub-heart beat cycle time frames and determines the best time duration in each beat cycle based on the physiology of blood circulation.

Figure 11A:
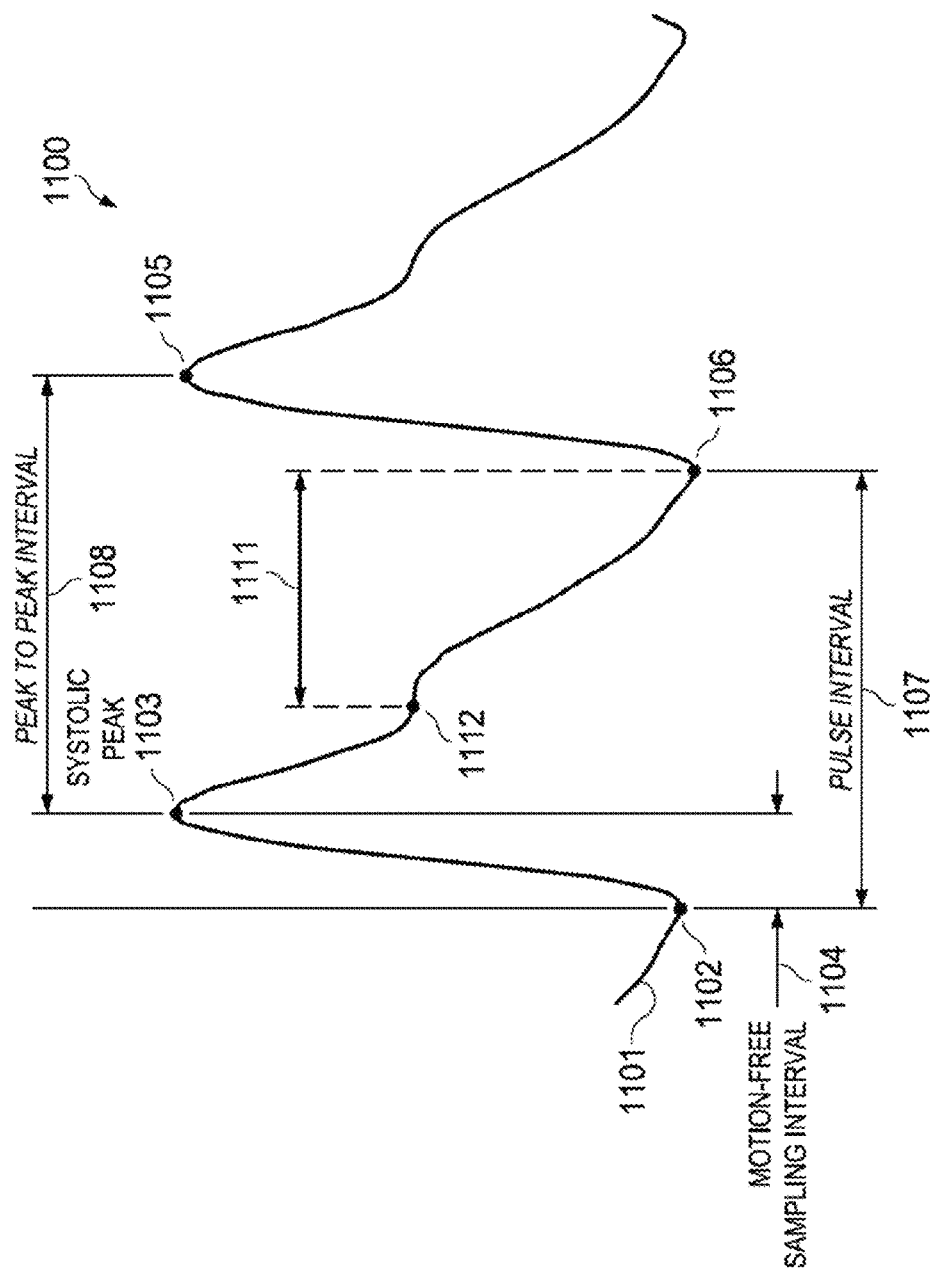
FIG. 11A is a graph of a sampling window in a biphasic cardiac activity of a preferred embodiment.
Figure 11B:
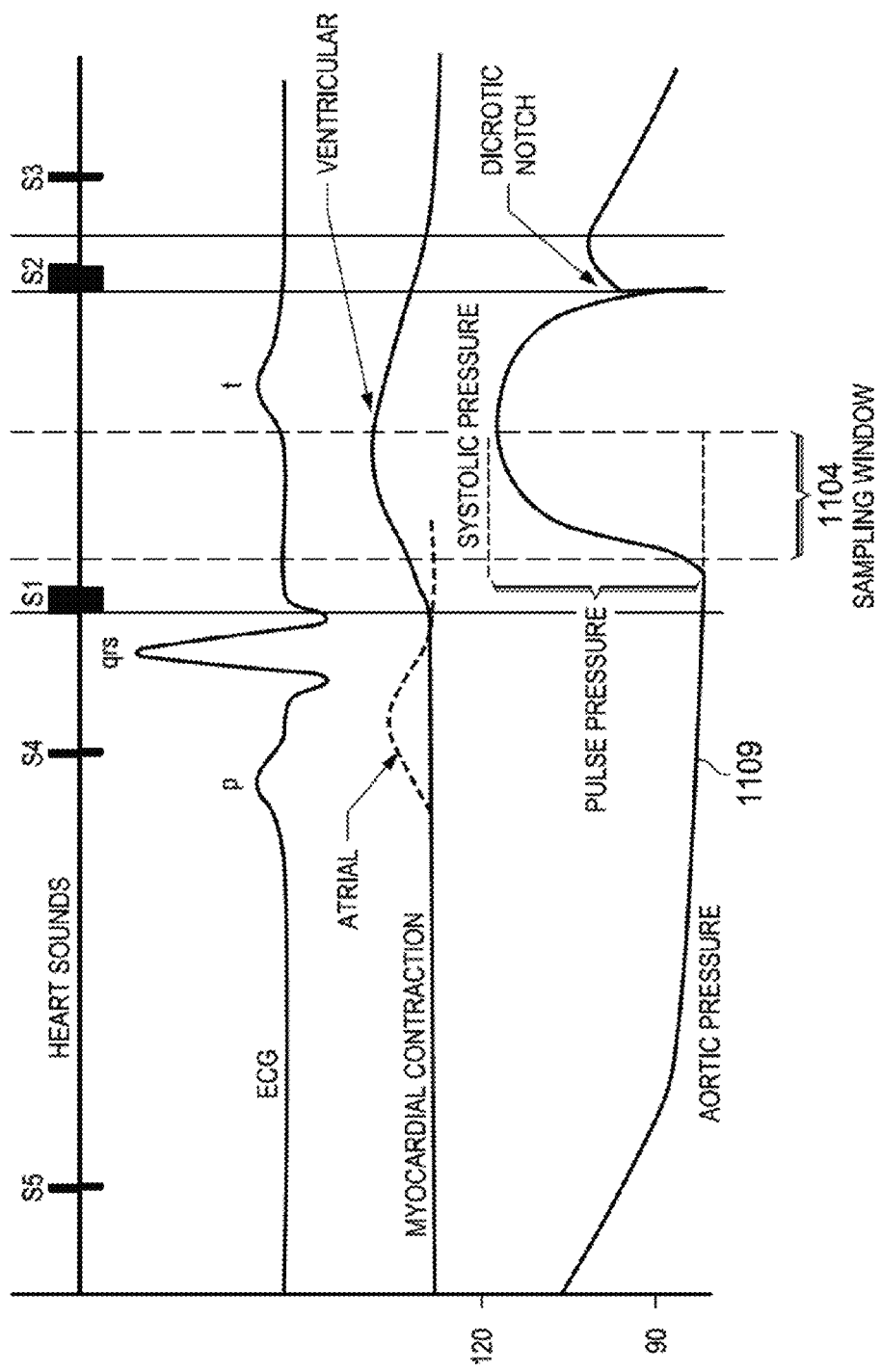
FIG. 11B is a graph of a sampling window in a biphasic cardiac activity of a preferred embodiment.
Figure 11C:
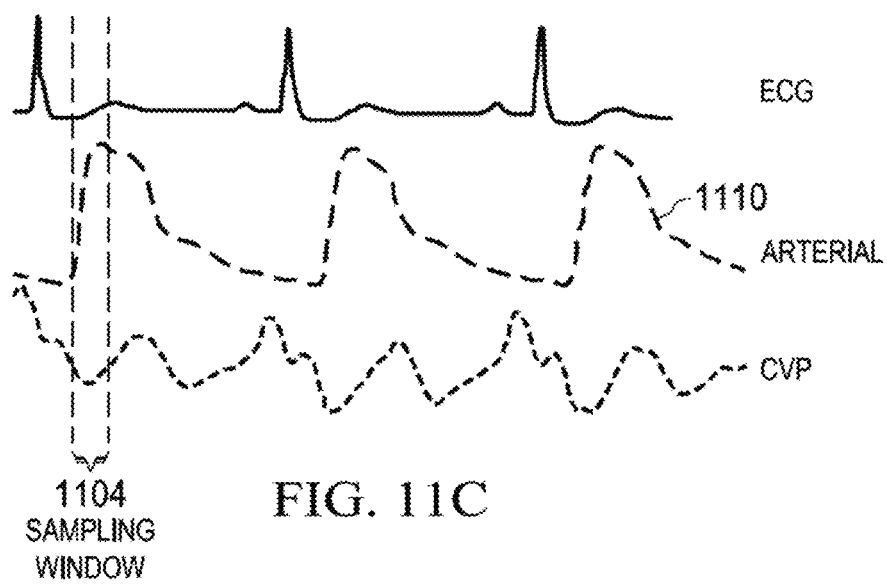
FIG. 11C is a graph of a sampling window in a biphasic cardiac activity of a preferred embodiment.
Figure 11D:
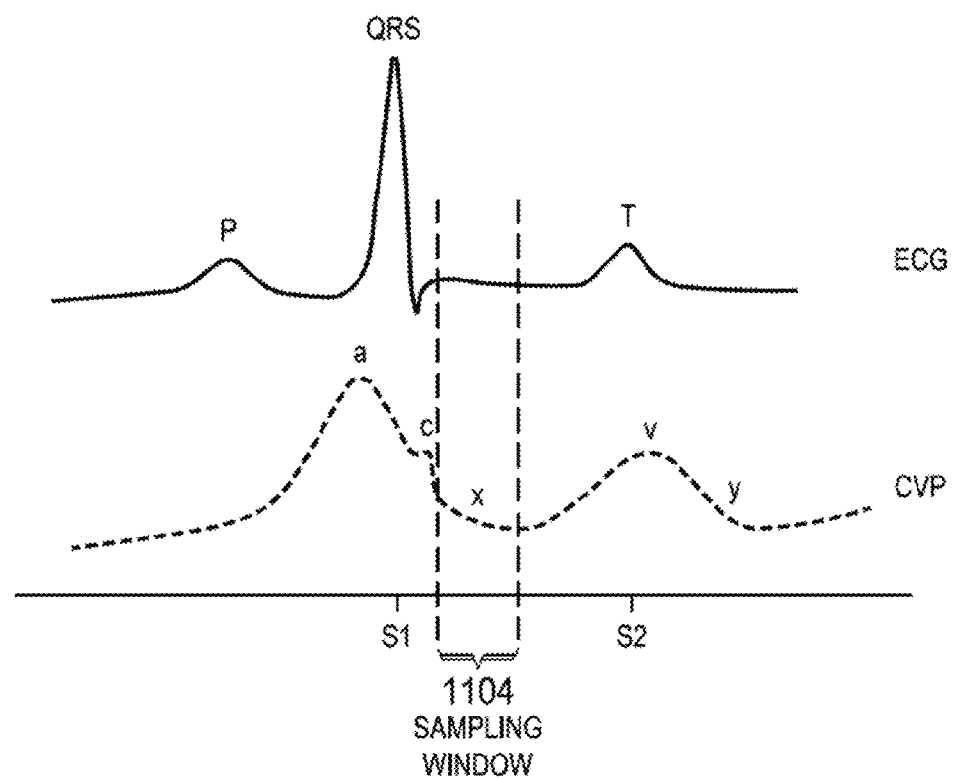
FIG. 11D is a graph of a sampling window in a biphasic cardiac activity of a preferred embodiment.

Referring to FIG. 11A, blood circulation 1100 starts by heart pumping blood into arteries. Blood volume 1101 changes rapidly from minimum 1102 to its maximum value called systolic peak 1103 during systole. Peak to peak interval 1108 is the time between systolic peaks 1103 and 1105. Pulse interval 1107 is the time between minimum 1102 and minimum 1106. Sampling interval 1104 is the time between minimum 1102 and systolic peak 1103.

Referring to FIGS. 11A, 11B, 11C, and 11D, in biphasic cardiac activity when the left ventricular is in systole, the blood flow and hydrodynamic pressure 1109 and 1110 is at a maximum, ventricular ejection time is small, and blood flow velocity is higher. The blood pressure and volume then decrease during diastole 1111 with a slower rate. In a preferred embodiment, the arterial oxygen saturation is sampled and computed during systole, i.e., sampling window 1104, where the heart pushes blood into the arteries. In this time period, the crest time, blood is mainly controlled by heart as a pump forcing blood into arteries. The amplitude of diastolic peak 1112 in which the heart is relaxing, changes dramatically in the presence of motion compared to systolic time period. Sampling window 1104 is determined during systole and results in a motion-free sampling of the PPG signal during each beat cycle.

In typical methods, a continuous segment of the PPG signal at a single heartbeat or multiple heart beats is used to compute $SpO_2$. In the disclosed cardiac gating $SpO_2$ method, to improve signal quality, a motion-free short segment of signal in each heart beat is chosen from two or more subsequent cardiac cycles to compute $SpO_2$. The heart rate of the patient is an important determinant in cardiac gating. Changes in heart rate over time result in change of location of the motion-free sampling window and length of the sampling window. The disclosed cardiac gating method tracks heart rate changes and the motion-free sampling window over time to build two cardiac synchronized cardiac gated red and infrared signals from which $SpO_2$ is ultimately calculated.

Another main contributing error in the presence of motion artifact is the venous return effect of venous blood movement. Venous return blood movement is governed by two physiological processes: (i) respiratory pump and (ii) skeletal muscle pump. The effect of respiratory pump adds a low frequency signal to the PPG signal which is in phase with expiration and inspiration. The respiration rate is typically between 8 to 30 breathes per minute and a respiration cycle takes at least two heart beats. This component of the venous return effect on the PPG signal is in low frequency region. The limited effect of the respiratory portion of venous return on the calculation of the $SpO_2$ is removed by (i) baseline removal filters in enhancement unit 1000, as previously described (ii) computation of $SpO_2$ using the first order derivatives of red and infrared signals (as opposed to original red and infrared signals) and cardiac gating, as will be further described below. Low frequency variation of the respiratory portion of venous return changes the baseline of the signals and when the respiration rate is slow, the baseline will be removed or attenuated by baseline filters or subsequent filtering in signal enhancement unit. Any remaining respiratory related venous return effect is removed by taking the first derivative of the red and infrared signals.

Figure 12:
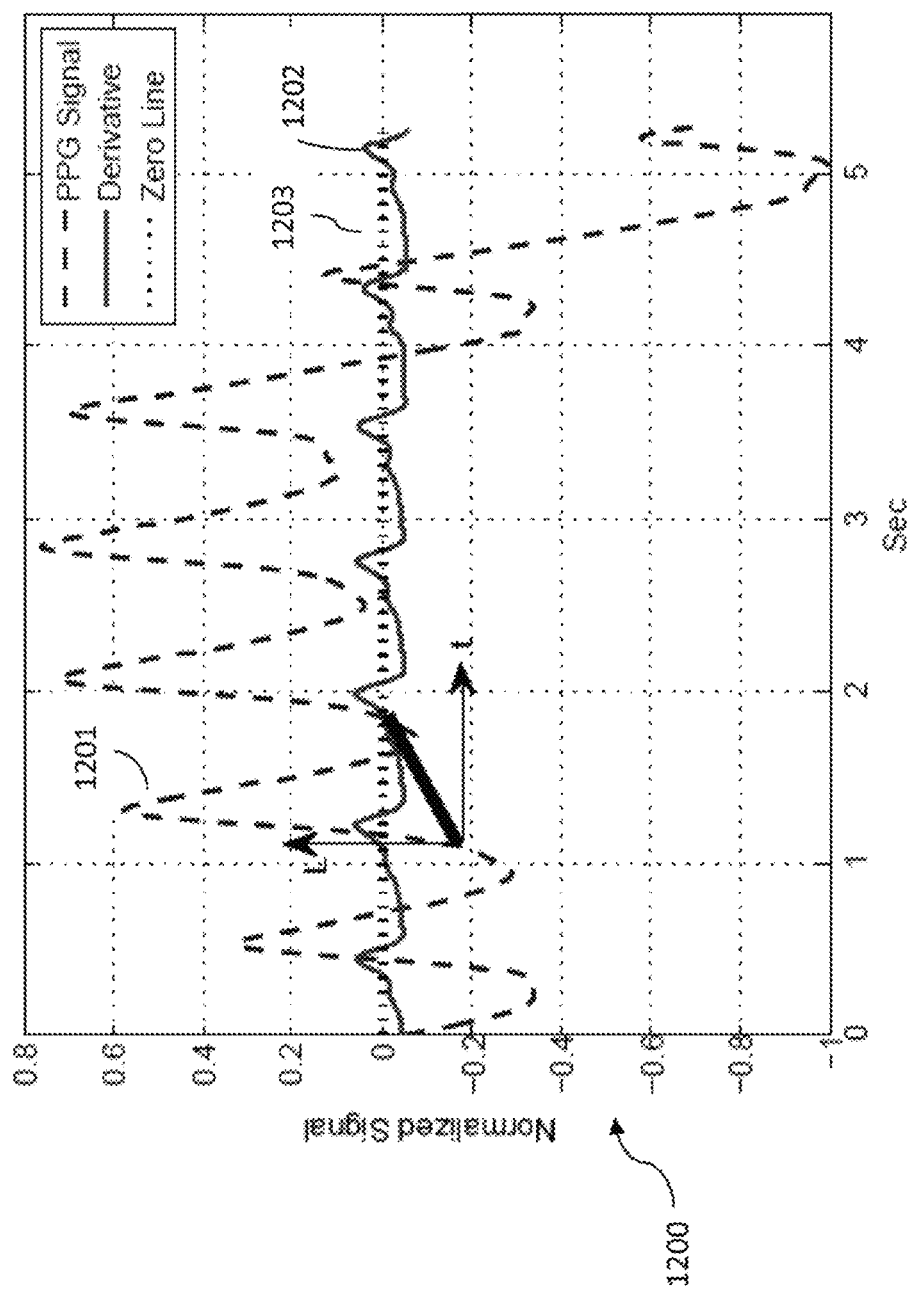
FIG. 12 is a graph of respiratory effect on a baseline of a preferred embodiment.

Referring to FIG. 12, graph 1200 shows an experimental result where the user performs a deep long breathe at heart rate of 78 beats per minute. Graph 1200 includes plots of PPG signal 1201, first derivative 1202 of PPG signal 1201, and zero line 1203. Graph 1200 shows the transition between expiration and inspiration phases which represents baseline changes due to respiratory-related venous return.

Figure 13:
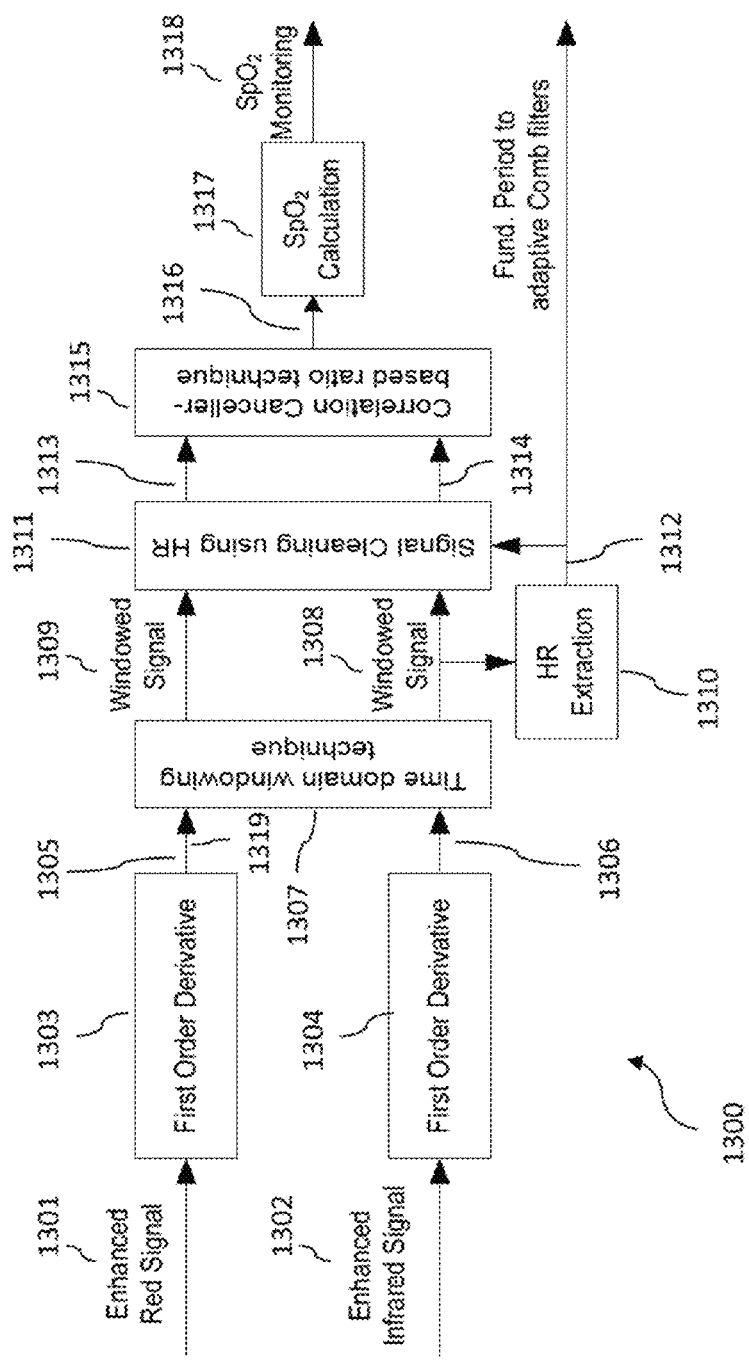
FIG. 13 is a block diagram of a cardiac gating unit of a preferred embodiment.

Referring to FIG. 13, cardiac gating method 1300 for determining a crest time duration of a set of PPG signals will be further described. At step 1303, a first order derivative of enhanced red signal 1301 is taken to generate first derivative red signal 1305. In this step, first derivative red signal 1305 is negated to generate negated first derivative red signal 1319. At step 1304, a first order derivative of enhanced infrared signal 1302 is taken to generate first derivative infrared signal 1306.

At step 1307, a time window is generated using a set of conditions. The set of conditions determine time durations in which first derivative red signal 1305 is less than or equal to zero, and first derivative infrared signal 1306 is greater than or equal to zero. If this set of conditions exists, then the time window value is one. If not, then the time window is zero. In this step, each of the first order derivative infrared signal 1306 and negated first derivative red signal 1319 is multiplied by the time domain window to generate windowed red signal 1309 and windowed infrared signal 1308. The time domain windowing step determines the desired time duration from the beginning of the systolic phase up to peak systolic point.

At step 1310, heart rate 1312 is extracted using windowed infrared signal 1308. At step 1311, windowed infrared signal 1308 and windowed red signal 1309 are "cleaned" using heart rate 1312 to remove the other time durations that do not meet the set of conditions. In order to remove unwanted time durations on the windowed signals and clean each signal, an autocorrelation based method derives the average heart rate for each frame of the data, as previously described, to generate clean red signal 1313 and clean infrared signal 1314.

At step 1315, an optimum ratio 1316 of clean red signal 1313 to clean infrared signal 1314 is calculated in the presence of motion artifact using a correlation canceller ratio measurement, as will be further described below. At step 1317, $SpO_2$ is calculated using the optimum ratio 1316.

Figure 14:
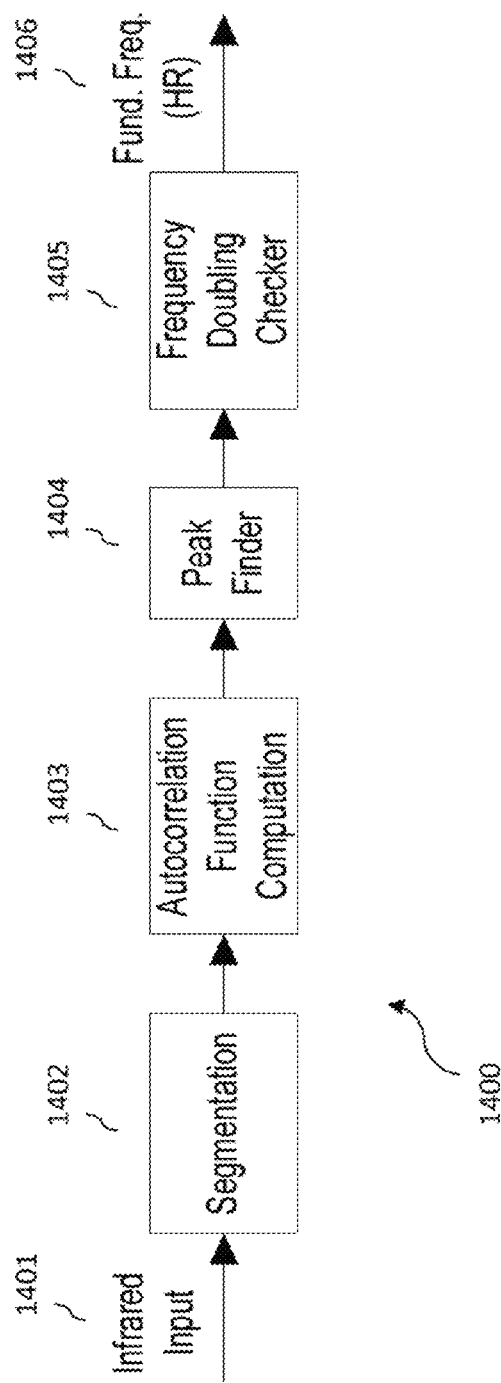
FIG. 14 is a block diagram of a heart rate extractor of a preferred embodiment.

Referring to FIG. 14, step 1310 will be further described as method 1400. Due to its higher amplitude compared to a windowed red signal, windowed infrared signal 1401 is segmented at step 1402. At step 1403, for each segment of the windowed infrared signal, an autocorrelation function (ACF) is computed in the range of time periods for human heart rate, as previously described. At step 1404, a peak finder finds the first dominant peak of the autocorrelation function.

Fundamental frequency doubling is an issue in fundamental frequency (e.g heart rate) extraction techniques. In the heart rate extraction from a motion-corrupted PPG signal, this issue becomes more troublesome in the presence of the motion artifact which changes the shape of the signal in time domain.

At step 1405, a frequency checker removes any frequency doubling. Amplitude of the signal in unwanted time durations is less than amplitude of the signal in the peak systolic point. Therefore, a sliding window with the length of three by average of number of samples in each heart beat moves on the signal. Within this window, the time durations whose peak value of the signal is less than a predetermined threshold multiplied by a mean value are removed. In a preferred embodiment, the predetermined threshold is 0.7. On the modified signal at this point, an autocorrelation function is computed and a peak finder finds the peak value of the autocorrelation function. The maximum peak is chosen for the current window to generate a fundamental frequency 1406, which is the heart rate.

Figure 15:
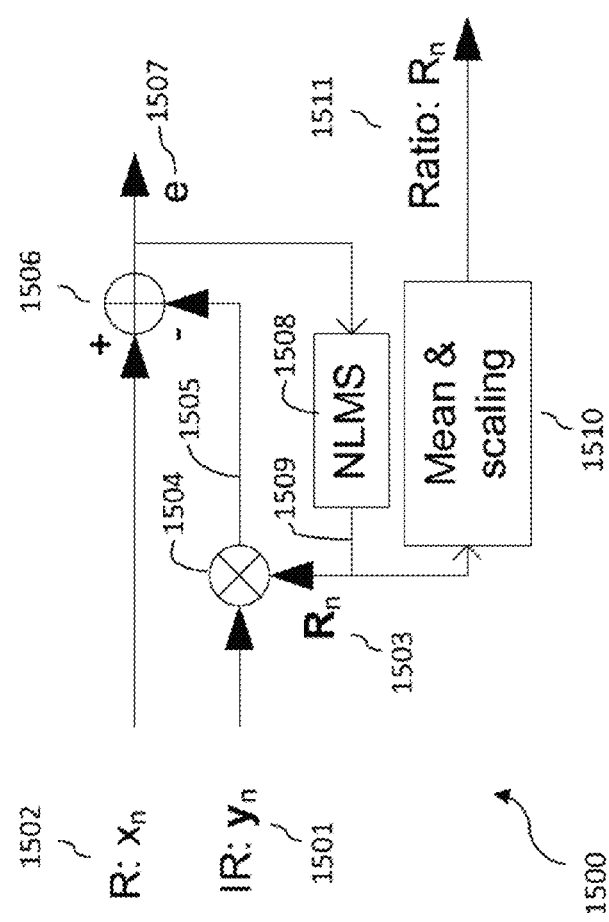
FIG. 15 is a block diagram of a correlation canceller of a preferred embodiment.

Referring to FIG. 15, step 1315 will be described as correlation canceller 1500. Correlation canceller 1500 uses clean infrared signal 1501 as a reference signal ($y_n$) in a correlation canceller loop. The ratio vector 1503 $R_n$ of length N is available at time n. At step 1504, an estimated infrared signal 1505 $\hat{x}_n$ is computed by linear combination of R samples of clean infrared signal 1501 $y_n$. At step 1506, an error estimation signal 1507 is calculated by e(n)=x(n)−x̂$_n$ using clean red signal 1502 x(n) and estimated infrared signal 1505 x̂$_n$. At step 1508, next ratio vector 1509 R$_{n+1}$ is calculated by minimizing mean square error of error estimation signal 1507 e(n) with respect to ratio vector R$_n$. Steps 1504, 1506, and 1508 are repeated for next sample, n+1.

After computing the next ratio vector 1509 of length N, the mean value of ratio vector 1509 is computed and multiplied by the length of the ratio vector N at step 1510 to build a current optimum ratio 1511 of red to infrared light intensities. As seen in FIG. 15, the adaptive iterative solution is a gradient-decent method which results in the calculation of the final ratio value from which SpO$_2$ is derived.

Test 1

Figure 16:
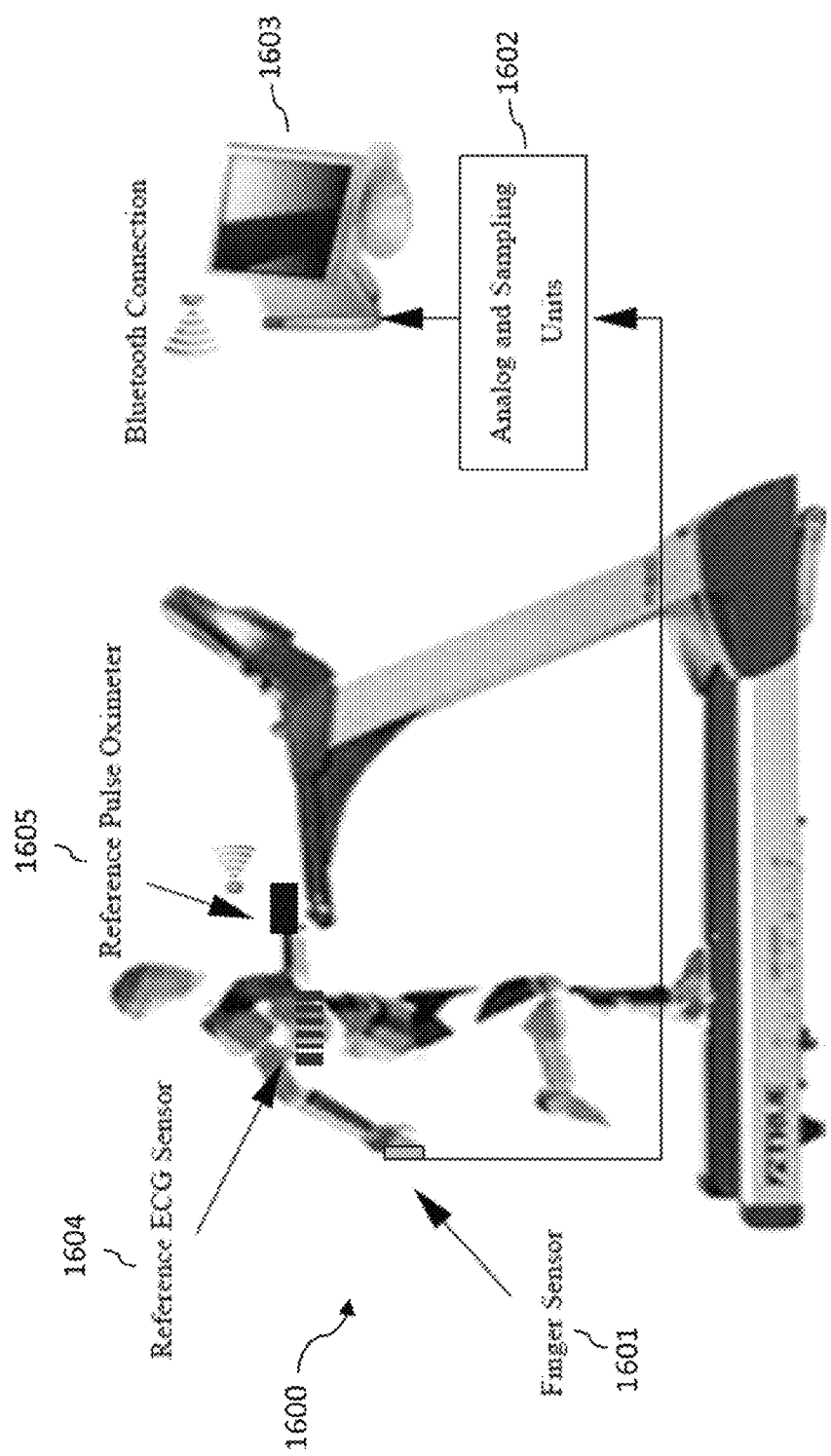
FIG. 16 is a schematic of an experimental setup of a preferred embodiment.

Referring to FIG. 16, experimental sensor platform setup 1600 includes a finger probe 1601 with red LED and infrared LED, respectively, connected to analog and sampling unit 1602, which is connected to computer 1603. Analog and sampling unit 1602 includes an analog conditioning circuit which limits the bandwidth of the PPG signal to 70 Hz. The PPG signal is acquired with sampling rate of 250 Hz using a battery powered module with an analog front end circuit and with an onboard processor. A hamming window and a low-pass filter, with cutoff frequency at 8 Hz, are implemented on the evaluation module in order to attenuate any unwanted signals. Other sensors on various locations of the body and reflection or transmission mode sensors may be employed.

For the performance evaluation, each participant wore a commercially available wireless ECG sensor 1603 and SpO$_2$ sensor 1604, each of which is connected to computer 1603 via Bluetooth. The experiment was performed on a treadmill to maintain control over speed and durations. To test and validate the disclosed methods, the PPG signal is collected from different subjects performing various motions. Three experiments are designed to observe effect of motion artifact and quantify signal enhancement using objective and subjective tests.

The motion types in this test are standing still, up-down "vertical" hand movement, and left-right hand motions of the hand with different speed and acceleration, bending of the finger, walking and running at different speeds. Six subjects between ages of 19-50 participated in the experimentation. For the objective test, an experiment was designed to validate the performance of the disclosed method during normal physical activities (standing, walking and running) One participant, male 28 years old, performed a 30 minute exercise test. This exercise test consisted of 5 minutes walking at 1 mph, 5 min walking at 2 mph, 5 minutes walking in 3 mph, 5 minutes running at 4 mph, 5 minutes running in 5 mph and then a 5 minutes cool down. The cool down included 1 minute running at 4 mph, 1 minute walking at 3 mph, 1 minute walking at 2 mph, 1 minute standing at rest. Six participants completed controlled subjective experiment by walking on the treadmill for 1.5 minutes at 2 mph, then running at the speed of 3.5 mph for another 1.5 minutes and finally running for 2 minutes at 5 mph.

Referring to FIG. 17A, graph 1700 shows noisy PPG signal 1701 collected to observe effect of motion artifact through various motions at different time periods. At segment 1702 the user is standing in place. At segment 1703, the user is moving his hand up and down. At segment 1704, the user is moving his hand left to right. At segment 1705, the user is bending the finger to which the PPG sensor is attached. At segment 1706, the user is walking and running.

Referring to FIG. 17B, graph 1707 shows plots 1708 and 1709 of the time domain of the original signal and the enhanced signal, respectively. As can be seen, motion artifact has changed the shape and periodicity of plot 1708 of the original signal. Motion artifact is removed in plot 1709 of the enhanced signal.

Retelling to FIG. 17C, graph 1707 shows plots 1711 and 1712 of the autocorrelation function of the original signal and the enhanced signal, respectively. Improvement of the autocorrelation function is observed from plot 1711 of the original signal to plot 1712 of the enhanced signal, which enables a reliable heart rate computation.

Figure 17D:
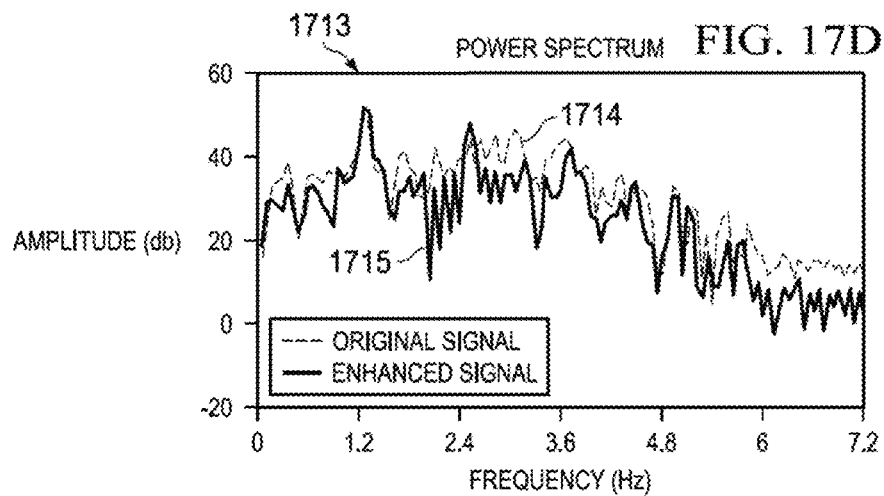
FIG. 17D is a graph of a power spectrum of a preferred embodiment.

Referring to FIG. 17D, graph 1713 shows plots 1714 and 1715 of the frequency content of the original signal and the enhanced signal, respectively.

After reducing the effect of motion, heart rate and SpO$_2$ are computed every 6 sec (e.g. 1500 samples) with no overlap between frames of data for noisy PPG signal 1701.

Figure 17E:
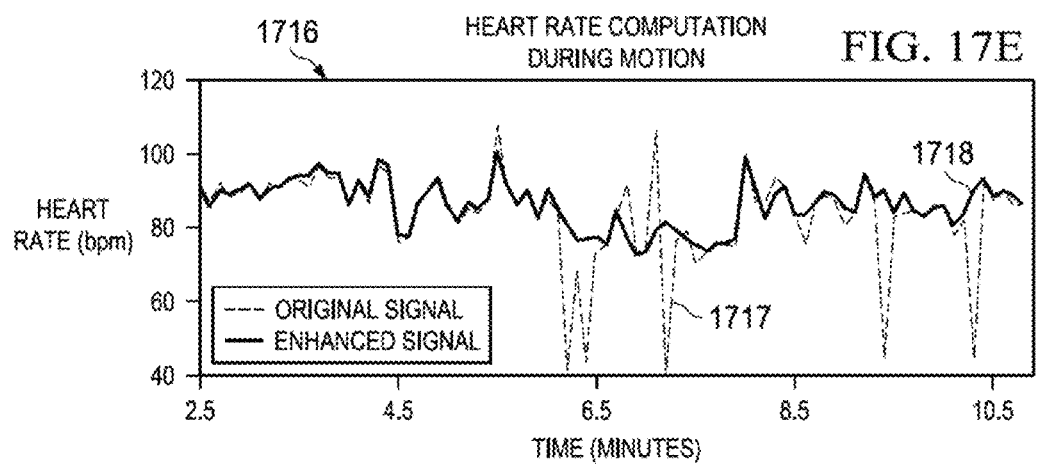
FIG. 17E is a graph of a heart rate of a preferred embodiment.

Referring to FIG. 17E, graph 1716 shows plots 1717 and 1718 of the extracted heart rate from the original signal and the enhanced signal e.g. after removal of tissue effect, respectively. The fundamental period, extracted using method 1400, is used for computation of the heart rate for the enhanced signal 1718. As seen, after enhancing the signal, a robust heart rate computation is provided.

Figure 17F:
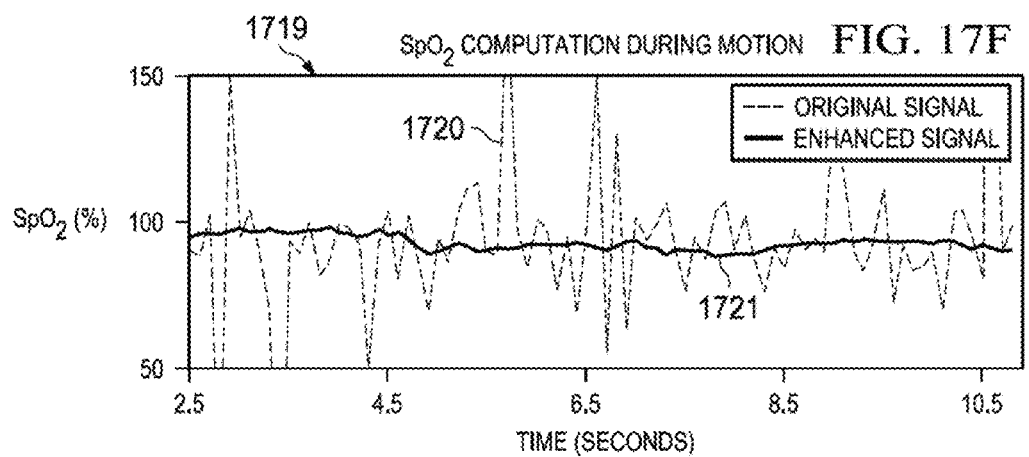
FIG. 17F is a graph of an $SpO_2$ of a preferred embodiment.

Referring to FIG. 17F, graph 1719 shows plots 1720 and 1721 of the SpO$_2$ calculation from the original signal and the enhanced signal, respectively. SpO$_2$ computation is very sensitive to motion. The SpO$_2$ values extracted from the original signal in plot 1720 is unreliable while the enhanced signal e.g. after removal of tissue and venous effect in plot 1721 provides robust computation of the SpO$_2$.

Figure 18A:
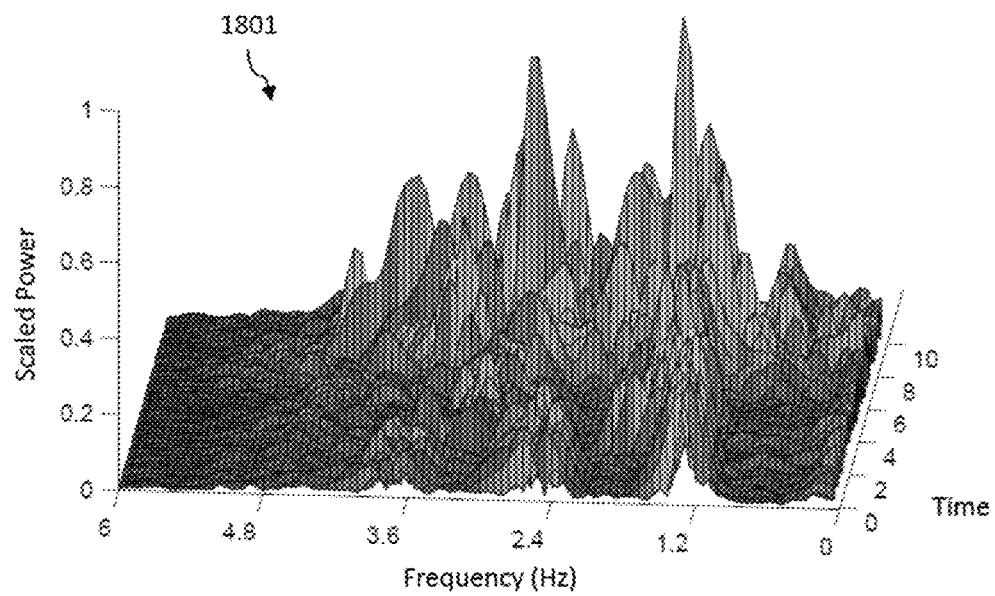
FIG. 18A is a spectrogram of an original PPG signal of a preferred embodiment.
Figure 18B:
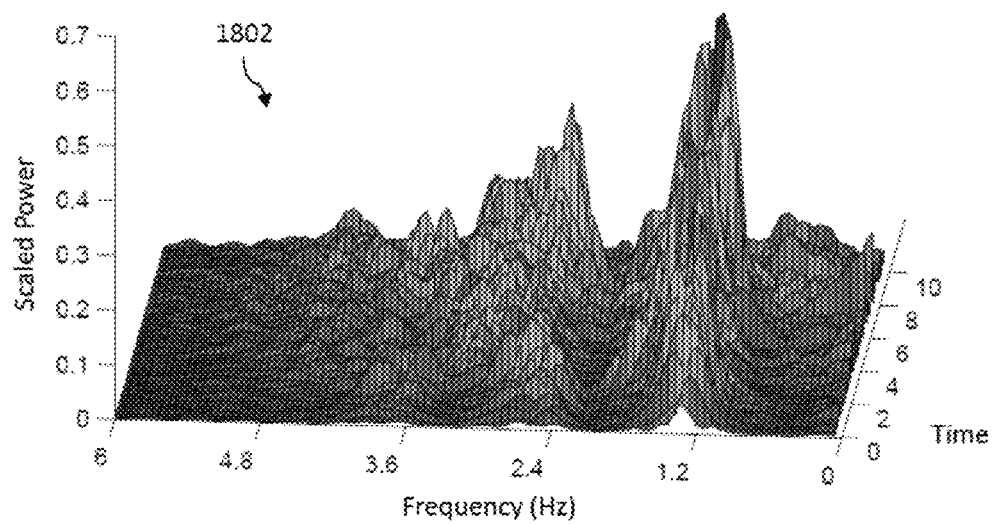
FIG. 18B is a spectrogram of an enhanced PPG signal of a preferred embodiment.

Referring to FIGS. 18A and 18B, spectrogram 1801 of the original signal and spectrogram 1802 of the enhanced signal are respectively shown. Spectrograms 1801 and 1802 show the effect of motion on the PPG signal. Each spectrogram is computed using Short-Time Fourier Transform ("STFT") with window size of 2048, overlap size of 1024 and 4096 point Fast Fourier Transform ("FFT"). High power noise component which leads to inaccurate and unreliable computation of the heart rate and SpO$_2$ is seen in spectrogram 1801. The removal of high power noise components in spectrogram 1802 leads to restoration of the true power of the signal. Harmonic enhancement is observed in spectrogram 1802 which results in enhancement of the autocorrelation function and reliable heart rate computation.

Referring to FIGS. 19A and 19B, graphs 1900 and 1902 show ECG signal curve 1901 and PPG signal curve 1903, respectively, collected using the ECG sensor and the finger clip PPG sensor, respectively, during the experiment. As shown by ECG signal curve 1901 and PPG signal curve 1903, there is a corresponding peak value for every QRS complex of ECG waveform.

Referring to FIG. 19C, graph 1904 depicts reference heart rate 1905, original heart rate 1907, and enhanced heart rate 1906.

Referring to FIGS. 19D and 19E, graph 1908 plots original heart rate 1909 and graph 1919 plots enhanced heart rate 1911. Graphs 1908 and 1910 show the difference between heart rate computed using original and enhanced signals, respectively.

Referring to FIG. 19F, graph 1912 includes the computed SpO$_2$ for reference stationary signal 1913, original signal 1915, and enhanced signal 1915. As can be seen, before applying the disclosed embodiments, in many cases the ratio of ratios fails to compute the SpO$_2$.

Bland-Altman difference plots were used to analyze the agreement between results from the disclosed embodiments and reference measurements. Limit of Agreement (LOA) in this analysis is defined as average difference ±1.96 standard deviation of the difference ([µ−1.96σ, µ+1.96 σ]). 95% of all differences lies inside the LOA. Heart rate and SpO$_2$ values are extracted every 6 second. 300 pairs of heart rate measurement are obtained.

Figure 19G:
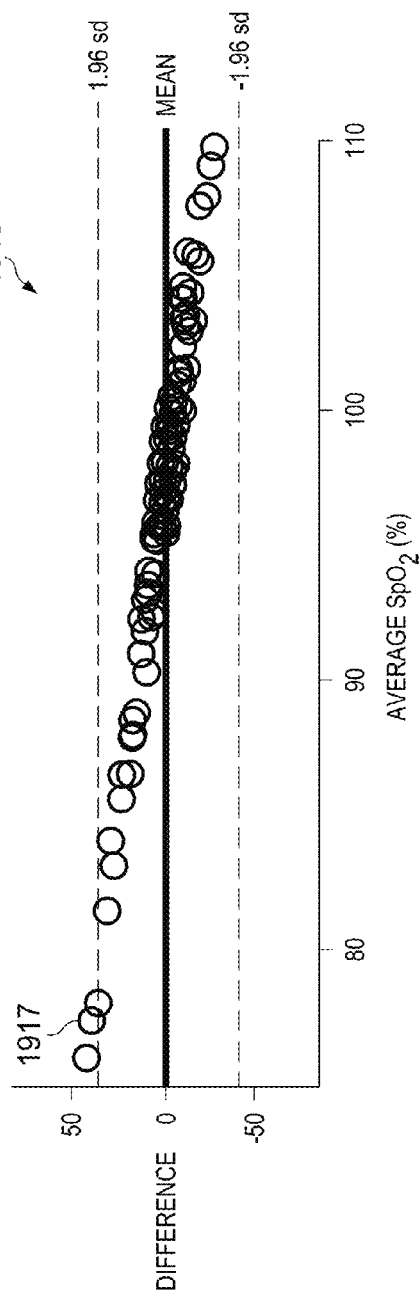
FIG. 19G is a graph of a Bland-Altman plot of $SpO_2$ calculated from an original signal.
Figure 19H:
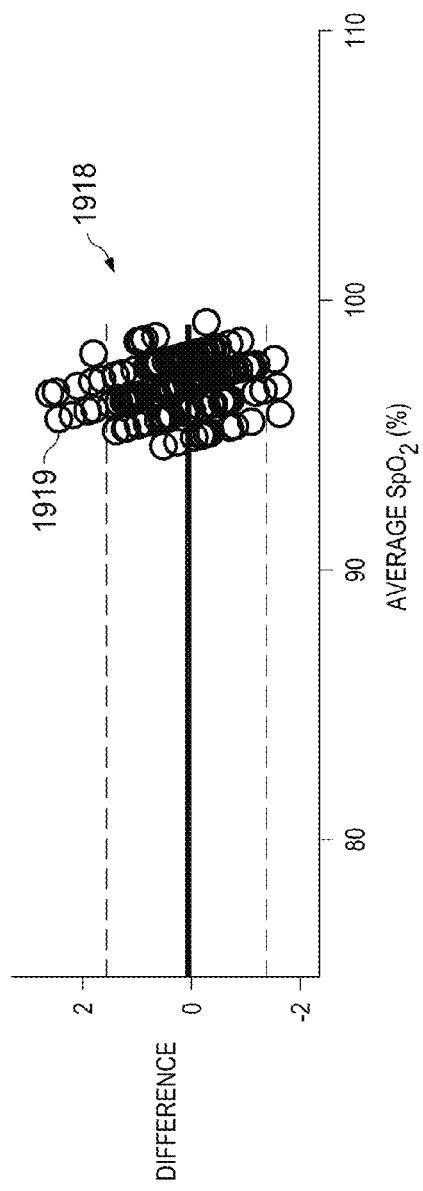
FIG. 19H is a graph of a Bland-Altman plot of $SpO_2$ calculated from an enhanced signal.

Referring to FIGS. 19G and 19H, graphs 1916 and 1918 include the Bland-Altman plot for SpO$_2$ computed using original signal 1917 and enhanced signal 1919, respectively.

A correlation coefficient is defined as the covariance of the variables divided by their standard deviations. Correlation and agreement analyses are compared in Table 1 below. Much higher correlation and agreement are achieved after enhancing the original signal with the disclosed embodiments for SpO$_2$ and heart rate. The correlation coefficient of SpO$_2$ measurement after applying the disclosed embodiments was 0.71 with p-value, i.e., the probability of obtaining a correlation as large as the one obtained randomly, less than 0.00001. There is no correlation between SpO$_2$ computed from the original signal due to high power noise component in the original signal. For the purpose of comparison, the DST method is also implemented using an adaptive filter of order 32. Reference signals are generated by sweeping SpO$_2$ with step size of 0.01 from 0% to 100%. SpO$_2$ is computed by finding the rightmost peak of the power plot and results are summarized in Table 1 below. There is a low correlation between the DST method and the reference SpO$_2$ measurements. The disclosed embodiments enhance the original signal to provide a more reliable SpO$_2$ reading with higher correlation.

TABLE 1

COMPARISON OF HEART RATE AND
SpO$_2$ ACHIEVED BEFORE AND AFTER ALGORITHM

| Parameters | Corr. | Mean Bias | Mean Abs. Bias | LOA |
|---|---|---|---|---|
| Heart Rate (Orig.) | 0.91 | −2.3 | 8.7 | [−23.5, 19.0] |
| Heart Rate (Enh.) | 0.99 | 0.36 | 2.1 | [−5.3, 6.0] |
| SpO$_2$ (Orig./Eqn. (19)) | 0 | −1.8 | 6.9 | [−26.5, 23.0] |
| SpO$_2$ (Orig./DST) | 0.1 | −5.3 | 25.6 | [−54.3, 43.9] |
| SpO$_2$ (Enh.) | 0.73 | 0.15 | 0.6 | [−1.3, 1.6] |

Figure 20:
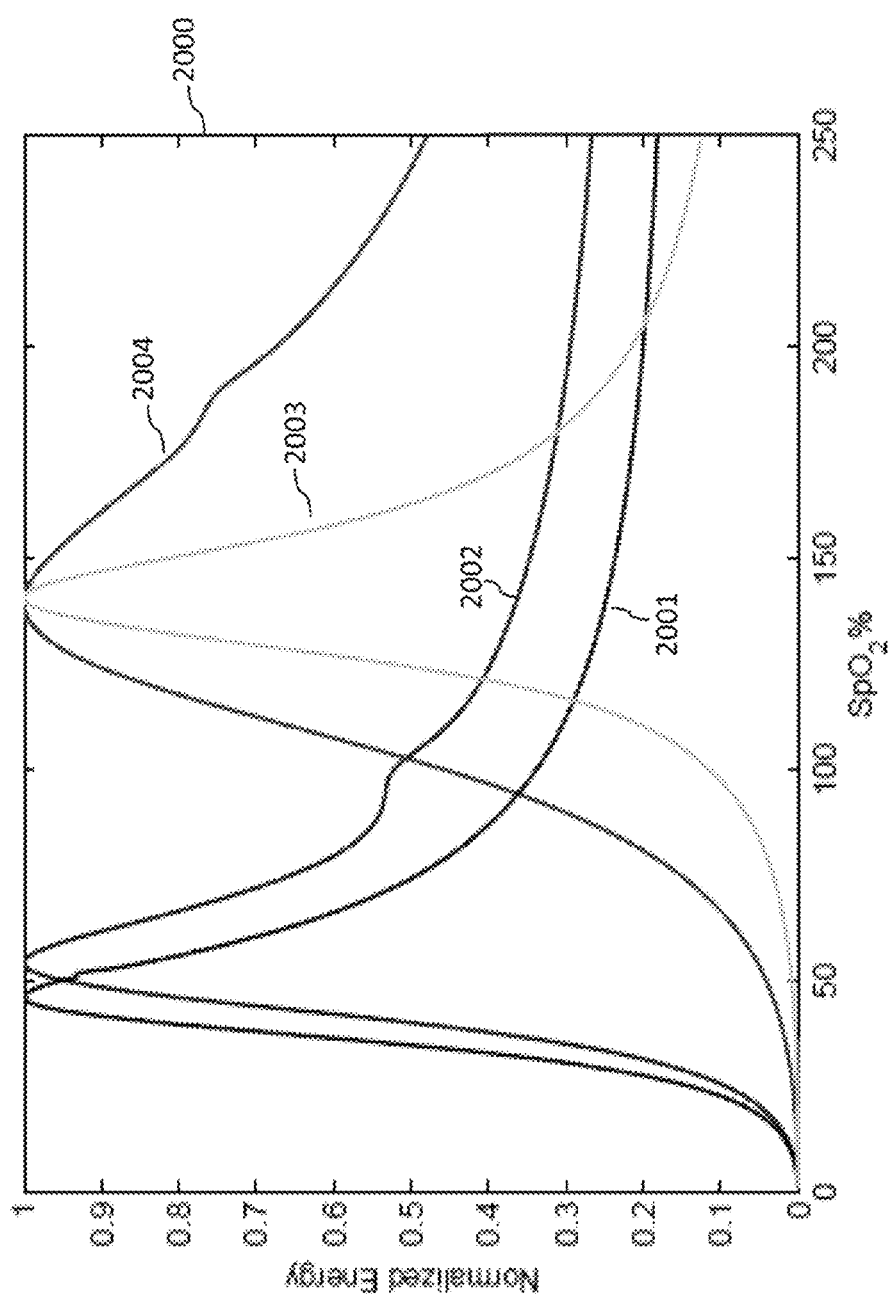
FIG. 20 is a graph of a power plot of the DST method.

Referring to FIG. 20, graph 2000 shows common errors where the DST method reports a false reading due to motion artifact. To observe the behavior of the output power plot, SpO$_2$ is intentionally swept in a larger range. The DST method expects multiple peaks in the range of 0% to 100% where the assumption is that the right-most peak corresponds to arterial oxygen saturation. The amplitude of the peak associated with arterial oxygen saturation is typically very small as shown in curve 2002. These peaks can easily be affected and concealed by motion artifact as shown in curves 2001 and 2002 where there is no peak related to arterial oxygen saturation on curve 2001. In curves 2003 and 2004, not only the peaks are affected by motion artifact but also curves 2003 and 2004 are increasing functions of SpO$_2$ in the range 0% to 100%. To compare the disclosed embodiment versus the DST method more specifically, we computed the correlation coefficient for various levels of motions, i.e. 1 mph, 3 mph, 5 mph. The correlation coefficient for the disclosed embodiments were 0.85, 0.78, 0.64 and 0.52, 0.09, 0.03, for the DST method.

Figure 21B:
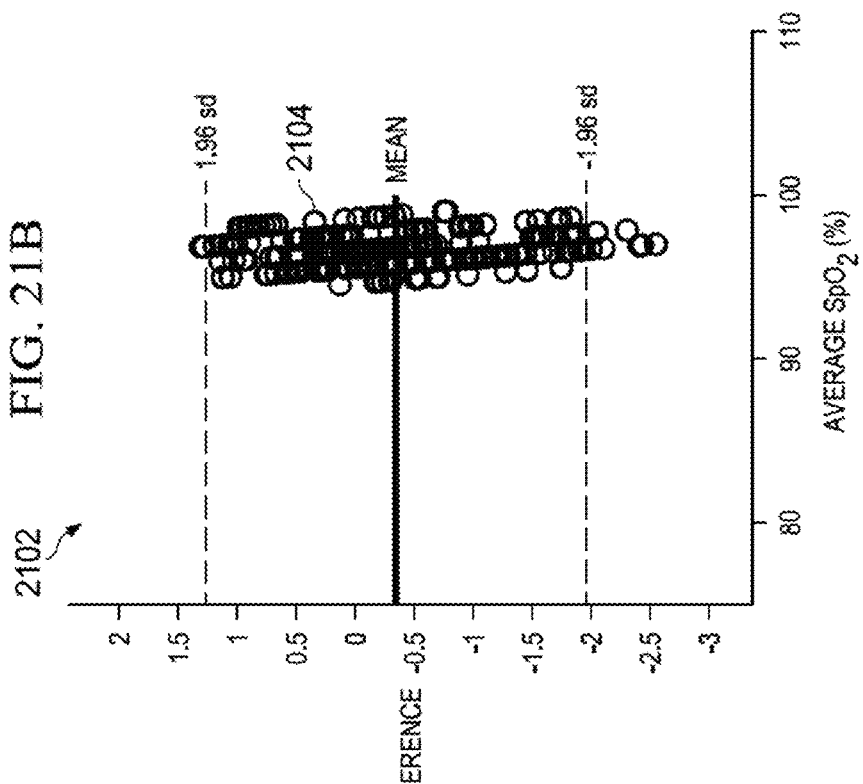
FIG. 21B is a graph of a Bland-Altman plot of $SpO_2$ of a preferred embodiment.
Figure 21A:
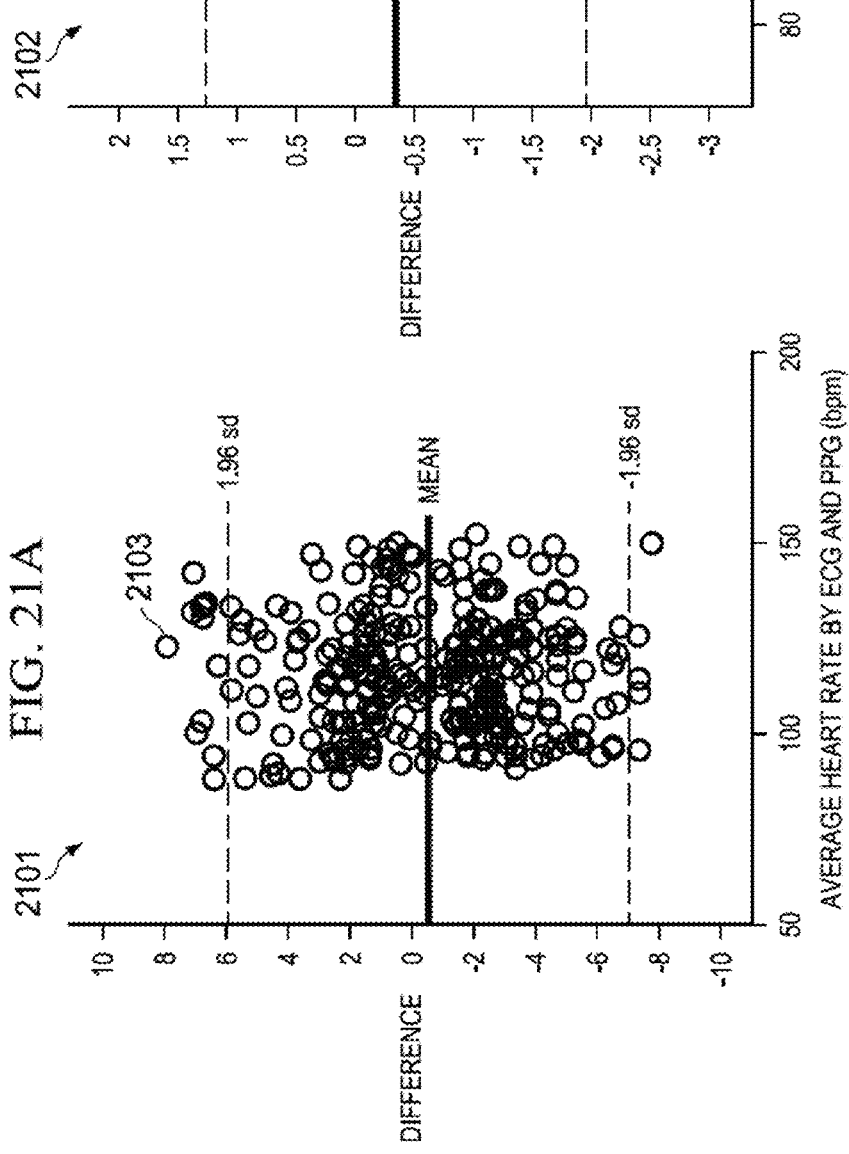
FIG. 21A is a graph of a Bland-Altman plot of heart rate of a preferred embodiment.

Referring to FIGS. 21A and 21B, graphs 2101 and 2102 show the Bland-Altman plot show results for heart rate 2103 and SpO$_2$ 2104, respectively. A total of 300 heart rate measurement pairs and 295 valid SpO$_2$ readings were computed after enhancement of the red and infrared signals. Results of this experimentation are summarized in Table 2, below. These results for multi-subject experiment overall show a high level of agreement and correlation between reference measurements and the disclosed method.

TABLE 2

EVALUATION ON MULTI-SUBJECT EXPERIMENT

| Parameters | Corr. | Mean Bias | Mean Abs. Bias | LOA |
|---|---|---|---|---|
| Heart Rate | 0.98 | −0.57 | 2.7 | [−7.0, 5.9] |
| SpO$_2$ | 0.7 | −0.35 | 0.71 | [−1.9, 1.2] |

In order to observe sensitivity of filtering to rapid changes of heart rate, the beat-to-beat heart rate was extracted after enhancing the noisy signal with the second stage of the disclosed method while using autocorrelation-based fundamental period extractor and update rule for $\beta_{opt}$.

Due to high similarity of Blood Pressure (BP) signal with the PPG signal, a BP signal from the MIT-BIH polysomnographic database, dataset "slp01a" was used to evaluate the beat-to-beat heart rate. This database includes BP and ECG signals. For evaluation purposes, a reference heart rate is derived from the annotated ECG signal in the database. The BP signal is standardized to have zero mean and unity variance. Noise is artificially added to 1 hour of clean BP signal and signals $x_1$ and $x_2$ are generated according to Eq. 8 with $r_a$=0.9 and $r_v$=0.6, which are typical optical density ratios in artery and vein, also in Eq. 7. The noise $\mathcal{N}(0,1)$ is filtered with a FIR low pass filter with a cutoff frequency of 8 Hz and multiplied by a gain factor to have unity variance in $x_1$.

To extract the beat-to-beat heart rate from the BP signal, a threshold-based method is used which finds the maximum point on the signal in each cycle. The BP signal is converted to frames of size 700 samples. For each new frame, the mean value is subtracted from the signal and a clipping level is extracted by computing a fixed percentage of the maximum amplitude of the signal in that frame. The center clipped signal, i.e., the original signal minus the clipping level, is extracted and a peak finder finds the location of the peak value on the center clipped waveform. The results are summarized in Table 3 below. The relative error in Table 3 is used for quantifying beat-to-beat HR and defined as:

$$\text{Error} = \sqrt{\frac{1}{N}\sum_{j=1}^{N}\left[\frac{HR(j) - Ref(j)}{Ref(j)}\right]^2} \qquad \text{Eq. 22}$$

where N is the total number of beats, HR is the measured heart rate, and Ref is the reference heart rate obtained from the annotated ECG signal in the database.

TABLE 3

BEAT-TO-BEAT HR

| Parameters | Error | Corr. | Mean Bias | Mean Abs. Bias | LOA |
|---|---|---|---|---|---|
| Orig. Clean BP | 0.021 | 0.99 | 0 | 1.12 | [−4.28, 4.28] |
| Noisy BP Signal | 0.49 | 0.78 | 0.10 | 8.22 | [−21.12, 21.24] |
| Enh. BP Signal | 0.024 | 0.98 | 0 | 1.32 | [−4.59, 4.59] |

The simulation using MIT-BIH database shows that beat-to-beat heart rate is reliably extracted using the disclosed method even though there is an estimation error in the fundamental period due to rapid changes of the heart rate. Due to rapid changes in heart rate and high power of added noise, a threshold-based method has poor performance in extracting the heart rate from a noisy BP signal even though threshold is adaptively adjusted to have the best result. There is a high correlation between beat-to-beat heart rate from the enhanced signal and the reference beat-to-beat heart rate. To further reduce the effect of rhythm irregularities on reference noise in special applications, the disclosed method can be tuned appropriately based on features that are supposed to be extracted from the enhanced output signals for that particular application. For example, the size of autocorrelation window can be tuned based on the rate of changes of heart beat or it can be replaced with an available reliable beat-to-beat heart rate extractor.

Test 2

To evaluate the disclosed real-time fundamental estimation method of FIG. 7, corrupted and noisy PPG signal named a44091c dataset from MIT MIMIC II waveform database is used. The sampling frequency of this database is 125 Hz and total number of simulated samples is 360000, 48 minutes of data gathered from an Intensive Care Unit (ICU) monitor.

Figure 22:
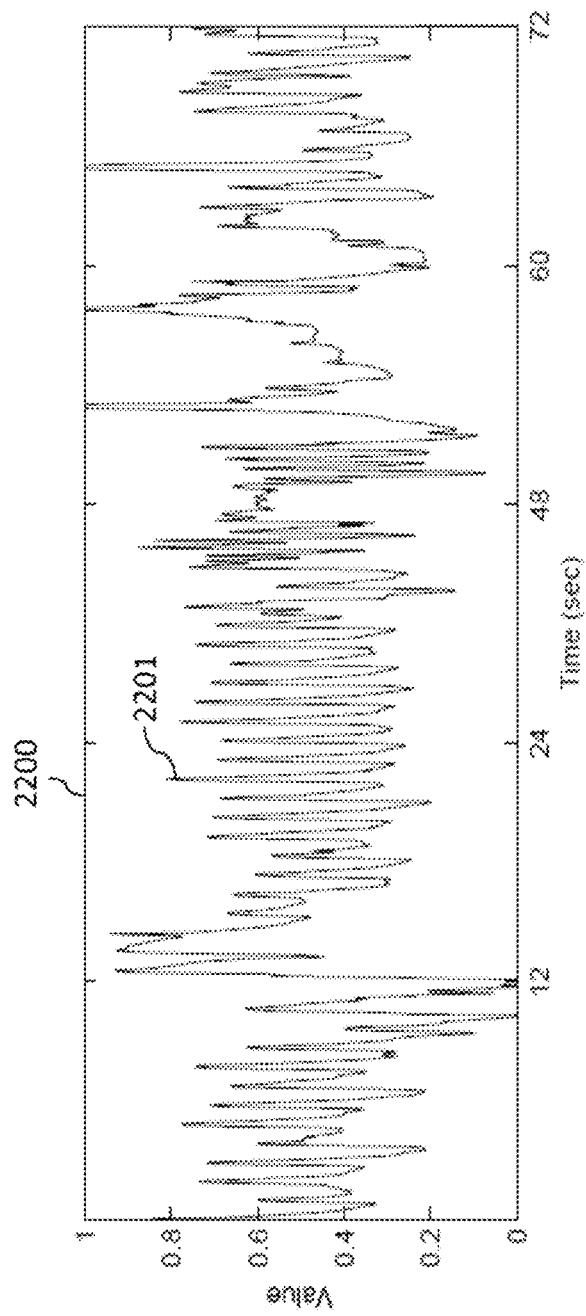
FIG. 22 is a graph of a simulated portion of a noisy PPG signal.

Referring to FIG. 22, plot 2201 of graph 2200 shows a small portion (72 sec) of noisy signal of this dataset. This sample of data includes a noise-free segment from approximately t=18 to approximately t=30 and a noisy segment from approximately t=50 to approximately t=72.

Referring to FIGS. 23A, 23B, 23C, and 23D, graph 2301 includes plot 2302 of raw PPG signal. Graph 2303 includes plot 2304 of the extracted fundamental frequency using the disclosed real-time fundamental frequency estimation method. Graphs 2305 and 2307 include plots 2306 and 2308 of the disclosed autocorrelation method. The heart rate is almost stable and the fundamental frequency is about 1 Hz as it can be visually confirmed by plot 2304. The result of the disclosed fundamental frequency estimation method is shown in plot 2304. As can be seen, the frequency estimation method has no error providing a robust estimation of the fundamental frequency.

In the autocorrelation method, the corresponding autocorrelation function is computed and a peak searching is used to find the fundamental frequency between 0.6 Hz and 3.3 Hz. In this experiment, 2000 data samples are used for computation of autocorrelation. As previously discussed, the autocorrelation function does not provide a robust estimation of fundamental frequency. Several of erroneous outputs are marked by "*" on plots 2306 and 2308.

A data collection platform is developed using a finger probe with a red LED and an infrared LED working on 660 nm and 895 nm, respectively. An analog conditioning circuit limits bandwidth of the PPG signal to 70 Hz and the PPG signal is acquired with sampling rate of 250 Hz using a module with an analog front end circuit and with an onboard processor. An FIR hamming window and a low-pass filter with a cutoff frequency at 10 Hz attenuates the unwanted signals.

To validate the embodiments using synthetic noise generation on real data, the PPG signal from a user performing different motions is collected for 12 minutes. Referring to FIG. 24A, graph 2401 includes plot 2402 of the PPG signal. Plot 2402 includes segment 2403 of clean data without motion ("No Motion"), segment 2404 of vertical movement of the hand ("UP-Down Motion"), segment 2405 of horizontal movement of the hand ("Left-Right Motion"), segment 2406 bending of the finger ("Bending"), and segment 2407 of walking. Movements have different accelerations and variations within each segment.

Referring to FIGS. 24B and 24C, graph 2409 includes plot 2410 of the fundamental frequency calculated by the disclosed fundamental frequency estimation method. Graph 2411 includes plot 2412 of the autocorrelation function. 2500 samples of data are used for computation of the autocorrelation function in both autocorrelation and the fundamental frequency estimation method and results are shown. The disclosed method shows superior and robust performance compared to autocorrelation function in which many errors have occurred during bending of the finger and walking from approximately 6 minutes to approximately 12 minutes.

Referring to FIGS. 25A, 25B, and 25C, graph 2501 includes plot 2502 of a motion corrupted PPG signal during left-right movement of the hand. Graph 2503 includes plot 2504 of an improved PPG signal, $\hat{s}(n)$, at the output of adaptive filter during left-right movement of the hand. Graph 2505 includes plot 2506 of a synthetic noise reference in time domain during left-right movement of the hand.

Referring to FIGS. 26A, 26B, and 26C, spectrogram 2601 includes spectrum 2602 of a motion corrupted PPG signal. Spectrogram 2603 includes spectrum 2604 of an improved PPG signal. Spectrogram 2605 includes spectrum 2606 of a synthetic noise reference. As shown, motion artifact components are picked up by the comb filter and the adaptive LMS filter significantly improves the signal spectrogram by reducing noise components of the spectrogram. A normalized LMS adaptive filter of order 20 is used in this experiment.

It will be appreciated by those skilled in the art that the described embodiments disclose significantly more than an abstract idea including technical advancements in the field of data processing and a transformation of data which is directly related to real world objects and situations in that the disclosed embodiments enable a computer to operate more efficiently and improve medical diagnoses and treatments. Specifically, the disclosed embodiments enhance and clean PPG signals by removing signal noise due to motion and venous blood. The clean PPG signals allow for a faster and more accurate calculation of $SpO_2$ and heart rate. The faster and more accurate calculation of $SpO_2$ and heart rate enables more accurate and faster diagnoses and treatment of medical ailments.

It will be appreciated by those skilled in the art that modifications can be made to the embodiments disclosed and remain within the inventive concept. Therefore, this invention is not limited to the specific embodiments disclosed, but is intended to cover changes within the scope and spirit of the claims.

The invention claimed is:

1. A method for enhancing a set of photoplethysmographic signals to calculate a blood oxygen level and a heart rate comprising the steps of:
    removing motion noise from the set of photoplethysmographic signals to generate a set of enhanced signals;
    extracting a fundamental period from the set of enhanced signals;
    determining a venous noise reference from the set of enhanced signals and the fundamental period;
    generating a set of clean signals from the set of enhanced signals and the venous noise reference; and,
    calculating the heart rate and the blood oxygen level from the set of clean signals.

2. The method of claim 1, wherein the step of removing further comprises the steps of:

generating a reference signal from the set of photoplethysmographic signals; and,
filtering motion noise from the set of photoplethysmographic signals using the reference signal.

3. The method of claim 2, wherein the step of filtering further comprises the steps of:
determining a first set of filter criteria;
generating a first filter coefficient from the first set of filter criteria;
applying the first filter coefficient to the reference signal to generate the set of enhanced signals;
generating a first error estimation from the set of enhanced signals and the set of photoplethysmographic signals; and,
updating the first filter coefficient based on the first error estimation.

4. The method of claim 2, wherein the step of extracting a fundamental period further comprises the steps of:
calculating an autocorrelation function of the set of enhanced signals;
calculating a set of time domain windows;
generating a modified autocorrelation function for each of the set of time domain windows;
combining each modified autocorrelation function at a subset of the set of time domain windows;
determining a maximum energy level from the subset of the set of time domain windows; and,
determining the fundamental period from the maximum energy level.

5. The method of claim 1, wherein the set of enhanced signals further comprises an enhanced red signal and an enhanced infrared signal, wherein the step of determining a venous noise reference further comprises the steps of:
extracting an arterial scaled estimate from the set of enhanced signals;
generating a weight based on the arterial scaled estimate;
generating a first error signal from the weight and the arterial scaled estimate;
generating an optimized weight from the weight by minimizing a variance of the first error signal using the fundamental period; and,
generating the venous noise reference from the enhanced red signal, the enhanced infrared signal, and the optimized weight.

6. The method of claim 1, wherein the step of generating a set of clean signals further comprises the steps of:
determining a second set of filter criteria;
generating a second filter coefficient from the second set of filter criteria;
applying the second filter coefficient to the venous noise reference to generate an output;
generating a second error estimation and the set of clean signals from the output and the set of enhanced signals; and,
updating the second filter coefficient based on the second error estimation.

7. The method of claim 1, wherein the step of removing further comprises the steps of:
generating an estimated fundamental frequency from the set of photoplethysmographic signals;
generating a reference noise signal from the estimated fundamental frequency and the set of photoplethysmographic signals;
generating an estimated motion noise from the reference noise signal; and,
generating a second error signal and the set of enhanced signals from the set of photoplethysmographic signals and the estimated motion noise.

8. The method of claim 7, further comprising the step of adjusting a filter coefficient to minimize the second error signal.

9. A method for motion-tolerant processing of a set of photoplethysmographic signals to calculate a blood oxygen level comprising the steps of:
generating a set of processed signals from the set of photoplethysmographic signals;
generating a set of enhanced signals from the set of processed signals;
calculating the blood oxygen level from the set of enhanced signals;
wherein the step of generating a set of enhanced signals from the set of processed signals further comprises the steps of:
removing a set of baseline changes from the set of processed signals to generate a set of baseline signals;
normalizing the set of baseline signals to generate a set of normalized signals;
generating an intermediate reference signal from the set of normalized signals;
filtering the set of normalized signals with the intermediate reference signal to generate a set of filtered signals;
receiving a fundamental period; and,
generating the set of enhanced signals from the set of filtered signals and the fundamental period.

10. The method of claim 9, further comprising the steps of:
generating a photodetector gain and an LED intensity from the set of baseline signals;
driving a set of LEDs with the LED intensity; and,
amplifying a photodetector signal with the photodetector gain.

11. The method of claim 9, wherein the set of enhanced signals further comprise an enhanced red signal and an enhanced infrared signal, and wherein the step of calculating the blood oxygen level from the set of enhanced signals further comprises the steps of:
generating a time window from the enhanced red signal and the enhanced infrared signal based on a set of conditions;
generating a windowed red signal from the time window and the enhanced red signal;
generating a windowed infrared signal from the time window and the enhanced infrared signal;
extracting the fundamental period from the windowed infrared signal;
generating a clean infrared signal from the windowed infrared signal and the fundamental period;
generating a clean red signal from the windowed red signal and the fundamental period;
calculating an optimum ratio from the clean infrared signal and the clean red signal; and,
calculating the blood oxygen level from the optimum ratio.

12. The method of claim 11, wherein the step of extracting the fundamental period from the windowed infrared signal further comprises the steps of:
segmenting the windowed infrared signal into a set of segmented windowed infrared signals;

calculating an autocorrelation function for each of the set of segmented windowed infrared signals to generate a set of autocorrelation functions;

determining a peak for each of the set of autocorrelation functions;

removing a doubled frequency from the set of segmented windowed infrared signals using the peak to generate a modified signal; and, determining a maximum peak from the modified signal to generate the fundamental frequency.

13. The method of claim 11, wherein the step of calculating an optimum ratio further comprises the steps of:

calculating an estimated infrared signal from the clean infrared signal;

calculating an error estimation signal from the clean red signal;

calculating a ratio vector from the error estimation signal;

calculating a mean from the ratio vector; and, calculating the optimum ratio from the mean.

14. A system for enhancing a set of photoplethysmographic signals to calculate a blood oxygen level and a heart rate comprising:

an evaluation module;

a set of photoplethysmographic sensors, each photoplethysmographic sensor connected to the module;

a computing device connected to the module and programmed to carry out the steps of:

removing motion noise from the set of photoplethysmographic signals to generate a set of enhanced signals;

extracting a fundamental period from the set of enhanced signals;

determining a venous noise reference from the set of enhanced signals and the fundamental period;

generating a set of clean signals from the set of enhanced signals and the venous noise reference; and, calculating the heart rate and the blood oxygen level from the set of clean signals.

15. The system of claim 14, wherein the computing device is further programmed to carry out the steps of:

generating a reference signal from the set of photoplethysmographic signals; and, filtering motion noise from the set of photoplethysmographic signals using the reference signal.

16. The system of claim 15, wherein the computing device is further programmed to carry out the steps of:

determining a first set of filter criteria;

generating a first filter coefficient from the first set of filter criteria;

applying the first filter coefficient to the reference signal to generate the set of enhanced signals;

generating a first error estimation from the set of enhanced signals and the set of photoplethysmographic signals; and, updating the first filter coefficient based on the first error estimation.

17. The system of claim 15, wherein the computing device is further programmed to carry out the steps of:

calculating an autocorrelation function of the set of enhanced signals;

calculating a set of time domain windows;

generating a modified autocorrelation function for each of the set of time domain windows;

combining each modified autocorrelation function at a subset of the set of time domain windows;

determining a maximum energy level from the subset of the set of time domain windows; and, determining the fundamental period from the maximum energy level.

18. The system of claim 14, wherein the set of enhanced signals further comprises an enhanced red signal and an enhanced infrared signal, and wherein the computing device is further programmed to carry out the steps of:

extracting an arterial scaled estimate from the set of enhanced signals;

generating a weight based on the arterial scaled estimate;

generating a first error signal from the weight and the arterial scaled estimate;

generating an optimized weight from the weight by minimizing a variance of the first error signal using the fundamental period; and, generating the venous noise reference from the enhanced red signal, the enhanced infrared signal, and the optimized weight.

19. The system of claim 14, wherein the computing device is further programmed to carry out the steps of:

determining a second set of filter criteria;

generating a second filter coefficient from the second set of filter criteria;

applying the second filter coefficient to the venous noise reference to generate an output;

generating a second error estimation and the set of clean signals from the output and the set of enhanced signals; and, updating the second filter coefficient based on the second error estimation.

20. The system of claim 14, wherein the computing device is further programmed to carry out the steps of:

generating an estimated fundamental frequency from the set of photoplethysmographic signals;

generating a reference noise signal from the estimated fundamental frequency and the set of photoplethysmographic signals;

generating an estimated motion noise from the reference noise signal; and, generating a second error signal and the set of enhanced signals from the set of photoplethysmographic signals and the estimated motion noise.

21. The system of claim 20, wherein the computing device is further programmed to carry out the step of adjusting a filter coefficient to minimize the second error signal.

* * * * *